(12) United States Patent
Garcia et al.

(10) Patent No.: US 10,772,704 B2
(45) Date of Patent: *Sep. 15, 2020

(54) END EFFECTOR COUPLER FOR SURGICAL ARM

(71) Applicant: Zimmer Biomet CMF and Thoracic, LLC, Jacksonville, FL (US)

(72) Inventors: Saddy Garcia, St. Augustine, FL (US); Ryan Luby, Ponte Vedra Beach, FL (US); Shawn Robinson, Fleming Island, FL (US); Benjamin Witten, Jacksonville, FL (US); Max Holland Billard, Jacksonville, FL (US); Nicolai Ussin, Saint John's, FL (US); Catherine Boniface, Jacksonville, FL (US); Aurelien Bruneau, Jacksonville, FL (US); Robert Carlton, Alexandria, VA (US); Ralph Paul, Alexandria, VA (US); Demetrius Siachames, Alexandria, VA (US); Jeffrey Schlosser, Menlo Park, CA (US)

(73) Assignee: Zimmer Biomet CMF and Thoracic, LLC, Jacksonville, FL (US)

( * ) Notice: Subject to any disclaimer, the term of this patent is extended or adjusted under 35 U.S.C. 154(b) by 209 days.

This patent is subject to a terminal disclaimer.

(21) Appl. No.: 15/919,150

(22) Filed: Mar. 12, 2018

(65) Prior Publication Data

US 2019/0274777 A1   Sep. 12, 2019

(51) Int. Cl.
*A61B 90/50* (2016.01)
*A61B 90/57* (2016.01)
(Continued)

(52) U.S. Cl.
CPC .............. *A61B 90/50* (2016.02); *A61B 90/57* (2016.02); *A61B 2017/00477* (2013.01);
(Continued)

(58) Field of Classification Search
CPC ......... A61B 90/50; A61B 90/57; F16M 11/06
See application file for complete search history.

(56) References Cited

U.S. PATENT DOCUMENTS 2,752,116 A   6/1956  Minnis
3,910,538 A   10/1975 Baitella
(Continued)

FOREIGN PATENT DOCUMENTS

CN      107614817 A      1/2018
DE   102015104810 A1     9/2016
(Continued)

OTHER PUBLICATIONS

"International Application Serial No. PCT US2018 022004, International Search Report dated Feb. 14, 2019", 8 pgs.
(Continued)

*Primary Examiner* — Zade Coley
(74) *Attorney, Agent, or Firm* — Schwegman Lundberg & Woessner, P.A.

(57) ABSTRACT

An end effector coupler for a surgical arm can include an end effector body, a proximal coupler, and a tool lock. The tool lock can releasably retain a tool stem to the end effector coupler. The tool lock can include a keyed opening, a pin bore, a pin disposed in the bin bore, a biasing element located in the pin bore, and a pin release including an actuator, the pin release operable to retract the pin into to the end effector body to disengage the pin from the tool stem allowing release of the tool stem from the keyed opening.

20 Claims, 33 Drawing Sheets

(51) Int. Cl.
 *F16M 11/06* (2006.01)
 *A61G 13/10* (2006.01)
 *A61B 17/00* (2006.01)

(52) U.S. Cl.
 CPC ...... *A61B 2090/571* (2016.02); *A61G 13/101* (2013.01); *F16M 11/06* (2013.01)

(56) References Cited

U.S. PATENT DOCUMENTS

| | | | |
|---|---|---|---|
| 4,402,481 A | | 9/1983 | Sasaki |
| 4,514,117 A | * | 4/1985 | Scott .................. B23B 31/1075 279/77 |
| 5,779,209 A | | 7/1998 | Rello |
| 6,467,362 B2 | | 10/2002 | Erikson |
| 6,575,653 B1 | | 6/2003 | Kräuter |
| 6,860,877 B1 | * | 3/2005 | Sanchez ................. A61B 17/12 600/229 |
| 7,611,378 B1 | * | 11/2009 | Brekosky ........... H01R 13/5202 439/500 |
| 9,592,096 B2 | | 3/2017 | Maillet et al. |
| D878,585 S | | 3/2020 | Garcia |
| 2002/0017857 A1 | | 2/2002 | Hashimoto et al. |
| 2002/0074472 A1 | | 6/2002 | Gaida et al. |
| 2002/0117857 A1 | | 8/2002 | Eckstein |
| 2002/0177857 A1 | | 11/2002 | Otsuka et al. |
| 2002/0188293 A1 | | 12/2002 | Manzo |
| 2004/0172012 A1 | | 9/2004 | Otsuka et al. |
| 2010/0020002 A1 | | 1/2010 | Van et al. |
| 2010/0200002 A1 | | 8/2010 | Orban, III et al. |
| 2011/0290855 A1 | * | 12/2011 | Moore ................. A61B 17/072 227/180.1 |
| 2011/0315843 A1 | | 12/2011 | Hung |
| 2012/0182134 A1 | | 7/2012 | Doyle |
| 2012/0265240 A1 | | 10/2012 | Ganske et al. |
| 2013/0187022 A1 | | 7/2013 | Duportal et al. |
| 2014/0379038 A1 | | 12/2014 | Dogramadzi et al. |
| 2015/0100066 A1 | | 4/2015 | Kostrzewski et al. |
| 2016/0081753 A1 | | 3/2016 | Kostrzewski |
| 2016/0151120 A1 | | 6/2016 | Kostrzewski et al. |
| 2016/0270780 A1 | * | 9/2016 | Hall ................. A61B 17/07207 |
| 2017/0340210 A1 | | 11/2017 | Chuang |
| 2017/0340389 A1 | | 11/2017 | Otto et al. |
| 2017/0360521 A1 | | 12/2017 | Johnson |
| 2018/0116758 A1 | | 5/2018 | Schlosser et al. |
| 2019/0167356 A1 | | 6/2019 | Britton et al. |
| 2019/0274665 A1 | | 9/2019 | Garcia |
| 2019/0274778 A1 | | 9/2019 | Billard et al. |
| 2019/0274780 A1 | | 9/2019 | Nowatschin et al. |

FOREIGN PATENT DOCUMENTS

| | | |
|---|---|---|
| EP | 2777539 A2 | 9/2014 |
| EP | 2143372 | 12/2014 |
| EP | 3274521 | 1/2018 |
| JP | S57144399 | 9/1982 |
| JP | S63280911 A | 11/1988 |
| JP | 63280911 A | 11/1998 |
| JP | 2001187064 | 7/2001 |
| JP | 2018509273 | 4/2018 |
| WO | 9639944 A1 | 12/1996 |
| WO | 2016160272 A1 | 10/2016 |
| WO | 2017017443 | 2/2017 |
| WO | 2017151887 A1 | 9/2017 |
| WO | 2019177567 | 9/2019 |
| WO | 2019177569 | 9/2019 |
| WO | 2019177570 | 9/2019 |

OTHER PUBLICATIONS

"International Application Serial No. PCT US2018 022004, Written Opinion dated Feb. 14, 2019", 14 pgs.
"International Application Serial No. PCT US2018 022006, International Search Report dated Feb. 8, 2019", 8 pgs.
"International Application Serial No. PCT US2018 022006, Written Opinion dated Feb. 8, 2019", 15 pgs.
"European Application Serial No. 16773696.6, Extended European Search Report dated Nov. 19, 2018", 8 pgs.
"Anatomical Shoulder Fracture System", Zimmer Surgical Technique, 97-4223-003-00 Rev. 1, (2005), 24 pgs.
"Comprehensive Segmental Revision System, Proximal Humeral Reconstruction, Distal Humeral Reconstruction, Total Humeral Reconstruction", Zimmer Biomet Surgical Technique, 0097.1-US-en-REV0416, (2016), 68 pgs.
"Anatomical Shoulder Glenoid", Zimmer Surgical Technique, (2014), 12 pgs.
"International Application Serial No. PCT US2018 022006, Invitation to Pay Additional Fees dated Dec. 12, 2018", 16 pgs.
"U.S. Appl. No. 15/560,894, Restriction Requirement dated Dec. 31, 2018", 7 pgs.
"International Application Serial No. PCT/US2018/021988, International Search Report dated Dec. 20, 2018", 4 pgs.
"International Application Serial No. PCT/US2018/021988, Written Opinion dated Dec. 20, 2018", 6 pgs.
"International Application Serial No. PCT/US2018/022004, Invitation to Pay Additional Fees dated Dec. 19, 2018", 15 pgs.
"European Application Serial No. 16773696.6, Response filed Jun. 4, 2018 to Office Action dated Nov. 22, 2018".
"U.S. Appl. No. 15/560,894, Response filed Mar. 21, 2019 to Restriction Requirement dated Dec. 31, 2018", 9 pgs.
"European Application Serial No. 18210813.4, Extended European Search Report dated Apr. 12, 2019", 7 pgs.
"U.S. Appl. No. 15/560,894, Non Final Office Action dated May 16, 2019", 9 pgs.
"European Application Serial No. 16773696.6, Response filed Jun. 17, 2019 to Extended European Search Report dated Nov. 19, 2018", 18 pgs.
"Chinese Application Serial No. 201680027778.9, Office Action dated Jul. 12, 2019", w English Translation, 20 pgs.
"U.S. Appl. No. 15/560,894, Response filed Aug. 16, 2019 to Non Final Office Action dated May 16, 2019", 11 pgs.
"Canadian Application Serial No. 3,002,354, Office Action dated Jul. 4, 2019", 4 pgs.
"Unitrac Retraction and holding system for open and minimally invasive surgery", Aesculap Surgical Technologies—Surgical Instruments, (2010), 12 pgs.
"U.S. Appl. No. 15/918,531, Non Final Office Action dated Sep. 26, 2019", 12 pages.
"U.S. Appl. No. 15/919,161, Non Final Office Action dated Sep. 26, 2019", 18 pages.
"U.S. Appl. No. 29/640,121, Notice of Allowance dated Nov. 5, 2019", 8 pages.
"Chinese Application Serial No. 201680027778.9, Response filed Oct. 31, 2019 to Office Action dated Jul. 12, 2019", (with English Claims), 15 pages.
"U.S. Appl. No. 15/560,894, Final Office Action dated Nov. 29, 2019", 8 pages.
"Japanese Application U.S. Appl. No. 2018-501138, Notification of Reasons for Refusal dated Nov. 5, 2019", (with English Translation), 15 pages.
"3840 Series Holder", Fisso—Rail-mounted instrument holding arm / articulated, [Online]. [Accessed Oct. 16, 2017]. Retrieved from the Internet: <URL: http://www.medicalexpo.com/prod/fisso/product-67723-681104.html>, 3 pgs.
"3D-Arm™", Elekta—Minimally invasive surgery instrument holding arm, [Online]. [Accessed Oct. 16, 2017]. Retrieved from the Internet: <URL: http://www.medicalexpo.com/prod/elekta/product-70692-509376.html>, 8 pgs.
"ALLY Uterine Positioning System", Cooper Surgical, [Online]. [Accessed Oct. 16, 2017]. Retrieved from the Internet: <URL: https://www.coopersurgical.com/Products/Detail/ALLY-Uterine-Positioning-System>, 2 pgs.
"U.S. Appl. No. 15/560,894, Preliminary Amendment filed Sep. 22, 2017", 7 pgs.
"U.S. Appl. No. 15/560,894, Supplemental Preliminary Amendment filed Sep. 29, 2017", 7 pgs.

(56) References Cited

OTHER PUBLICATIONS

"ASSISTO Arm System", Geomed Gmbh, [Online]. [Accessed Oct. 16, 2017]. Retrieved from the Internet: <Url: http://www.geomed.de/index.php?id=65&L=1>, 1 pg.

"Atlas™ Flex Arm System", Axcess Surgical, [Online]. [Accessed Oct. 16, 2017]. Retrieved from the Internet: <URL: http://www.axcesssurgical.com/axcess-surgical-innovations-products/atlas-flex-arm-system/>, 5 pgs.

"Atlas™ Rigid Arm System", Axcess Surgical, [Online]. [Accessed Oct. 16, 2017]. Retrieved from the Internet: <URL: http://www.axcesssurgical.com/axcess-surgical-innovations-products/atlas-rigid-arm-system/>, 6 pgs.

"Bookler® StrongArm™ Holder", Mediflex, [Online]. [Accessed Nov. 2, 2017]. Retrieved from the Internet: <URL: http://www.mediflex.com/product/bookler-strongarm-holder-and-positioner-set-12-30cm-post/>, (2015), 4 pgs.

"EndoArm", Olympus, [Online]. [Accessed Nov. 2, 2017]. Retrieved from the Internet: <URL: https://www.olympus.co.jp/jp/news/2003b/nr030925endoj.html>, (Sep. 25, 2003), 4 pgs.

"EndoBoy", LUT-Pneumatic Arm, Grecco, 8 pgs.

"EndoCrane", Karl Storz—LEROY Retractors for Laparoscopic Colorectal Surgery, [Online]. [Accessed Oct. 16, 2017]. Retrieved from the Internet: <URL: https://www.karlstorz.com/cps/rde/xbcr/karlstorz_assets/ASSETS/2193800.pdf>, 16 pgs.

"Genzyme Remote Surgical Retractor Arm Hands Free Pneumatic System", Renix International/Alibaba.com Copyright 1999-2017, [Online]. [Accessed Nov. 2, 2017]. Retrieved from the Internet: <URL: http://renix.trustpass.alibaba.com/product/50001078652-219532304/Genzyme_Remote_Surgical_Retractor_Arm_Hands_Free_Pneumatic_System.html>, 2 pgs.

"Helping Hand", Fraunhofer IPA—The helping hand in the operation room Research News, [Online]. [Accessed Oct. 16, 2017]. Retrieved from the Internet: <URL: https://www.fraunhofer.de/en/press/research-news/2015/november/helping-hand-in-the-operation-room.html>, (Nov. 2015), 2 pgs.

"International Application Serial No. PCT/US2016/021076, International Preliminary Report on Patentability dated oct. 12, 2017", 11 pgs.

"International Application Serial No. PCT/US2016/021076, International Search Report dated Aug. 11, 2016", 4 pgs.

"International Application Serial No. PCT/US2016/021076, Invitation to Pay Add'l Fees and Partial Search Report dated May 25, 2016", 2 pgs.

"International Application Serial No. PCT/US2016/021076, Written Opinion dated Aug. 11, 2016", 8 pgs.

"IronIntern", Automated Medical, [Online]. [Accessed Oct. 16, 2017]. Retrieved from the Internet: <URL: http://ironintern.com/iron-intern%E2%84%A2>, 1 pg.

"Jarit Endoscope Holder", Integra, [Online]. [Accessed Oct. 16, 2017]. Retrieved from: <URL: https://www.integralife.com/endoscope-instrument-holder-set/product/surgical-instruments-hospitals-surgery-centers-tissue-banks-jarit-laparoscopic-endoscopes-endoscope-instrument-holder-set>, 18 pgs.

"M-Trac", Aesculap / B Braun, [Online]. [Accessed—Oct. 16, 2017]. Retrieved from the Internet: <URL: https://www.bbraun.com/en/products/b/m-trac.html>, 2 pgs.

"Martin's Arm", Hayden Medical (& others), [Online]. [Accessed Oct. 16, 2017]. Retrieved from the Internet: <URL: http://haydenmedical.com/surgical-retractors-martins-arm-retractors/>, 2 pgs.

"Mechanical Arm—Mod. 8470", Ansabere Surgical, [Online]. [Accessed Oct. 16, 2017]. Retrieved from the Internet: <URL: http://www.ansaberesurgical.com/en/productos/brazos-mecanicos/brazo-mecanico-mod-8470/>, 5 pgs.

"Phantom ML", TeDan Surgical Innovations, [Online]. [Accessed Nov. 14, 2017]. Retrieved from the Internet: <URL: http://www.tedansurgical.com/spine/articulating-arms/>, 2 pgs.

"Point Setter", Mitaka Kohki Co., Ltd. Operating / User's Manual Model: PSMS2, (Feb. 14, 2010), 28 pgs.

"PositionOR", Surgical Concept Designs, [Online]. [Acessed Nov. 14, 2017]. Retrieved from the Internet: <URL: http://surgical-concepts.com/products/PositionOR/>, 1 pg.

"Postioning Arm", Civco—Laparostat™ Kit, [Online]. [Accessed Oct. 16, 2017]. Retrieved from the Internet: <URL: http://www.civco.com/mmi/resources/ifu/043687.pdf>, 16 pgs.

"SaphLITE | RadLITE", Teleflex Medical, [Online]. [Accessed Nov. 14, 2017]. Retrieved from the Internet: <URL: https://www.teleflex.com/en/usa/prod_saphlite-radlite.php>, 1 pg.

"Saphlite/Saphlift", Genzyme Surgical Products (Jan. 7, 1999), [Online]. [Accessed Oct. 16, 2017]. Retrieved from the Internet: <URL: https://www.accessdata.fda.gov/cdrh_docs/pdf/K990062.pdf>, 5 pgs.

"Speed-Tract", Integra—Table Mounted Speed-Tract Retractor System, [Online]. [Accessedd Oct. 16, 2017]. Retrieved from the Internet: <URL: http://occ.integralife.com/products%2Fpdfs%2Fintegra%20table%20mounted%20speed-tract%20retractor%20system%20brochure.pdf>, 6 pgs.

"Spider2 Limb Positioner", Smith & Nephew, [Online]. [Accessed Nov. 14, 2017]. Retrieved from the Internet: <URL: http://www.smith-nephew.com/new-zealand/advanced-surgical-devices/key-products/sports-medicine/spider2-limb-positioner-for-shoulder--hip--knee--/>, 2 pgs.

"Spine Endoscope & Endoscope Holder", Maxer, [Online]. [Accessed Nov. 2, 2017]. Retrieved from the Internet: <URL: http://www.maxerendoscopy.com/index.php?option=com_content&view=article&id=190:spine-endoscope-endoscope-holder&catid=81:spine-endoscopy&Itemid=858>, (2013).

"SurgiAssist Camera Holder", SurgiToolsMIS, [Online]. [Acessed Nov. 14, 2017]. Retrieved from the Internet: <URL: https://www.surgitools.com/surgiassist-camera-holder.html>, 4 pgs.

"Synaptive BrightMatter Drive Robotic Surgical Video Arm System", Synaptive, [Online]. [Accessed Nov. 14, 2017]. Retrieved from the Internet: <URL: https://www.medgadget.com/2016/05/synaptive-brightmatter-drive-robotic-surgical-videoarm-system.html>, 3 pgs.

"Tee Transducer Holder", Civco, [Online]. [Accessed Oct. 16, 2017]. Retrieved from the Internet: <URL: http://www.civco.com/mmi/resources/product-support/TEE-Holder-Brochure_2008P-2339-Rev-2_low-res-8I9rv5.pdf>, 8 pgs.

"The Freehand System", Freehand—V1.2, [Online]. [Acessed Oct. 16, 2017]. Retrieved from the Internet: <URL: http://freehandsurgeon.com/Products/Detail?id=2>, 3 pgs.

"TiREX® Retractor System", Orion Surgical, [Online]. [Accessed Nov. 2, 2017]. Retrieved from the Internet: <URL: http://www.orion-surgical.com/english/tirex-retractor-system/components-of-the-tirex.html>, (2017), 2 pgs.

"Trimano 3D Support Arm", Maquet, [Online]. [Accessed Oct. 16, 2017]. Retrieved from the Internet: <URL: https://www.maquet.com/int/products/trimano-3d-support-arm/>, 3 pgs.

"UniARM Surgical Support System", Mitaka Kohki Co., Ltd. Operating / User Manual Version 1.1, [Online]. [Accessed Nov. 2, 2017]. Retrieved from the Internet: <URL: http://mitakausa.com/uniarm/>, (Mar. 20, 2009), 19 pgs.

"Unitrac® Pneumatic Holding Arm", Aesculap / B Braun, [Online]. [Accessed Oct. 16, 2017]. Retrieved from the Internet: <URL: https://www.bbraun.com/en/products/b/unitrac-pneumaticholdingarm.html>, 3 pgs.

"Vertek Articulating Arm", Medtronic—Copyright 2013, [Online]. [Accessed Nov. 2, 2017]. Retrieved from the Internet: <URL: http://global.medtronic.com/xg-en/healthcare-professionals/products/neurological/surgical-navigation-imaging/neurosurgery-imaging-surgical-navigation/surgical-procedures.html>, 2 pgs.

"Viky", Endocontrol Medical, [Online]. [Accessed 2014]. Retrieved from the Internet: <URL: http://www.endocontrol-medical.com/en/viky-en/>, 5 pgs.

"Wingman Scope Holder", Stryker, [Online]. [Accessed Nov. 14, 2017]. Retrieved from the Internet: <URL: http://www.stryker.com/cn/products/OREquipmentTelemedicine/EndoscopicSurgeryEquipment/Laparoscopy/Accessories/ScopeHolder/index.htm#>, 3 pgs.

"Canadian Application Serial No. 3,002,354, Response filed Dec. 20, 2019 to Office Action dated Jul. 4, 2019", 14 pages.

(56) References Cited

OTHER PUBLICATIONS

"Chinese Application Serial No. 201680027778.9, Office Action dated Feb. 6, 2020", with English translation, 6 pages.
"U.S. Appl. No. 15/918,531, Response filed Dec. 26, 2019 to Non Final Office Action dated Sep. 26, 2019", 12 pages.
"U.S. Appl. No. 15/919,161, Response filed Dec. 26, 2019 to Non Final Office Action dated Sep. 26, 2019", 13 pages.
"U.S. Appl. No. 15/919,161, Final Office Action dated Feb. 19, 2020", 7 pages.
"U.S. Appl. No. 29/640,121, Corrected Notice of Allowability dated Jan. 21, 2020", 4 pages.
"U.S. Appl. No. 15/560,894, Response filed Jan. 28, 2020 to Final Office Action dated Nov. 29, 2019", 7 pages.
"U.S. Appl. No. 15/560,894, Notice of Allowance dated Feb. 13, 2020", 8 pages.
"U.S. Appl. No. 15/918,531, Notice of Allowance dated Feb. 19, 2020", 11 pages.
"U.S. Appl. No. 16/210,787, Restriction Requirement dated Apr. 16, 2020", 5 pages.
"Australian Application Serial No. 2016243292, First Examination Report dated Apr. 7, 2020", 4 pages.
"Chinese Application U.S. Appl. No. 201680027778.9, Office Action dated Jun. 12, 2020", with English translation, 18 pages.
"Chinese Application U.S. Appl. No. 201680027778.9, Response filed Jul. 15, 2020 to Office Action dated Jun. 12, 2020", with English claims, 71 pages.

* cited by examiner

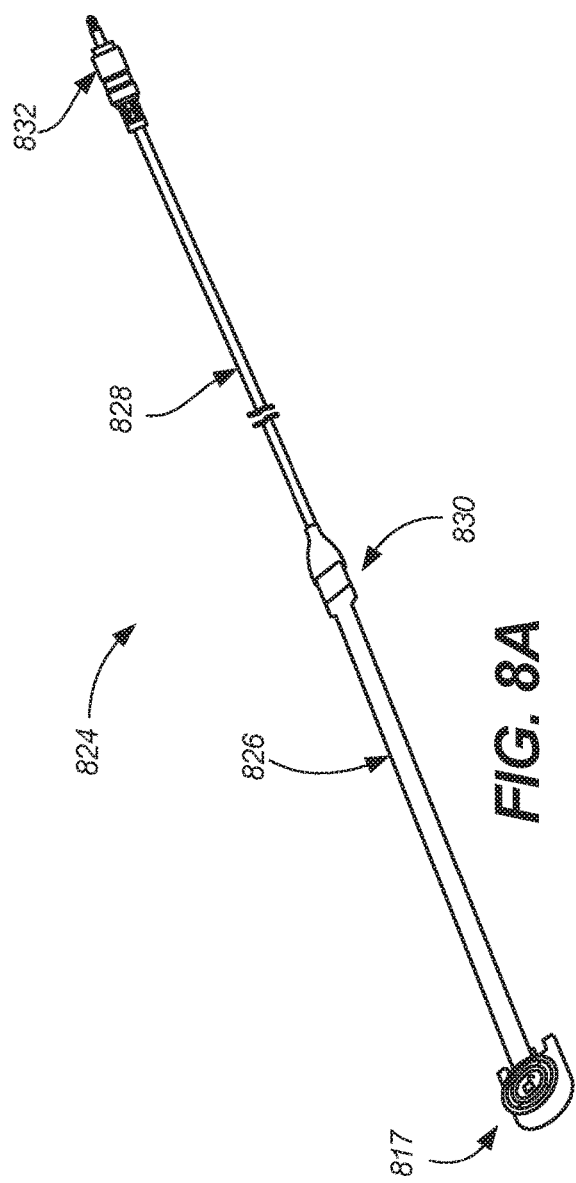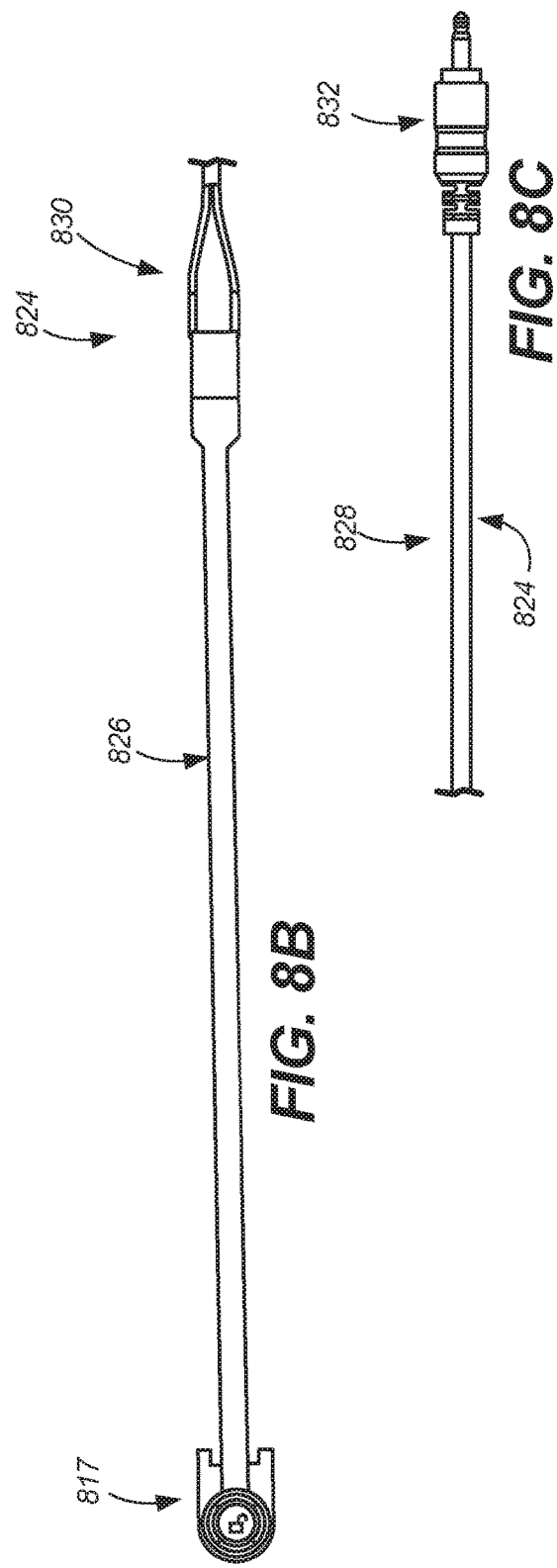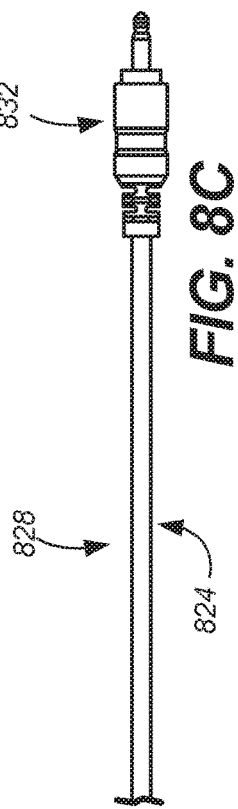

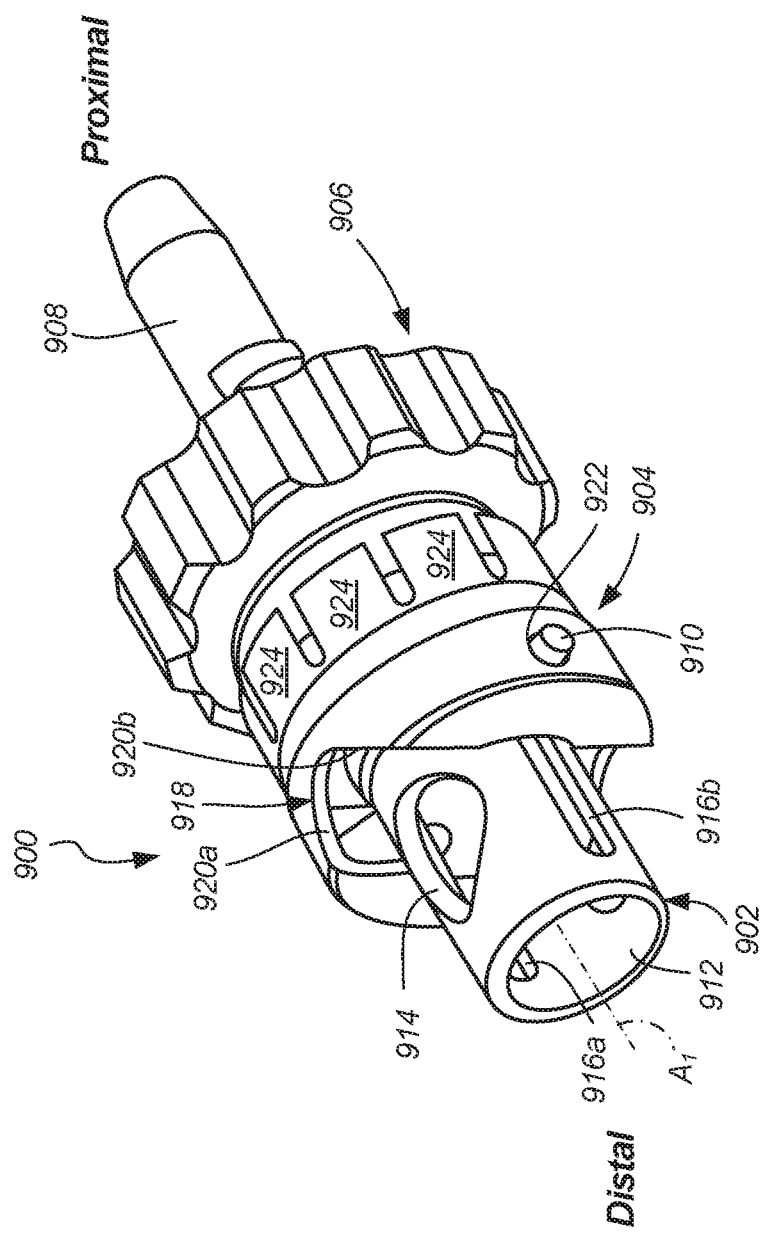

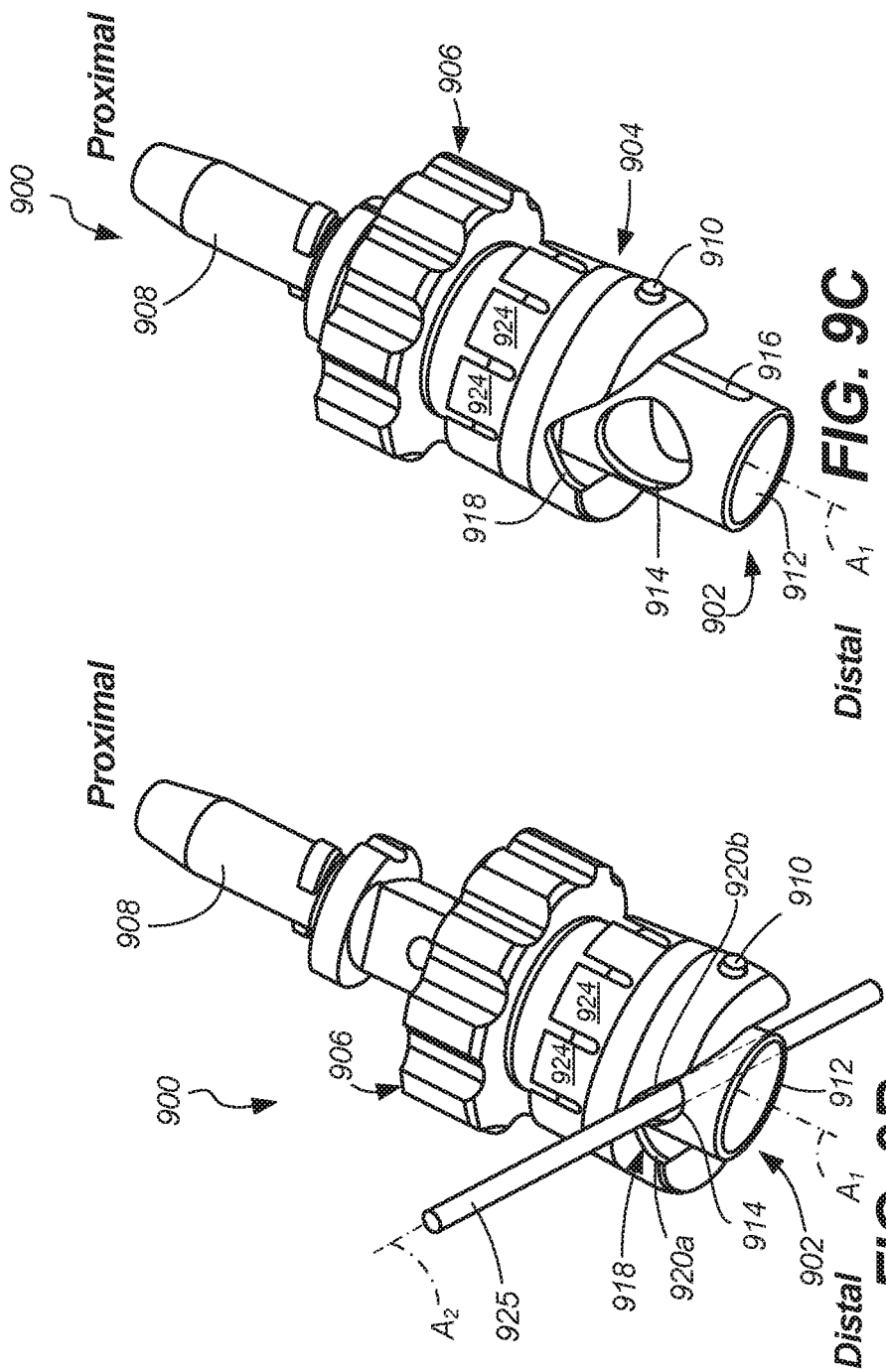

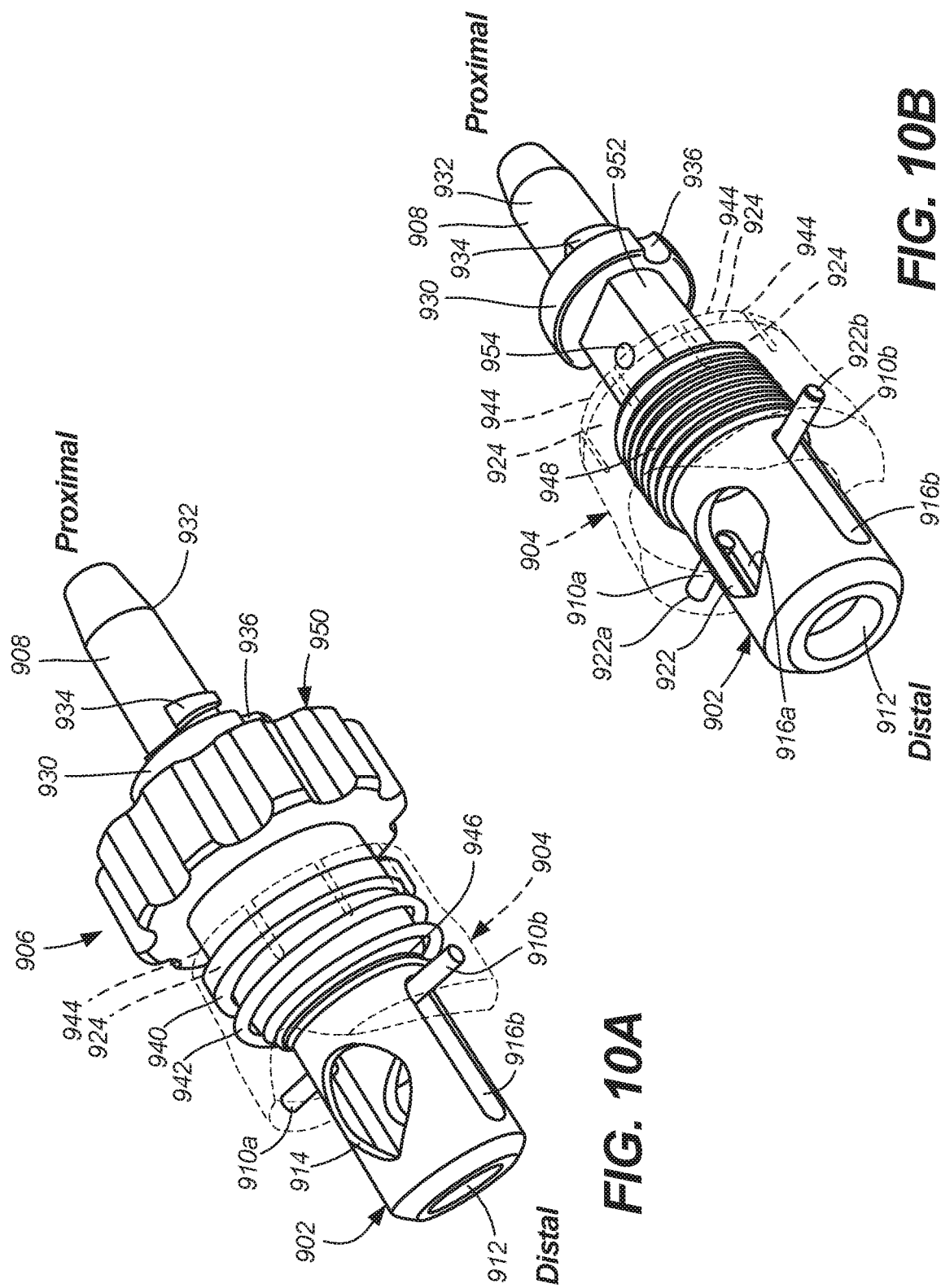

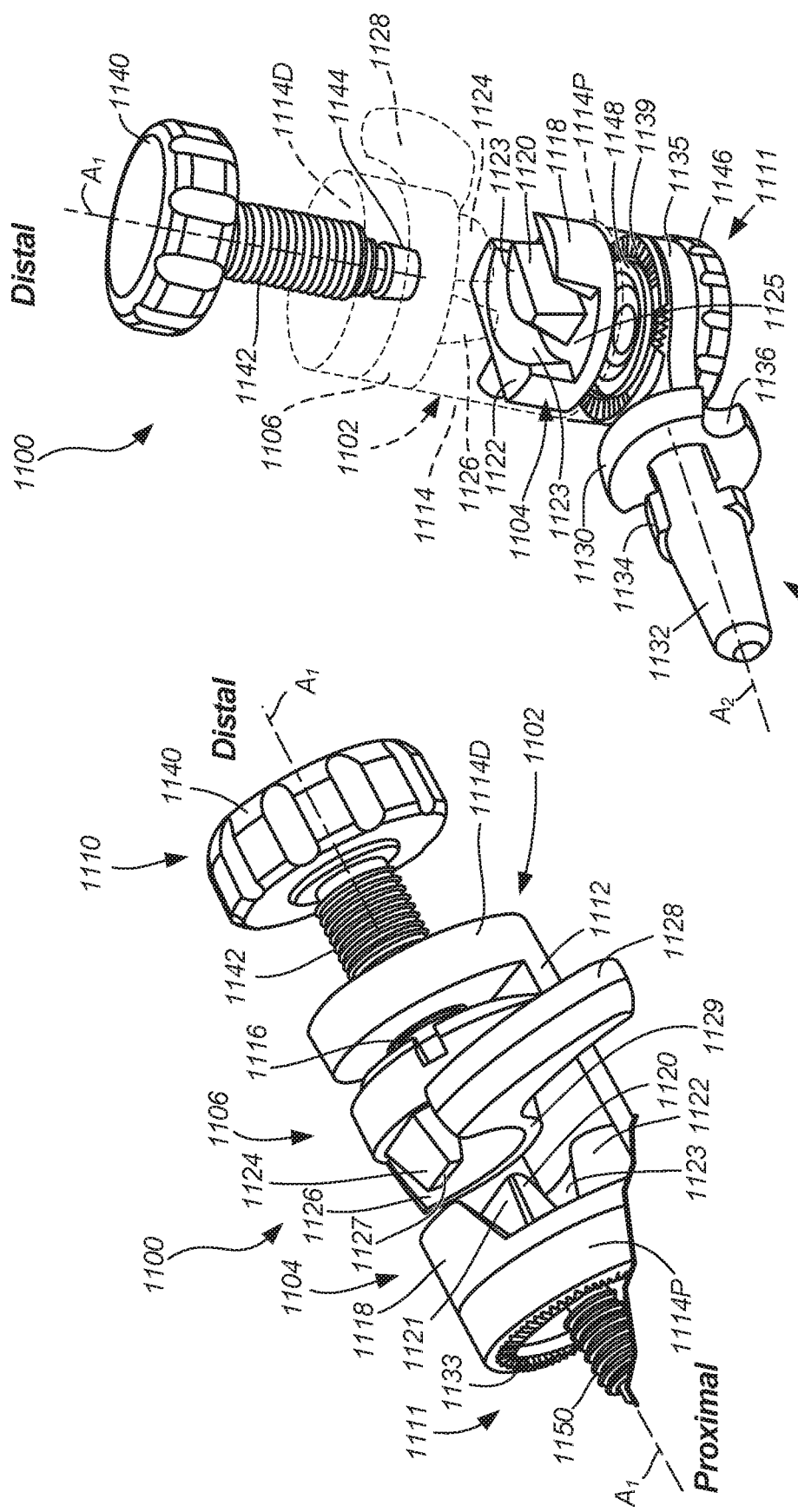

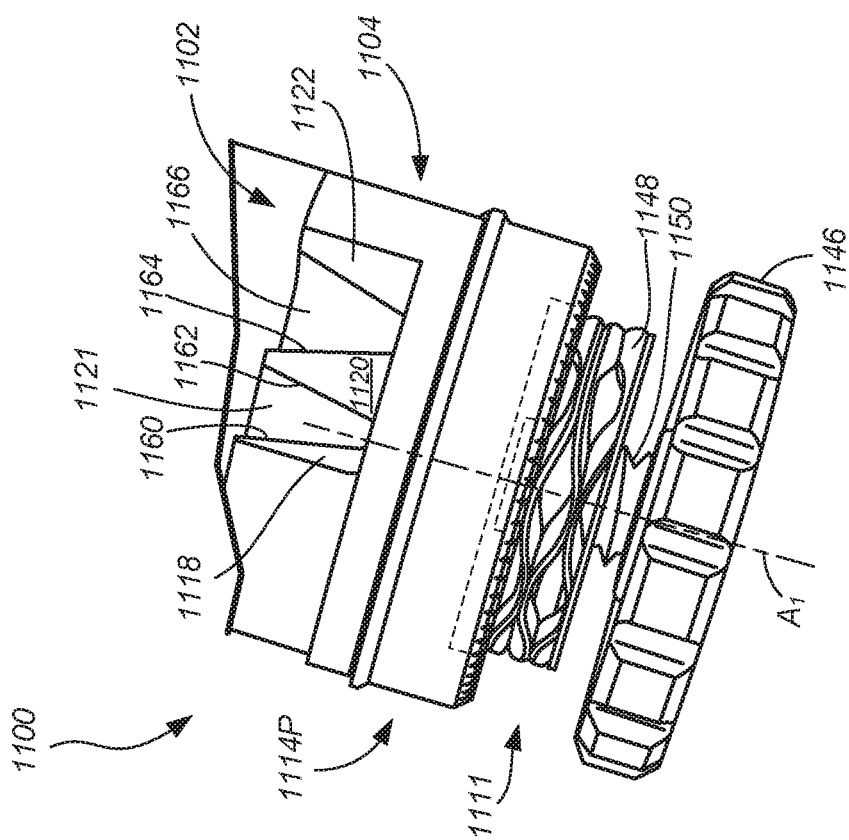

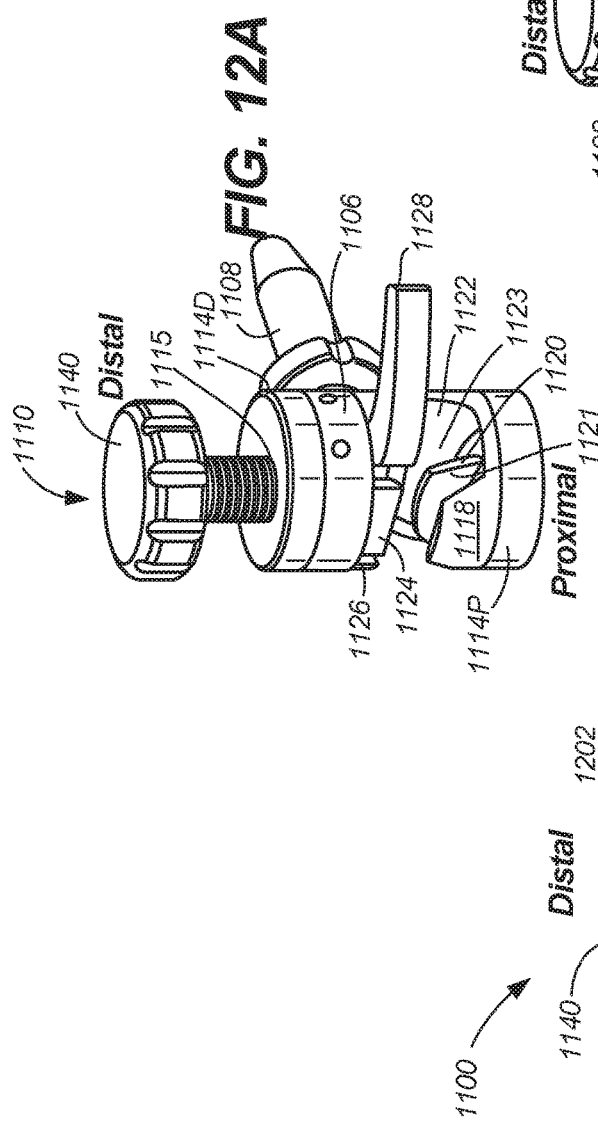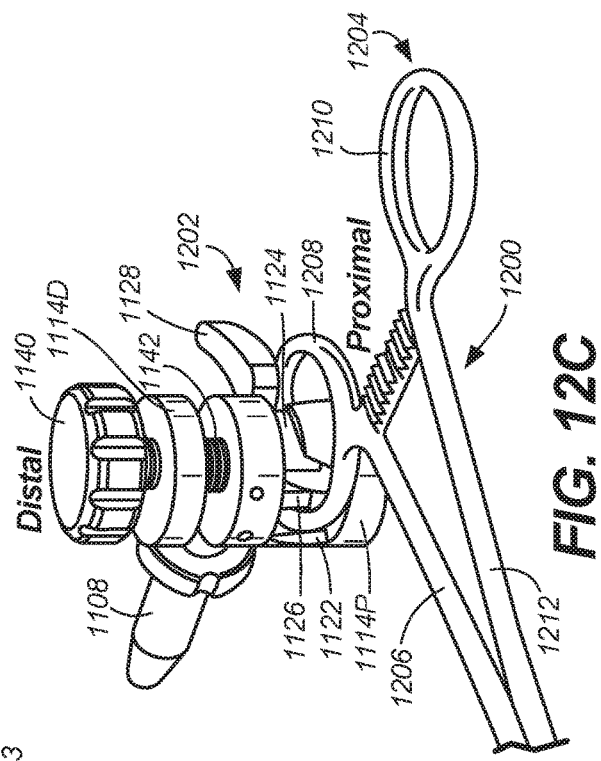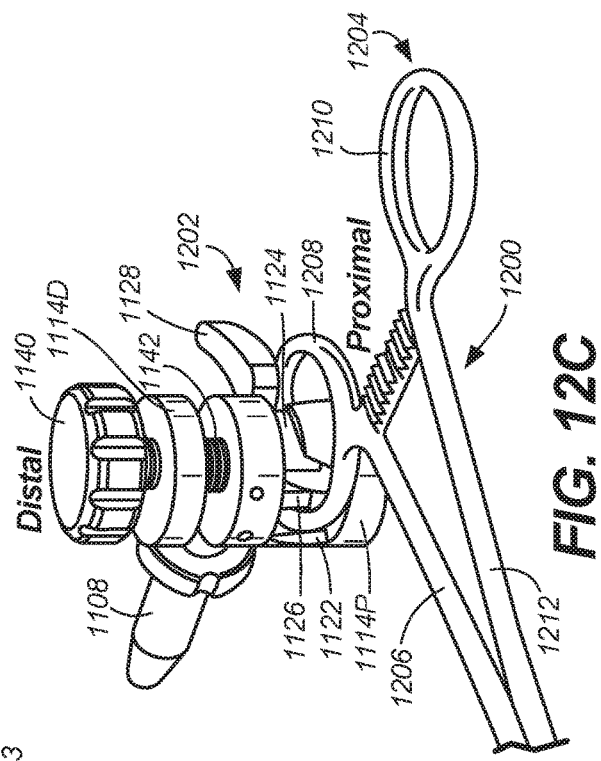

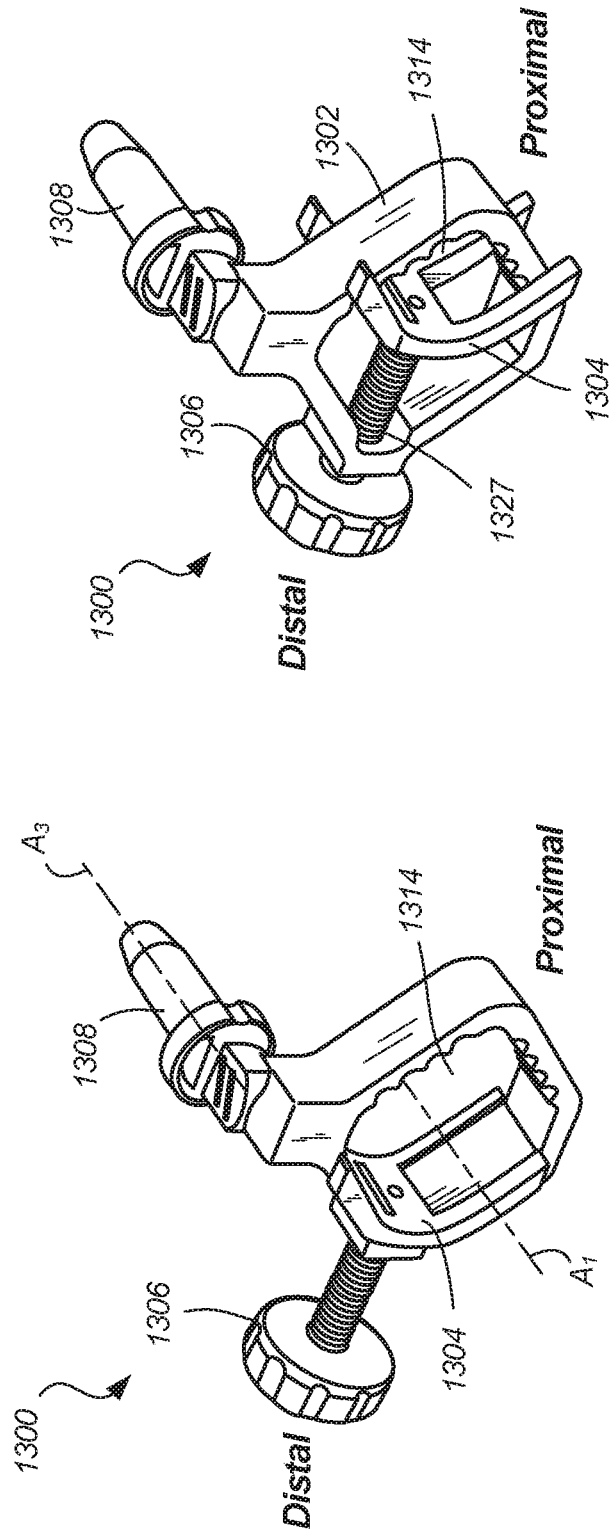

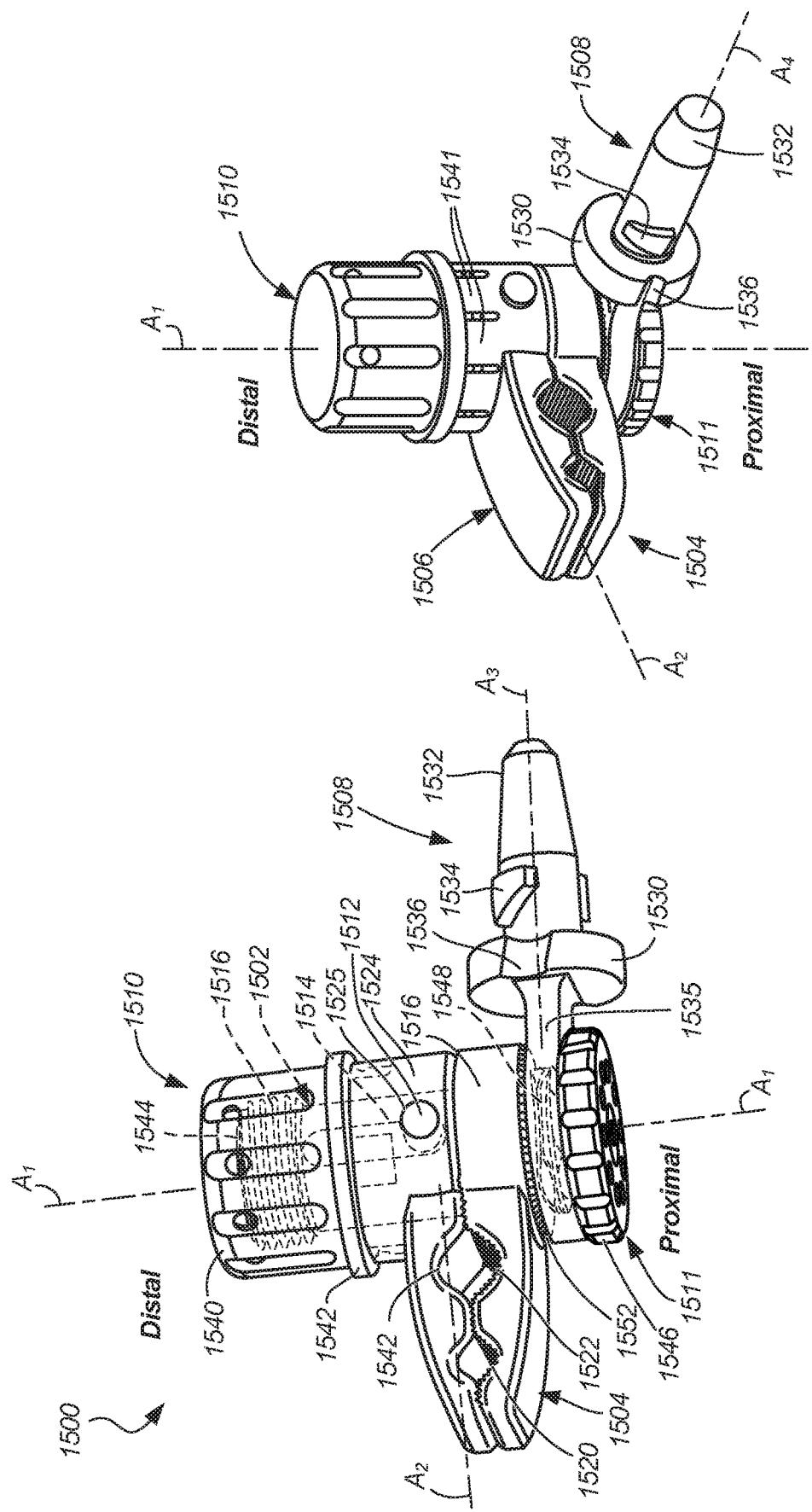

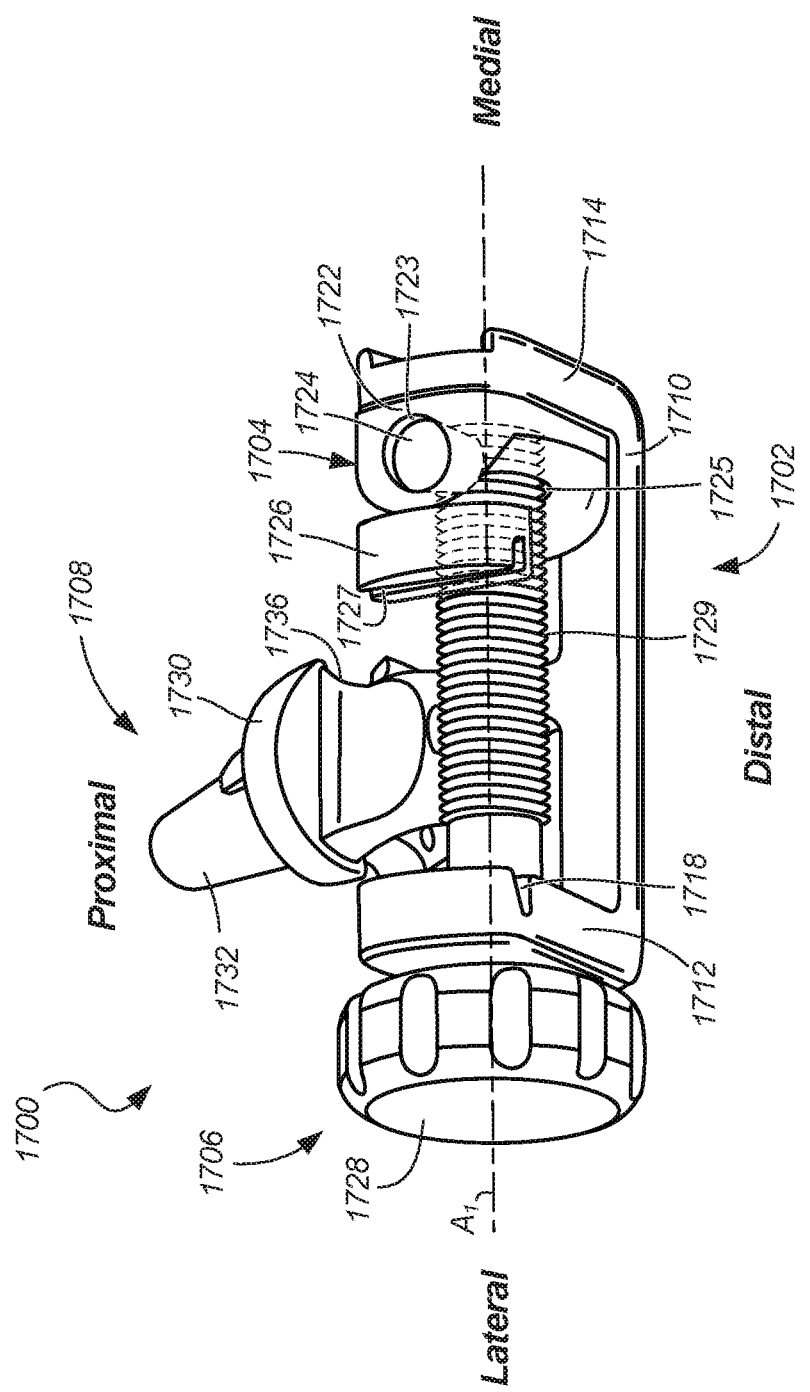

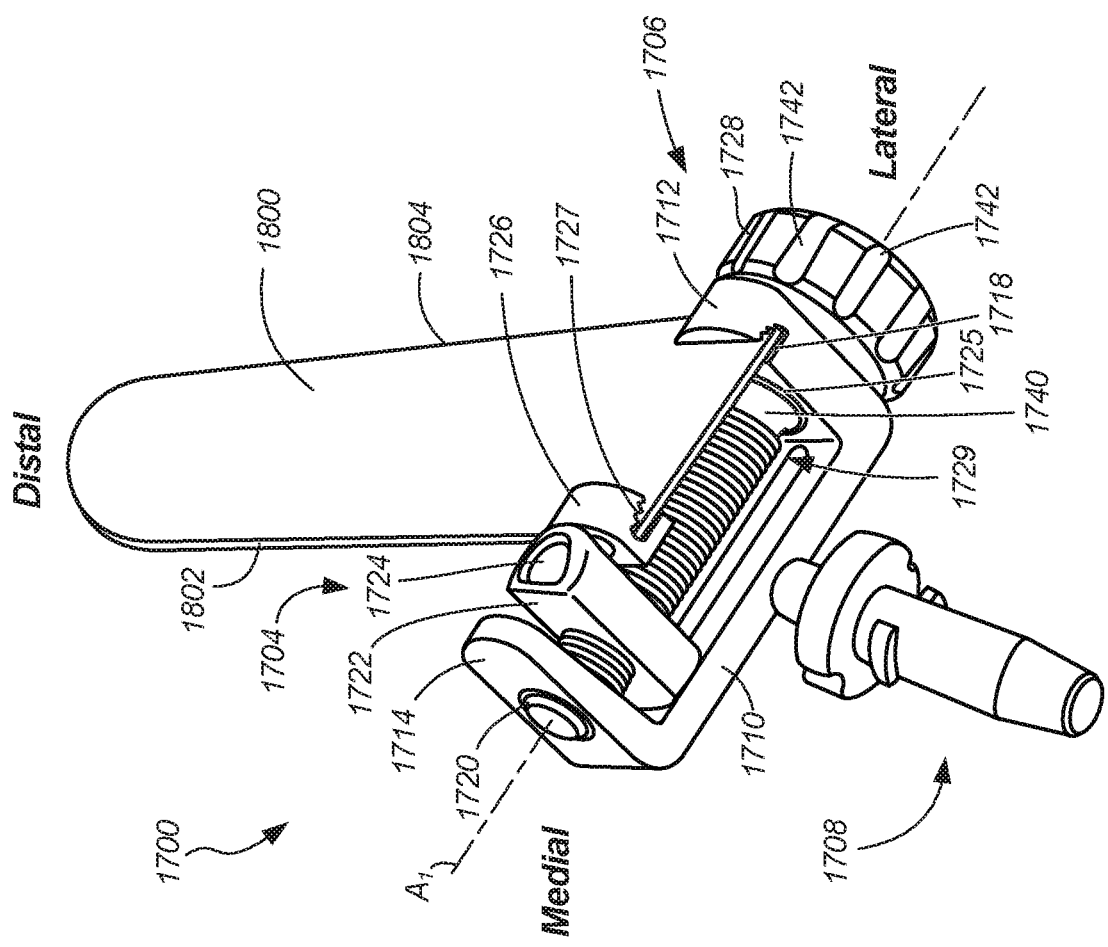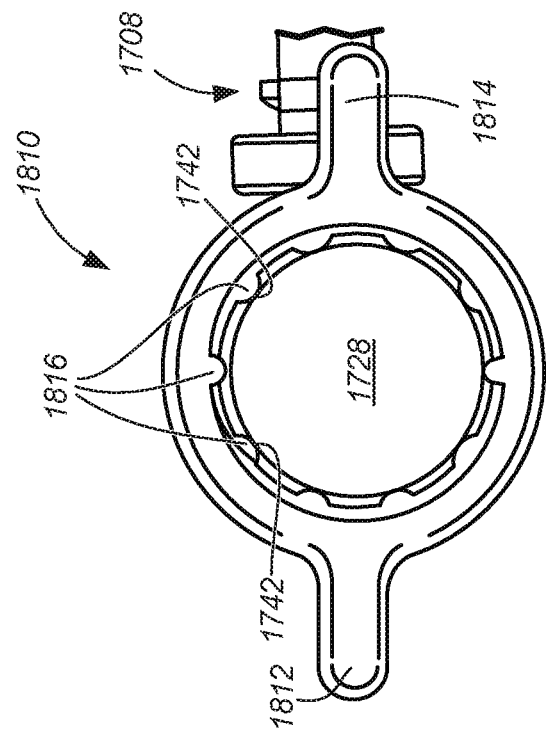
FIG. 18A
FIG. 18B

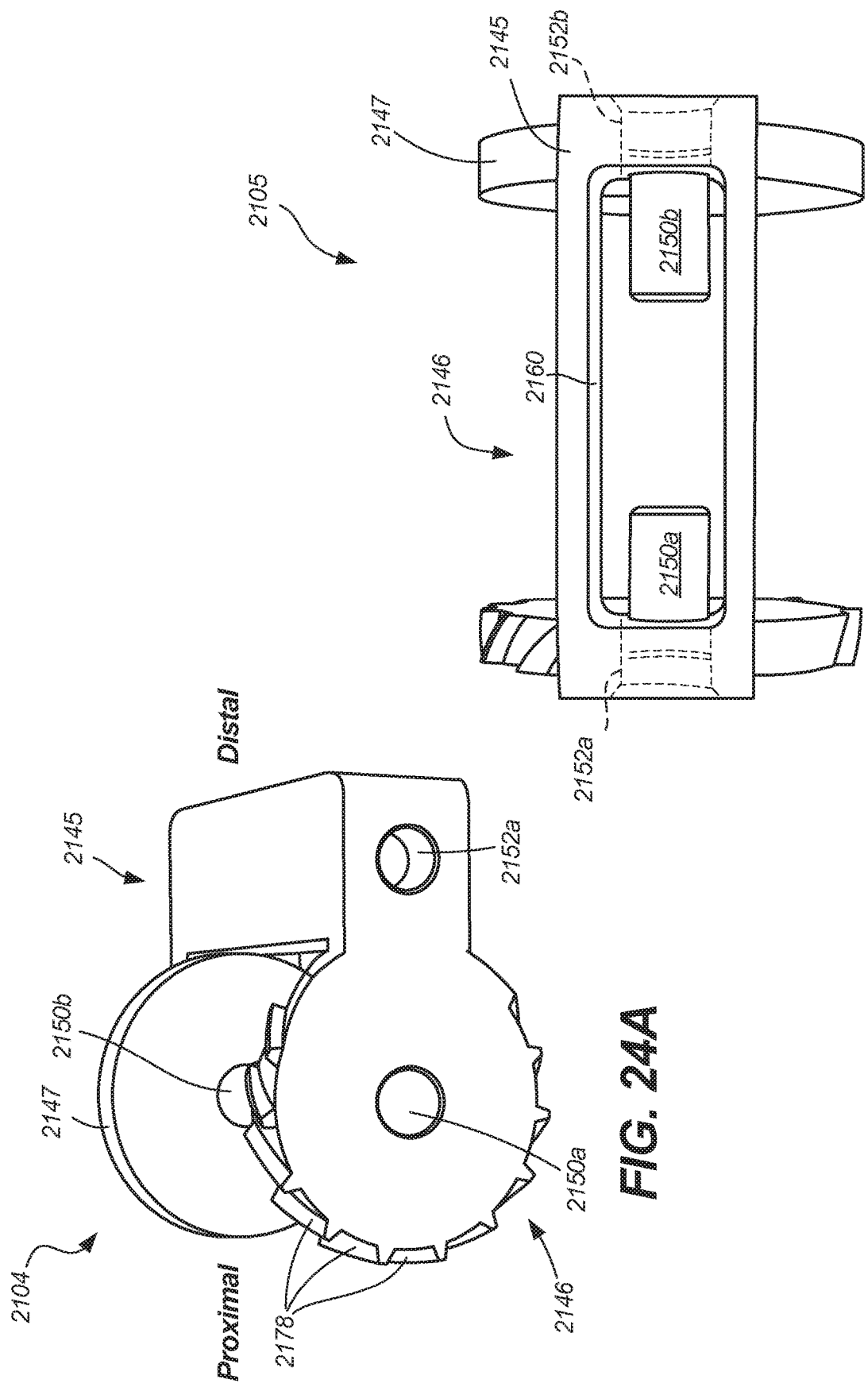

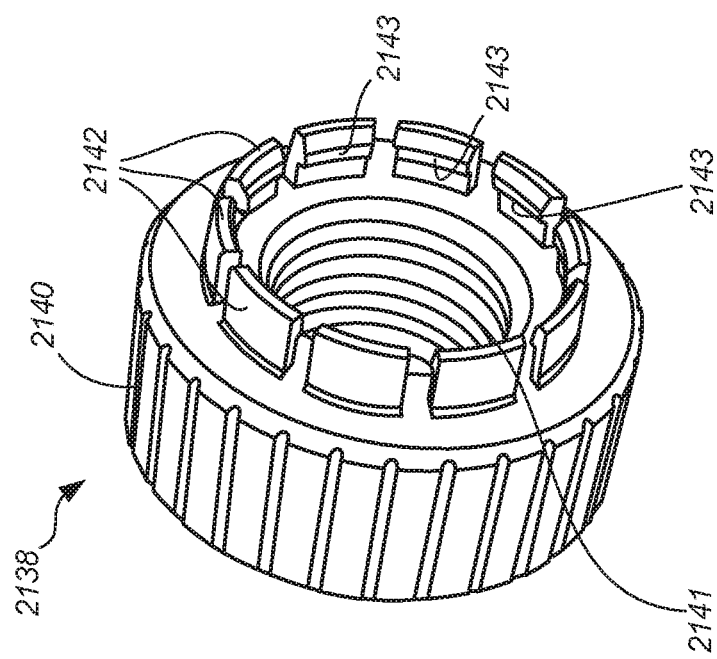
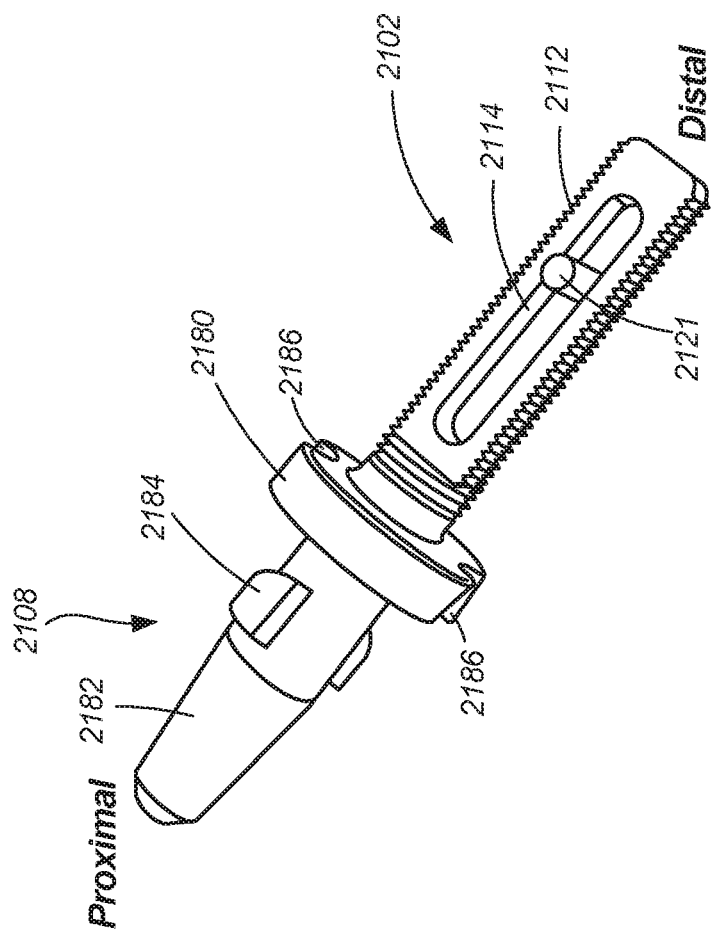
FIG. 25B
FIG. 25A

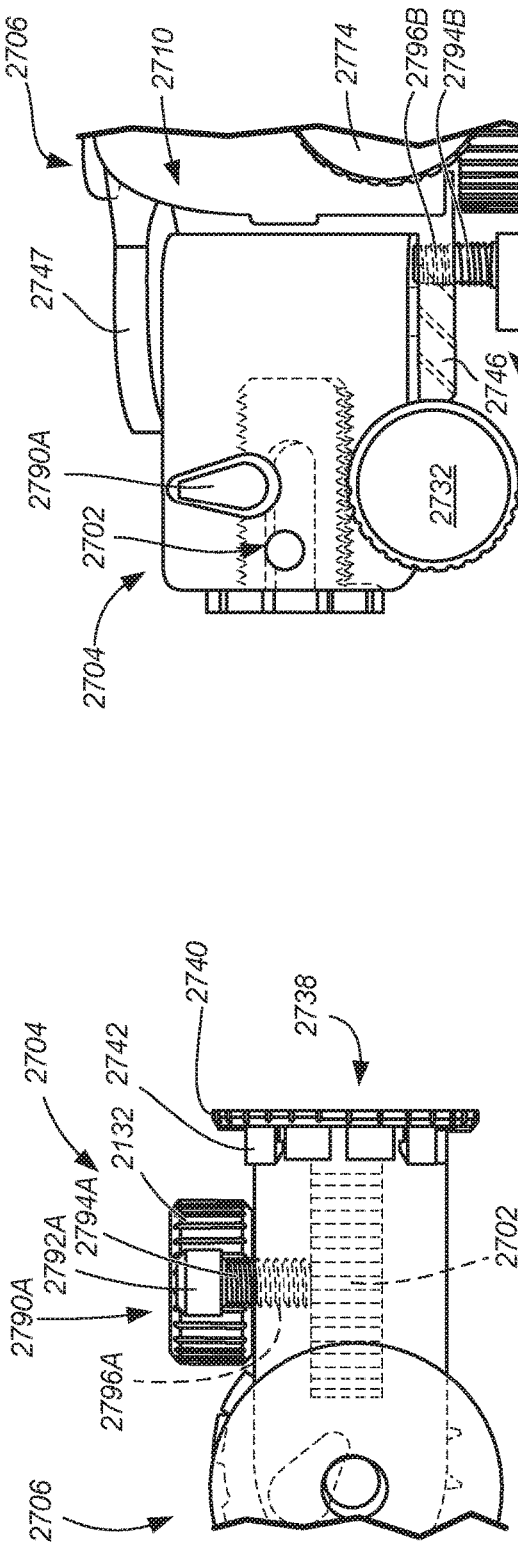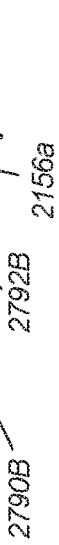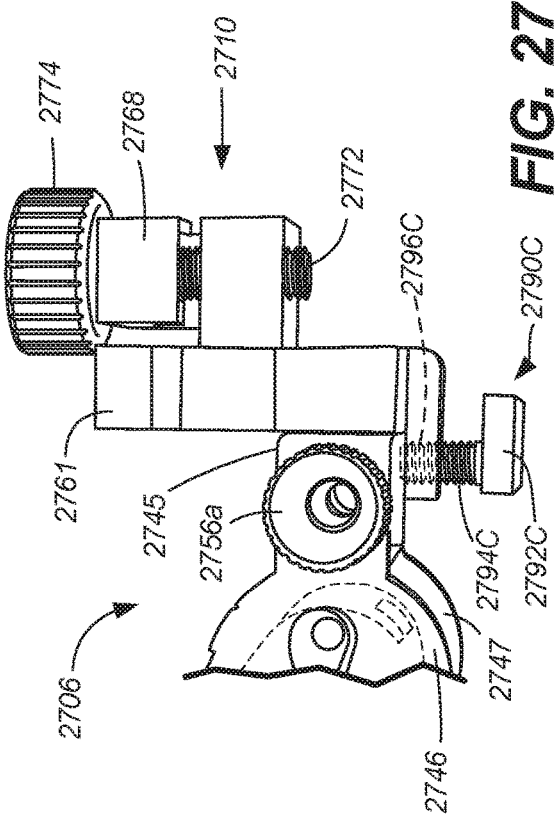

END EFFECTOR COUPLER FOR SURGICAL ARM

CROSS-REFERENCE TO RELATED PATENT DOCUMENTS

This patent application is also related to Jeffrey Schlosser et al., U.S. patent application Ser. No. 15/560,894 entitled "Rapidly Repositionable Powered Support Arm," filed on Sep. 22, 2017 which is incorporated by reference herein in its entirety.

BACKGROUND

The present invention relates generally to apparatus and systems for supporting surgical and other instruments. Some surgical procedures include use of a variety of instruments. In some of these procedures, it is required that instruments, such as a retractor, be maintained in a single position for an extended period of time, such as an hour or more. During this time, other instruments can be used to perform other aspects of the surgery. Because it may be difficult or undesirable to manually hold a position of an instrument for such lengths of time, mechanical and/or electromechanical arms can be used to hold the position of the instrument while other aspects of the procedure are performed. Some arms can be adjustable such that a position of the arm can be adjusted before or during the procedure.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 8A illustrates a perspective view of a cable, in accordance with at least one example of this disclosure.

FIG. 8B illustrates a perspective view of a portion of a cable, in accordance with at least one example of this disclosure.

FIG. 8C illustrates a perspective view of a portion of a cable, in accordance with at least one example of this disclosure.

FIG. 9A illustrates a perspective view of an instrument holder, in accordance with at least one example of this disclosure.

FIG. 9B illustrates a perspective view of an instrument holder in a first condition, in accordance with at least one example of this disclosure.

FIG. 9C illustrates a perspective view of an instrument holder in a second condition, in accordance with at least one example of this disclosure.

FIG. 10A illustrates a perspective view of an instrument holder, in accordance with at least one example of this disclosure.

FIG. 10B illustrates a perspective view of an instrument holder, in accordance with at least one example of this disclosure.

FIG. 11A illustrates a perspective view of an instrument holder, in accordance with at least one example of this disclosure.

FIG. 11B illustrates a perspective view of an instrument holder, in accordance with at least one example of this disclosure.

FIG. 11C illustrates a focused perspective view of a portion of an instrument holder, in accordance with at least one example of this disclosure.

FIG. 12A illustrates a perspective view of an instrument holder, in accordance with at least one example of this disclosure.

FIG. 12B illustrates a perspective view of an instrument holder and an instrument, in accordance with at least one example of this disclosure.

FIG. 12C illustrates a perspective view of an instrument holder and an instrument, in accordance with at least one example of this disclosure.

FIG. 14A illustrates a perspective view of an instrument holder in a first condition, in accordance with at least one example of this disclosure.

FIG. 14B illustrates a perspective view of an instrument holder in a second condition, in accordance with at least one example of this disclosure.

FIG. 16B illustrates a perspective view of an instrument holder, in accordance with at least one example of this disclosure.

FIG. 16C illustrates a perspective view of an instrument holder, in accordance with at least one example of this disclosure.

FIG. 17C illustrates a perspective view of an instrument holder, in accordance with at least one example of this disclosure.

FIG. 18A illustrates a perspective view of an instrument holder, in accordance with at least one example of this disclosure.

FIG. 18B illustrates a perspective view of an instrument holder, in accordance with at least one example of this disclosure.

FIG. 24A illustrates a perspective view of a portion of an instrument holder, in accordance with at least one example of this disclosure.

FIG. 24B illustrates a perspective view of a portion of an instrument holder, in accordance with at least one example of this disclosure.

FIG. 25A illustrates a perspective view of a portion of an instrument holder, in accordance with at least one example of this disclosure.

FIG. 25B illustrates a perspective view of a portion of an instrument holder, in accordance with at least one example of this disclosure.

FIG. 27A illustrates a perspective view of a portion of an instrument holder, in accordance with at least one example of this disclosure.

FIG. 27B illustrates a perspective view of a portion of an instrument holder, in accordance with at least one example of this disclosure.

FIG. 27C illustrates a perspective view of a portion of an instrument holder, in accordance with at least one example of this disclosure.

DETAILED DESCRIPTION

Figure 1:
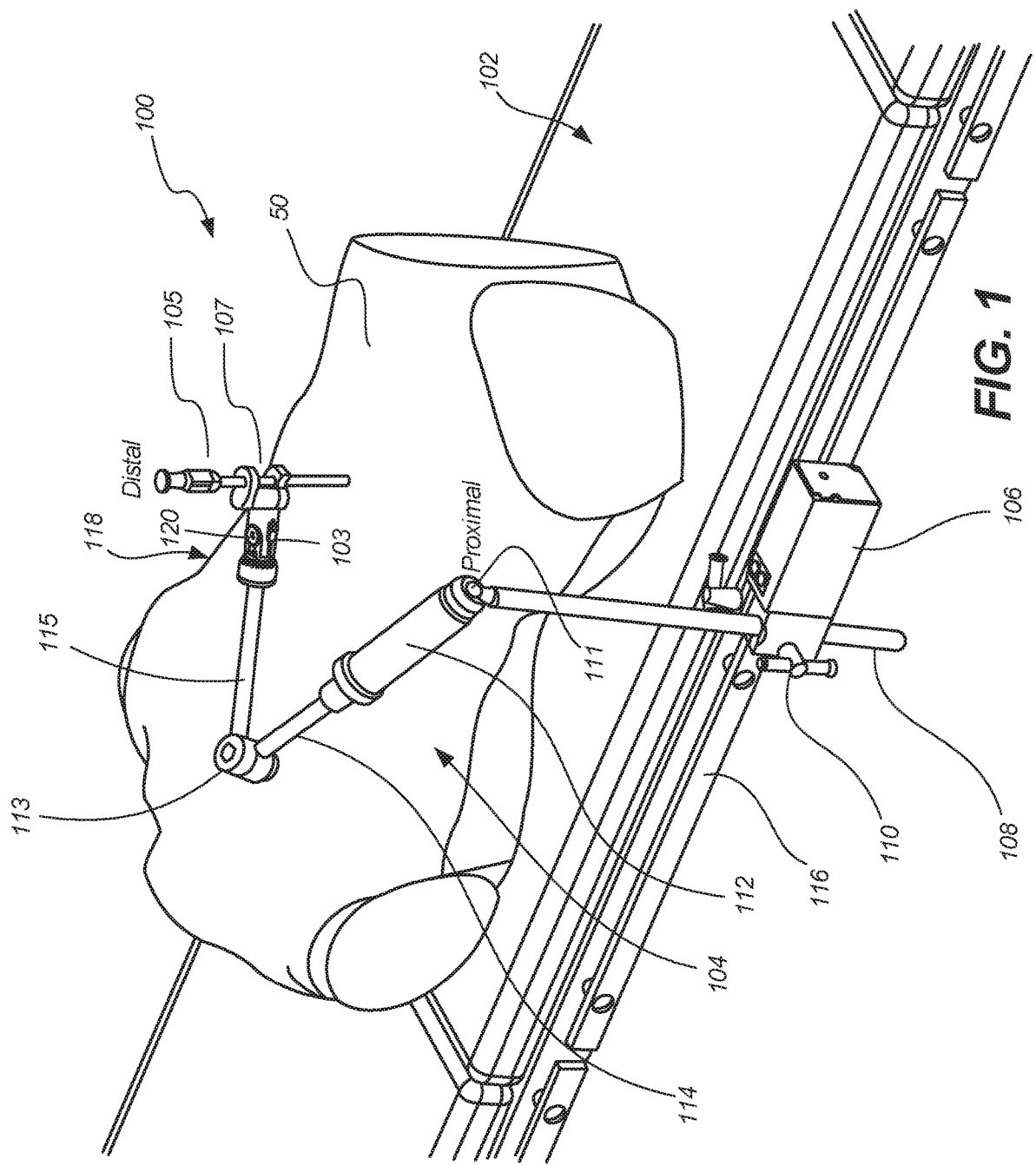
FIG. 1 illustrates a perspective view of a repositionable, lockable surgical arm system, in accordance with at least one example of this disclosure.

Some surgical procedures require a variety of instruments. In some cases, it is desired to hold instruments, such as a retractor, in a single position for an extended period of time, such as an hour or more. In these procedures, adjustable mechanical and/or electromechanical arms are often used to hold the position of the instrument while other aspects of the procedure are performed. One type of arm sometimes employed is an arm that is manually articulable when unlocked and is prevented from being moved when locked. Because these arms are made for use with instruments, there is a need to secure instruments to the arm. And, because a single procedure may require multiple instruments and because the arms may be used for various procedures, there is a need for a method of quickly and easily securing a variety of tools to the arm along with a need for various instruments securable to the arm.

This disclosure provides a solution to these issues through the use of an end effector coupler and various tools coupleable thereto. The coupler can be releasably or fixedly secured to the arm and can include components allowing for tools to be released quickly and easily while providing a secure connection between the tool and the arm. More specifically, the end effector coupler can include a tool lock to secure a tool stem within the end effector coupler. As part of the locking engagement between the end effector and the tool, the tool stem and end effector body can interface in a taper-to-taper arrangement to reduce play or relative movement between the end effector coupler and the tool. Similarly, the end effector body and surgical arm can interface in a taper-to-taper arrangement to reduce play or relative movement between the end effector coupler and the surgical arm.

The end effector can also include a keyed opening and a counterbore coaxial with a central bore of the end effector. The tool stem can also include key bits configured to pass through keyways of the keyed opening to ensure alignment with the end effector, where the key bits also engage a surface between the counter bore and the proximal side of the keyed opening as the tool is rotated; this can draw the stem completely within the end effector to secure the tool thereto.

Also, the locking mechanism can include a retractable pin (operable using an actuator), where the pin can extend from the bore to engage a flange of the stem. This locking engagement can prevent unwanted relative rotation of the tool and stem relative to the end effector coupler, helping to limit unwanted release of the tool from the end effector coupler. When it is desired to remove the tool, the pin can be retracted so that the tool and stem can be rotated for removal from the end effector coupler, allowing for quick release of tools from the end effector coupler. These and other features and benefits are discussed with reference to figures in further detail below.

Further, various tools can be coupleable to the end effector through a common stem. The tools can include: a small instrument holder for coupling small instruments to the surgical arm; a large instrument holder for coupling large instruments to the surgical arm; a flat instrument holder; a scope holder, and more. The end effector coupler can help allow for these various tools to be quickly removed and coupled to the surgical arm so that a variety of tools (and instruments retained by the tools) can be positionable using the arm and operated with the arm.

As used herein, the terms "proximal" and "distal" should be given their generally understood anatomical interpretation. The term "proximal" refers to a direction generally toward the torso of a patient or base or handle of a tool or instrument, and "distal" refers to the opposite direction of proximal, i.e., away from the torso of a patient or toward the working end of the tool.

FIG. 1 illustrates a perspective view of repositionable, lockable surgical arm system 100, in accordance with at least one example of this disclosure. Lockable surgical arm system 100 can include table 102, arm 104, instrument 105, base unit 106, and instrument holder 107. Table 102 can include rail 116. Base unit 106 can include pole 108 and manual clamp 110. Arm 104 can include proximal joint 111, actuator unit 112, distal joint 113, proximal arm 114, distal arm 115, and end effector coupler 118, and lock/unlock button 120. Also shown in FIG. 1 are orientation indicators Proximal and Distal (shown and discussed with respect to the adjustable arm).

Base unit 106, which can include power control circuit components for an electrically powered actuator (such as actuator 112), can be secured to rail 116 of surgical table 102 using, for example, a clamp. Manual clamp 110a of base unit 106 can be operated to tighten base unit 106 against railing 116 and manual clamp 110b can be operated for adjustment of pole 108 to set a height of arm 104 above surgical table 102. Instrument holder 107 can be secureable to a distal end of end effector coupler and can be configured to retain various instruments in a fixed (or adjustable) position relative to arm 104.

Electric actuator unit 112 of arm 104 can be located near a proximal end of arm 104 and can be coupled to pole 108 at proximal joint 111. Electric actuator 112 can also be coupled to a proximal portion of proximal arm 114. Proximal arm 114 can be coupled to electric actuator 112 via a joint or as an actuatable part of actuator 112 in other examples. Distal arm 115 can be coupled to a distal portion of proximal arm 114 via distal joint 113. Effector coupler 118 can connect instrument 105 to the distal end of arm 104. In some examples, lock/unlock button 120 can be provided on or near end effector coupler 118.

The arms of lockable surgical arm system 100 can comprise a serial linkage of arm segments joined by spherical and/or rotational joints. Each of joints 111 and 113 (and any other joints in other examples) can be pivotable and/or rotational joints allowing movement of connected components with one or more degrees of freedom. Joints 111 and 113 (and joints within actuator 112) can be locked and unlocked using base unit 106 and actuator 112, which can be an electric bilateral actuator. In some examples, the joints of the arm can be locked and unlocked with a fluid, pneumatic, or hydraulic system.

While only proximal arm 114 and distal arm 115 are shown in FIG. 1, additional arm segments can be provided between actuator 112 and end effector coupler 118. Each additional arm segment may require one or more additional joints to form a repositionable, lockable support arm structure. Such additional arm segments can provide greater coverage and ability for the arm to be positioned with more degrees of freedom in the surgical field.

In operation of some examples, lock/unlock button 120 can be operable by a user to initiate power locking and unlocking of arm 104. When lock/unlock button 120 is not depressed arm 104 can be in a locked state where joints 111 and 113 are locked such that proximal arm 114 and distal arm 115 cannot move relative to each other or to table 102. When lock/unlock button 120 is pressed, actuator 112 can unlock joints 111 and 113 such that end effector coupler 118 can be positioned, as desired, and as guided by joints 111 and 113 and proximal arm 114 and distal arm 115. That is, end effector coupler 118 can be moved to a desired position relative to body 50 through movement paths limited by the freedom of arm 104 to position instrument 105 to a desired position relative to body 50.

FIG. 2A illustrates a perspective view of surgical arm system 200, in accordance with at least one example of this disclosure. FIG. 2B illustrates a perspective view of surgical arm 200, in accordance with at least one example of this disclosure. FIGS. 2A and 2B are discussed below concurrently.

Figure 2:
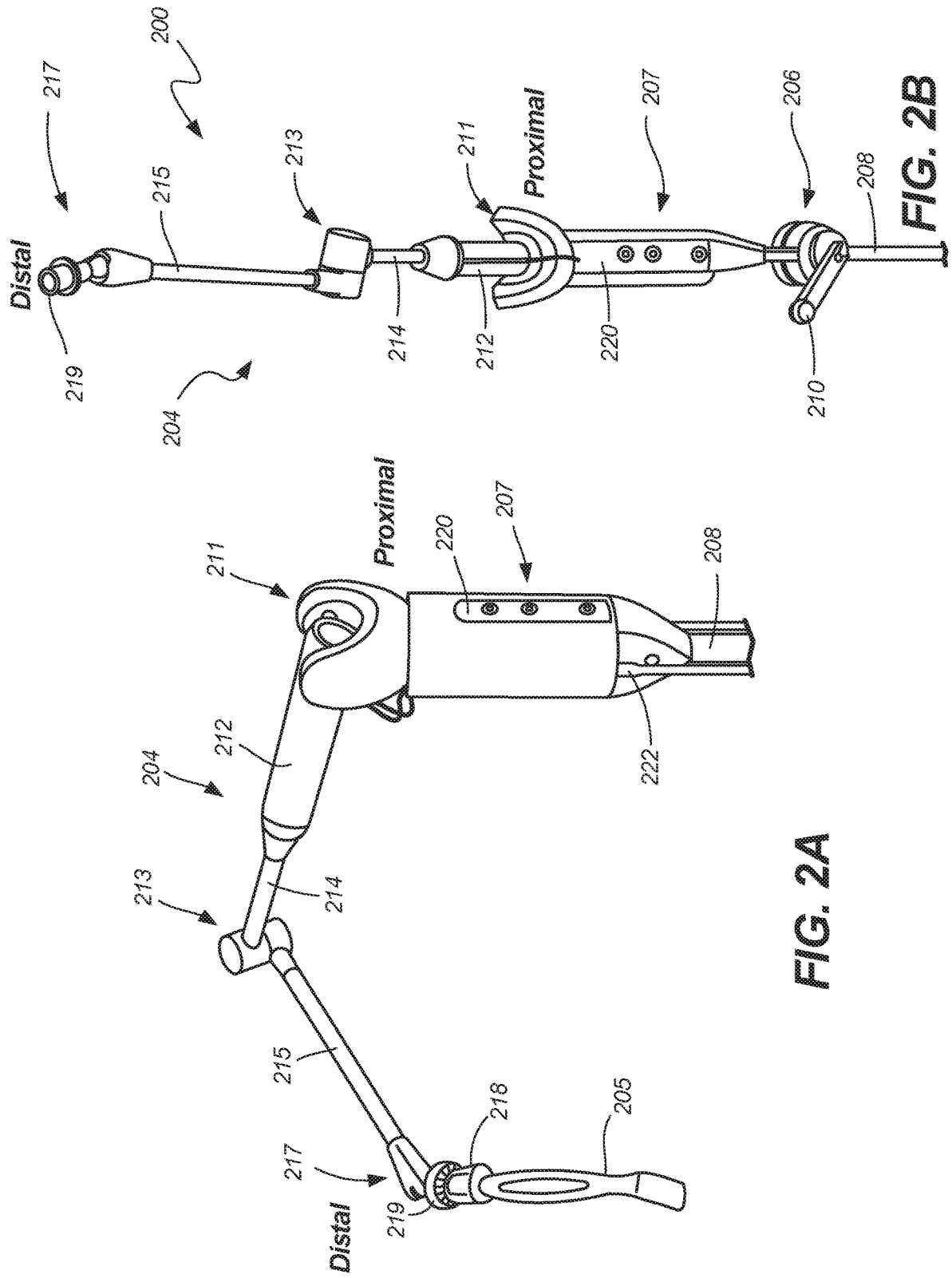
FIG. 2A illustrates a perspective view of a repositionable, lockable surgical arm, in accordance with at least one example of this disclosure.
FIG. 2B illustrates a perspective view of a repositionable, lockable surgical arm, in accordance with at least one example of this disclosure.

Surgical arm 200 can include arm 204, instrument 205, base unit 206 (only shown in FIG. 2B), control device 207, pole 208, and manual clamp 210. Arm 204 can include proximal joint 211, actuator unit 212, distal joint 213, proximal arm 214, distal arm 215, coupler joint 217, end effector coupler 218, and arm coupler 219. Control device 207 can include user interface 220 and can be connected to cable 222. Also shown in FIG. 2 are orientation indicators Proximal and Distal.

Surgical arm 200 can be similar to system 100 discussed above, except that surgical arm 200 can include different features. For example, base unit 206 can be a manually adjustable unit, where manual clamp 210 can be operable to adjust a position of base unit 206 along a rail (e.g., surgical table rail) and to adjust the height of pole 208 (and therefore arm 204). In this example, control device 207 can include electronic components configured to control arm 204. For example, control device 207 can house a controller (discussed further below) and user interface 220, which can include one or more control inputs (such as buttons and switches) and can include audible or visual indicia. Cable 222 can be coupleable to control device 207 to connect a lock/unlock button to control device 207.

Surgical arm 200 can also include arm coupler 219 which can be a distal coupler of arm 204 configured to releasably secure end effector coupler 218 to coupler joint 217 (and therefore to arm 204). In other examples, discussed below, end effector coupler 218 can be fixedly secured to arm 204.

Surgical arm 204 can operate consistently with system 100 described above, except that coupler joint 217 can offer additional range of motion of the embodiment shown in FIG. 1. Further, end effector coupler 218 can be used to quickly and easily remove and secure tools (and therefore instruments), such as tool 205, to surgical arm 204, as discussed in further detail below.

Figure 3:
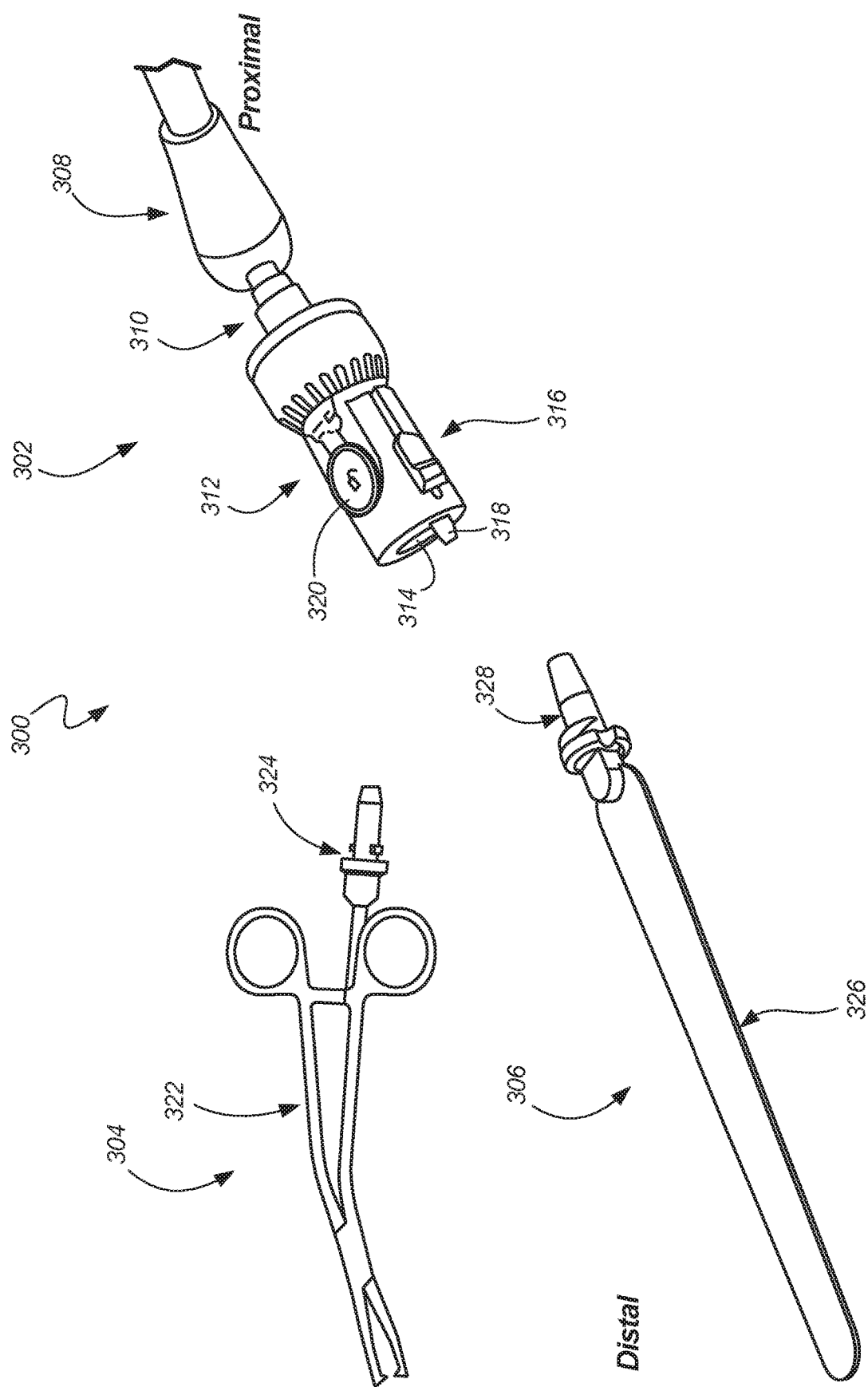
FIG. 3 illustrates a perspective view of a surgical system, in accordance with at least one example of this disclosure.

FIG. 3 illustrates a perspective view of surgical system 300, in accordance with at least one example of this disclosure. End effector system 300 can include arm 302, forceps 304, retractor 306, and lock/unlock button 320. Arm 302 can include distal arm joint 308, arm coupler 310, and end effector coupler 312. End effector coupler 312 can include keyed opening 314, pin release 316, and pin 318. Forceps 304 can include instrument portion 322 and stem 324. Retractor 306 can include instrument portion 326 and stem 328. Also shown in FIG. 3 are orientation indicators Proximal and Distal.

Arm 302 can be consistent with arms 104 and 204 discussed above; however, arm 302 shows additional detail of end effector 312, which can be releasably coupled to distal arm joint 308 via distal coupler 310. End effector coupler 312 can be a coupler configured to releasably secure instruments, such as forceps 304 and retractor 306, to arm 302, and to secure tools, as discussed further in the FIGS. below.

Forceps 304 can be surgical forceps including stem 324 extending from instrument portion 322. Stem 324 can be coupled to instrument portion 322 of forceps 304 such that stem 324 does not interfere with the operation of instrument portion 322 of forceps 304. Retractor 306 can be a substantially flat and/or malleable retractor, such as a ribbon retractor, including stem 328 extending from instrument portion 326 of retractor 306. Stem 328 can be coupled to instrument portion 326 of retractor 306 such that stem 328 does not interfere with the operation of instrument portion 326 of retractor 306. Each of stems 324 and 328 can be of identical structure where each can include tapered stems configured and shaped to be inserted into end effector coupler 312 through keyed opening 314, as discussed in further detail below.

Keyed opening 314 of end effector coupler 312 can include an irregular geometric shape that is sized and shaped to receive each of stems 324 and 328 therethrough to individually secure each of stems 324 and 328 within end effector coupler 312. That is, end effector coupler 312 can secure one stem at a time. Pin 318 of end effector coupler 312 can be disposed within a pin bore of end effector coupler 312 and can extend from a distal end of end effector coupler 312 such that pin 318 can engage a tool stem to help secure the tool stem to the end effector coupler 312. Pin 318 can be coupled to pin release 316, where pin release 316 can be operable to translate pin 318.

Lock/unlock button 320 can be a simple button or switch in some examples and can be in communication with a controller to transmit a signal to lock and unlock the arm.

In operation of some examples, either of stems 324 and 328 can be oriented for insertion and can be inserted into keyed opening 314. Once inserted, the stem can be rotated so that the stem locks into end effector coupler 312 so that a tapered distal end of pin 318 engages an angled (or straight) notch of a collar of the stem to restrict rotation of the stem while within end effector coupler 312. The tool (forceps 304, retractor 306, or other instruments, as discussed below) can then be used in a surgical procedure while connected to end effector coupler 312. And, when lock/unlock button 320 is activated (as discussed in FIGS. 1 and 2 above), end effector coupler 312 and the tool can be positioned as desired (and repositioned) and can be guided by arm 302. Alternatively, the tool can be positioned as desired and then connected to arm 302 when in position.

When the tool is in a desired position, lock/unlock button 320 can be de-activated (or released) to lock a position of arm 302 and therefore of end effector coupler 312 and the instrument (e.g., retractor 306) secured to end effector coupler 312. The instrument can then be used in the desired position and repositioned at any time. When it is desired to remove or change instruments, pin release 316 can be actuated to retract pin 318 so that the tool (and stem 324 or 328) can be rotated within end effector coupler 312 to allow for removal of the stem and tool out of keyed opening 314 and out of end effector coupler 312. This process can be repeated, such that a new tool can be inserted and removed in the same manner.

Figure 4:
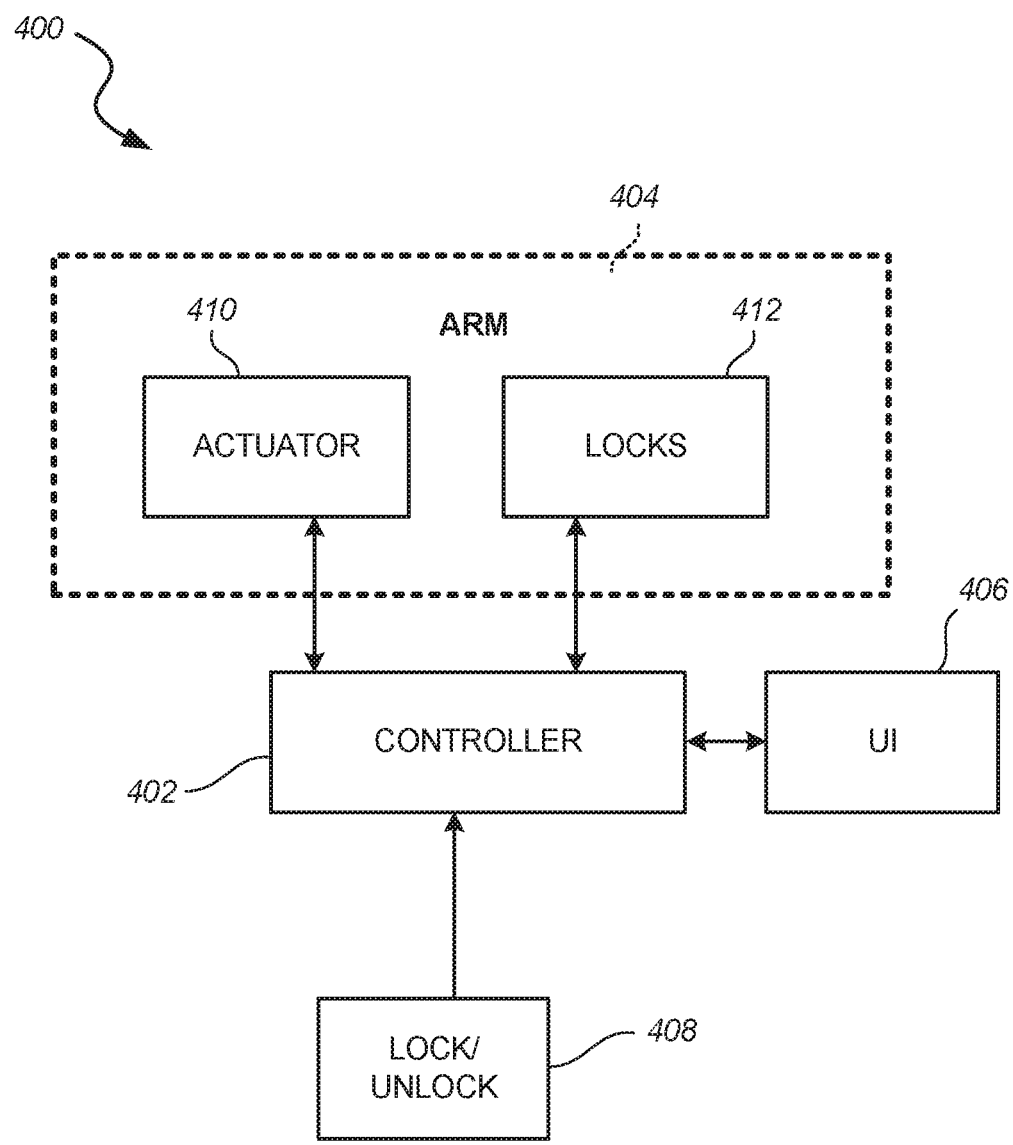
FIG. 4 illustrates a schematic view of a system, in accordance with at least one example of this disclosure.

FIG. 4 illustrates a schematic view of control system 400, in accordance with at least one example of this disclosure. Control system 400 can include controller 402, surgical arm 404, user interface 406, and lock/unlock button 408. Surgical arm 404 can include actuator 410 and lock(s) 412.

Controller 402 can be a programmable controller, such as a single or multi-board computer, a direct digital controller (DDC), or a programmable logic controller (PLC). In other examples controller 402 can be any computing device, such as a handheld computer, for example, a smart phone, a tablet, a laptop, a desktop computer, or any other computing device including a processor and wireless communication capabilities.

Surgical arm 404 can be similar to the arms discussed above with respect to FIGS. 1-3 in that arm 404 can be a movable arm that is lockable in a desired position. Actuator 410 can be an electric, fluid, or gas powered actuator in communication with controller 402 and can be operable to translate or otherwise move one or more components (such as an armature) in response to a control signal. Actuator 410 can be physically coupled to locks 412 which can be mechanical or electro-mechanical locks coupled to joints or arms of arm 404. In other examples, actuator 410 can be omitted and locks 412 can be individually operable in response to individual or shared control signals from controller 402.

Control system 400 can optionally include user interface 406 that can be in communication with controller 402. In another example, user interface 406 can be separate from control system 404 or can be communicatively coupled to control system 404.

Lock/unlock button 408 can be a simple button or switch in some examples and can be in communication with controller 402. In some examples, button 408 can be attached to a portion of arm 404. In other examples, button 408 can be attached to other components, such as table 102 of FIG. 1 or can be located on a floor and can be operated as a foot pedal or switch. In other examples, a controller may not be present and lock/unlock button 408 can be in direct communication with actuator 410 and/or locks 412.

User interface 406 can be any display and/or input device. For example, user interface can be a monitor, keyboard, and mouse in one example. In other examples, user interface 406 can be a touch screen display. In yet another example, user interface 406 can provide lights, buttons, and/or switches. Controller 402 and user interface 406 can include machine readable medium. The terms "machine readable medium" may include any medium that is capable of storing, encoding, or carrying instructions for execution by the device and that cause the device to perform any one or more of the techniques of the present disclosure, or that is capable of storing, encoding or carrying data structures used by or associated with such instructions. Non-limiting machine readable medium examples may include solid-state memories, and optical and magnetic media. Specific examples of machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

In operation of some examples, a user can interact with user interface 406 to power on control system 400. Power can be indicated by a light, for example, on user interface 406 and/or on arm 404. The user can then operate button 408 to send an unlock signal to controller 402 to initiate power locking and unlocking of arm 404. In response, controller 402 can send a signal to actuator 410 and/or locks 412 to unlock locks 412. Once arm 404 is unlocked, the user can move a tool (and instrument) and arm 404 to a desired location and orientation relative to a patient. When the user releases the lock/unlock button, it can send a lock signal (or can cease sending an unlock signal) to controller 402. In response, controller 402 can send a signal (or can cease sending an unlock signal) to actuator 410 and/or locks 412 to lock the joints of arm 404, locking arm 404 in the desired position such that the joints of arm 404 cannot articulate and the end effector of arm 404 cannot move relative to arm 404.

Though the components of control system 400 are shown as being wired to controller 402, the lines of FIG. 4 connecting components of control system 400 can also represent wireless communication paths where each component can communicate using wireless (electromagnetic signals) through protocols such as WiFi, Bluetooth (Bluetooth LE), Near-Field Communications (NFC), and the like.

Figure 5:
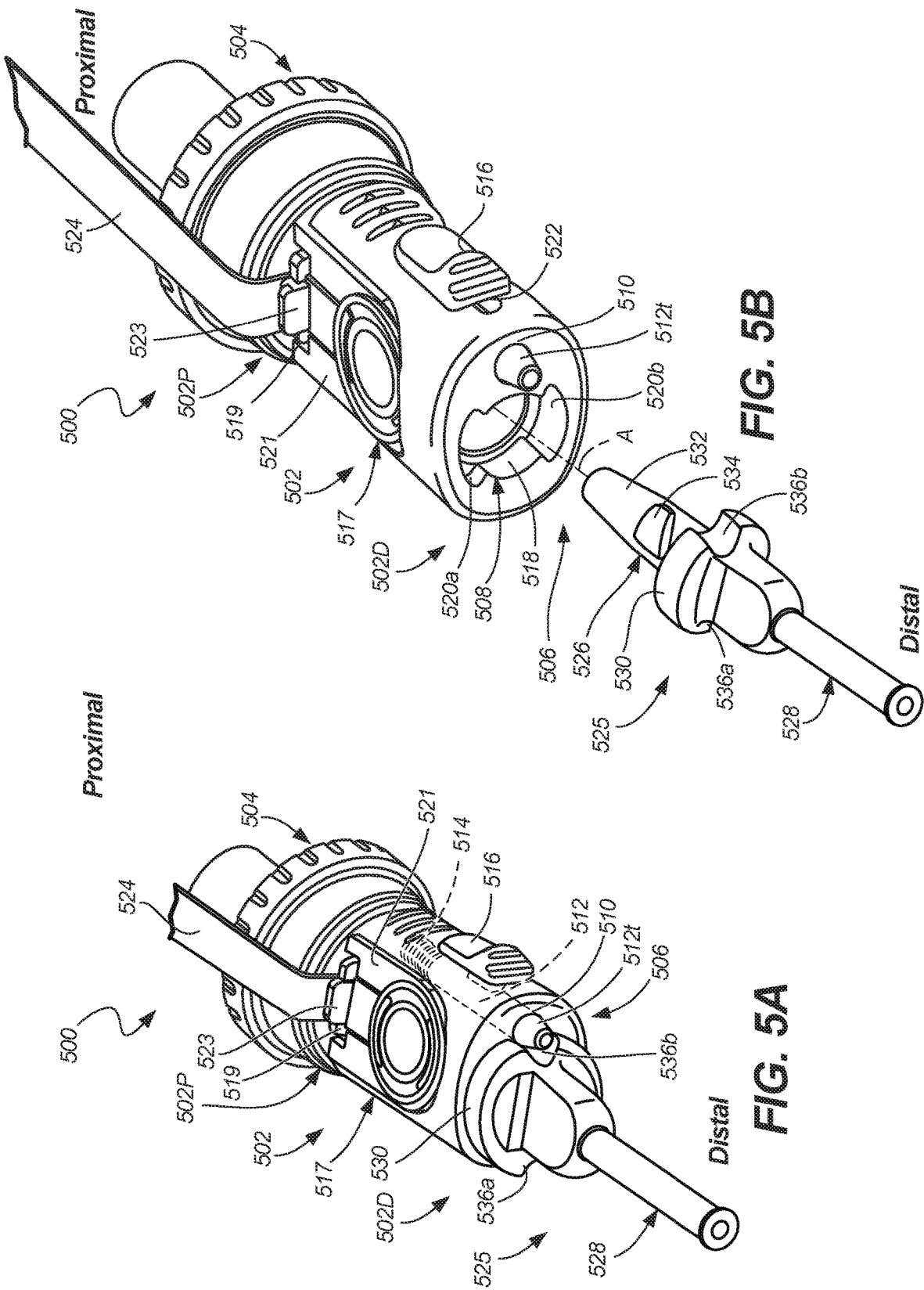
FIG. 5A illustrates a perspective view of an end effector coupler in a first condition, in accordance with at least one example of this disclosure.
FIG. 5B illustrates a perspective view of an end effector coupler in a second condition, in accordance with at least one example of this disclosure.

FIG. 5A illustrates a perspective view of end effector coupler 500 in a first condition, in accordance with at least one example of this disclosure. FIG. 5B illustrates a perspective view of end effector coupler 500 in a second condition, in accordance with at least one example of this disclosure. FIGS. 5A and 5B are discussed below concurrently.

End effector coupler 500 can include body 502, proximal coupler 504, and tool lock 506. Tool lock 506 can include keyed opening 508, pin bore 510, pin 512 (including tapered portion 512t), biasing element 514, pin release 516, button 517, and cable 524. Keyed opening 508 can include central bore 518 (or stem opening) and keyways 520a and 520b. Body 502 can also include catch 519, flat surface 521, and slot 522. Button 517 can include tab 523. Also shown in FIGS. 5A and 5B is tool 525, which can include stem 526, tool portion 528, and flange 530. Stem 526 can include tapered portion 532 and projections 534 (or key bits 534). Flange 530 can include notches 536a and 536b. Also shown in FIGS. 5A and 5B are orientation indicators Proximal and Distal and Axis A.

Body 502 can be a rigid or semi-rigid body comprised of materials such as metals, plastics, foams, elastomers, ceramics, composites, and combinations thereof. Body 502 can include proximal portion 502P and an opposite distal portion 502D including a distal end. Body 502 can be sized and shaped to be handheld and hand-positioned. For example, body 502 can be ergonomically shaped and can include ridges or crenulations to promote ergonomics and grip. Slot 522 of body 502 can be an axially extending slot along a side of body 502 adjacent pin bore 510 and can be sized to allow a portion of pin release 516 to extend through body 502 to couple to pin 512.

Flat surface 521 can be an outer surface of body 502 that is substantially planar or flat and is sized to receive button 517 thereon. Catch 519 can extend outward from flat surface 521 proximate a proximal end of flat surface 521.

Button 517 can be a simple button or switch in some examples and can be connected to a controller through cable 524 to transmit a signal to lock and unlock the arm. Tab 523 can be a locking tab configured to elastically deflect (like a spring) and can include a projection configured to engage catch 519 to secure button 517 to body 502. Cable 524 can be a communication and/or power cable connected to button 517 and to a controller (such as controller 402 of FIG. 4). Cable 524 can be several types of communication cable such as shielded twisted pair (STP), unshielded twisted pair (UTP), fiber optic cable, ethernet cable, coaxial cable, or a patch cable, and the like. In some examples, cable 525 can pass through catch 523 to connect to button 517. In other examples, a wireless component, such as a Bluetooth chip, can be installed at distal end of a surgical arm and can be in electronic communication with button 517, such that the chip can send wireless signal to a controller.

Proximal coupler 504 can be a rigid or semi-rigid body comprised of materials such as metals, plastics, foams, elastomers, ceramics, composites, and combinations thereof. Proximal coupler 504 can have a substantially hollow cylindrical geometric shape and can be securable to distal portion 502D of body 502. In some examples, proximal coupler 504 can include a threaded portion configured to secure proximal coupler 504 to a surgical arm.

Tool lock 506 can be comprised of multiple components of end effector coupler 500 and can be configured to secure tool 525 to end effector coupler 500. Keyed opening 508 of tool lock 506 can be a central bore 518 of keyed opening 508 configured to receive a tool stem therein. Central bore 518 can be a longitudinal bore extending into body 502 from the distal end of distal portion 502D of body 502. Central bore can extend into body 502 along axis A, which can be central to keyed opening 508 and central to body 502 in some examples, but can be offset from a central axis of body 502 in other examples. In some examples, central bore 518 can be sized to receive tool stem 526 in a taper-to-taper arrangement, as discussed further below.

Keyways 520a and 520b can be notches extending radially from central bore 518 and can be sized and shaped to receive key bits 534 of tool 525 when key bits 534 are aligned with keyways 520a and 520b, but can prevent passage of key bits 534 into or out of keyways 520a and 520b (therefore preventing stem from being inserted into keyed opening 508 or being removed therefrom) when key bits 534 are not aligned with keyways 520a and 520b. As discussed further below, each of keyways 520a and 520b can include a proximal face, where each proximal face is engageable with key bits 534 of tool 525.

Pin bore 510 can be a longitudinal bore extending into body 502 from the distal end of distal portion 502D of body 502. In some examples, pin bore 510 can be adjacent (i.e., proximate or near) central bore 518 and can extend through body 502 substantially parallel to central bore 518 and axis A, but can be not parallel to central bore 518 in other examples.

Pin 512 can be a rigid or semi-rigid body comprised of materials such as metals, plastics, foams, elastomers, ceramics, composites, and combinations thereof. Pin 512 can include tapered portion 512t at a distal termination of pin 512. Pin 512 can be disposed within pin bore 510 such that tapered portion 512t extends from pin bore 510 (and therefore beyond distal portion 502D of body 502) when pin 512 is in an extended or locked position.

Biasing element 514 can be a resilient element such as a spring. In some examples, biasing element 514 can be a compression coil spring. In other examples, biasing element can be other springs or resilient members, such as a wave spring or compressible and resilient members comprised of materials such as rubbers, plastic, and the like. In some examples, biasing element can be disposed within pin bore 510 to engage a proximal termination of pin bore 510 and to engage a proximal termination of pin 512, such that biasing element 514 biases pin 512 distally relative to body 502. Pin release 516 can be an actuator operable by hand or tool and can be coupled to pin 512 through slot 522 of body 502.

Tool 525 can be a surgical instrument such as forceps or a retractor (as described below), or various other surgical instruments that can be adapted to include a stem. Stem 526 can be a keyed stem, shaped and sized to be inserted within end effector coupler 500 to secure tool 525 to end effector coupler 500. Tool portion 528 can be connected and/or integral to the operable tool, such as the forceps or retractor. Flange 530 can be a flange or collar extending radially outward from stem and can include notches 536a and 536b extending substantially axially therethrough (though notches 536a and 536b can extend through flange 530 at an axis not parallel with the axis of stem 526, in some examples).

Stem 526 can also include tapered portion 532, which can be sized and shaped to extend into central bore 518 of keyed opening 508, where stem 526 can be tapered to mate with a tapered bore of body 502. Key bits 534 of stem 526 can be projections extending radially outward from stem 526 and key bits 534 can be sized and shaped to pass through keyways 520a and 520b when key bits 534 are aligned with keyways 520a and 520b. Key bits 534 can also be used to secure stem 526 within central bore 518 as discussed further below.

In some examples a diameter of tool stem 536 can be about 9.9 millimeters (mm). In some examples, tapered portion 532 can include a first taper at a 6 degree angle from a surface of the stem and a second taper at a 45 degree angle, where tapered portion 532 can be about 16.01 mm in axial length. In some examples, flange 530 can have a radius of about 9.4 mm and each of notches 536a and 536b can have a radius of 3 mm. In some examples, notches 536a and 536b can extend through flange 530 at an angle of about 15 degrees. In some examples, an angle of an angled face of each of key bits 534 can be at about a 30 degree angle with a face of flange 530. In some examples, a length of tool stem 536 to an end of tool stem 536 can be about 33 mm, and an axial length of the flange can be about 5.13 mm, and an axial length of each of key bits 534 can be about 5.86 mm, where each key bit 534 can be about 4.14 mm from flange 530.

In operation of some examples, tool 525 can be separate from end effector coupler 500, as shown in FIG. 5B. When it is desired to secure tool 525 to end effector coupler 500, tool stem 526 can be inserted into central bore 518 and rotated clock-wise approximately one quarter of a turn to secure tool 525 to end effector coupler 500. In other examples, tool 525 (and stem 526) can be rotated less than a quarter turn, when additional keyways are included (as discussed below in FIG. 7), and greater than a quarter turn when only one keyway is used.

More specifically, tool stem 526 can be inserted into central bore 518 until key bits engage body 502. Key bits 534 can then be aligned with keyways 520a and 520b to allow tool stem 526 to be further inserted into central bore 518. As discussed further below, tool stem 526 can then be rotated clockwise (from a distal perspective) to seat key bits 534 within a counterbore of central bore 518, where contact between key bits 534 and portions of central bore 518 draw tool stem 526 completely into central bore 518 as stem 526 is rotated. In other examples, tool stem 526 can be rotated counter-clockwise to seat key bits 534 within the counterbore of central bore 518.

Alternatively, tool stem 526 can be inserted into central bore 518 until key bits engage body 502. Key bits 534 can then be aligned with keyways 520a and 520b to allow tool stem 526 to be further inserted into central bore 518 entirely until key bits 534 rest within a counter bore of central bore 518 which extends stem 526 entirely into central bore 518. Tool stem 526 can then be rotated clockwise (from a distal perspective) to seat key bits 534 within the counterbore of central bore 518.

During insertion of tool stem 526 into central bore 518, a proximal portion of flange 530 can contact pin 512 to cause pin 512 to move proximally into pin bore 510. As tool stem 526 is rotated, one of notches 536a and 536b will align with tapered portion 512t of pin 512 as key bits 534 draw tapered portion 532 into central bore 518, allowing pin 512 to extend from pin bore 510 and into either notch 536a or notch 536b. Pin 512 can automatically extend to this extended position due to being biased to extend distally from pin bore 510 by biasing element 514. When pin 512 is in this position, pin 512 can apply a force from biasing element 514 on flange 530 to further ensure a stable connection between tool 525 and end effector coupler 500. Also, as pin 512 engages one of notches 536a and 536b, the interaction can produce a noise in addition to being visible through one of notches 536a or 536b, which can provide indications to an operator that tool 525 is secured to end effector coupler 500.

The taper-to taper interface of stem 526 with central bore 518 and the engagement of key bits 534 with a proximal portion of keyed opening 508 and the counterbore of central bore 518 can both help limit undesired movement of tool 525 relative to end effector coupler 502; and, the engagement of flange 530 with pin 512 can help limit counter-clockwise rotation of tool 525 relative to central bore 518 and body 502 to help prevent back-out of tool 525 from end effector coupler 500, securing tool 525 to end effector coupler 502. In some examples, during insertion of stem 526 into central bore 518, contact between taper-to taper interface of stem 526 with central bore 518 can occur substantially simultaneously as the engagement of key bits 534 with a proximal portion of keyed opening 508 and substantially simultaneously as the engagement of flange 530 with pin 512 so that stem 526 is secured in all directions relative to end effector coupler 502 all at once.

Also, because tapered portion 512t is tapered and because notches 536a and 536b can be angled, tapered portion 512t can contact a large surface area of either one of notches 536a and 536b. This contact can further help limit unwanted back-out of tool 525 from end effector coupler 500. All of these features that help secure tool 525 to end effector coupler 500 can provide a wear resistant design for the application where users frequently change instruments for different procedures.

When tool 525 is secured to end effector coupler 500, lock/unlock button 517 can be operated (or pressed) to unlock the surgical arm to which end effector coupler 500 is secured. The end effector coupler 500 and tool 525 can then be positioned as desired while lock/unlock button 517 is pressed. Then, when a desired position is obtained, lock/unlock button 517 can be released to lock the joints of the surgical arm, holding the desired position of end effector coupler 500 and tool 525.

Figure 6:
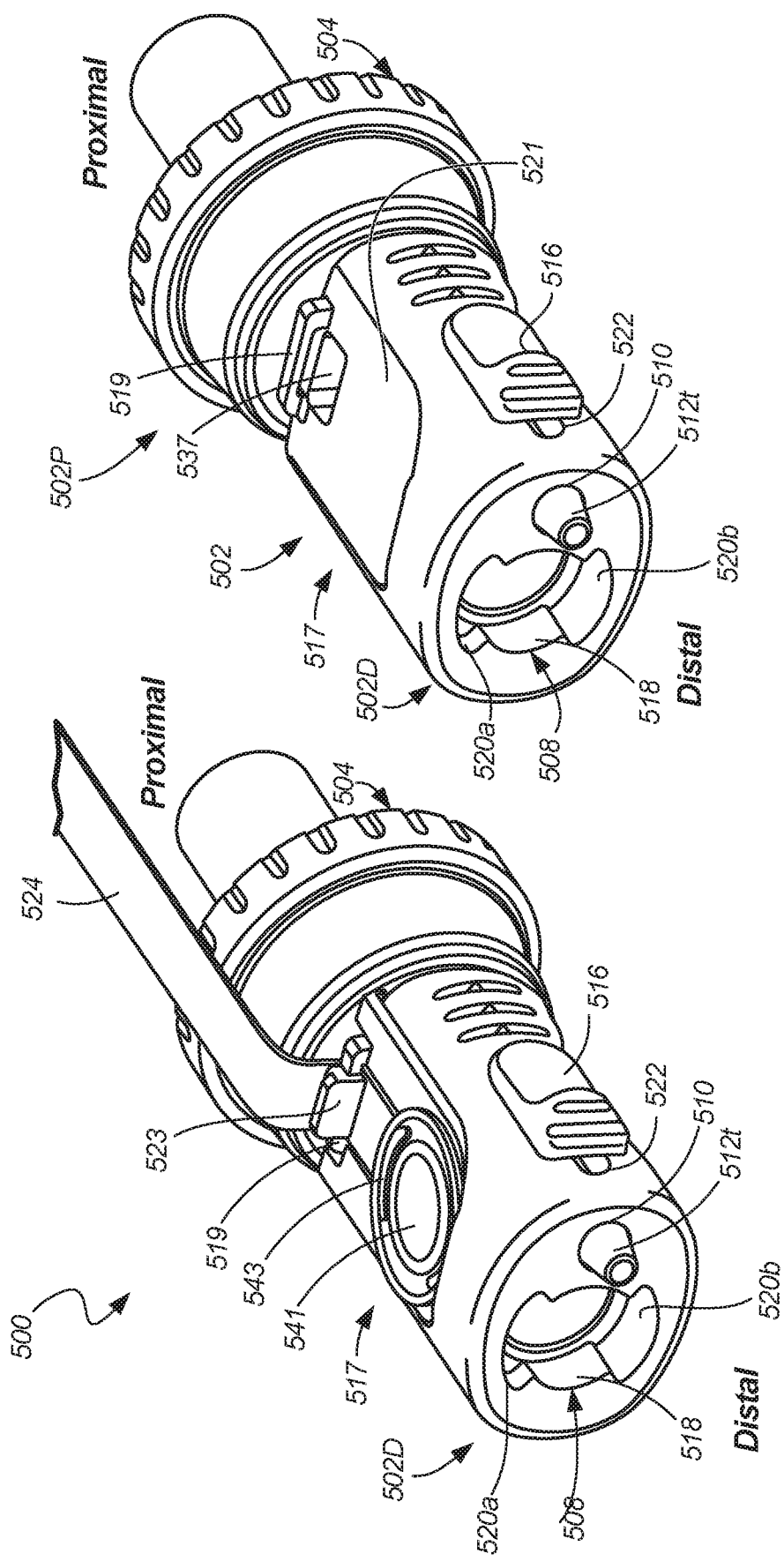
FIG. 6A illustrates a perspective view of an end effector coupler in a first condition, in accordance with at least one example of this disclosure.
FIG. 6B illustrates a perspective view of an end effector coupler in a second condition, in accordance with at least one example of this disclosure.

When it is desired to remove tool 525 from end effector coupler 500, pin release 516 can be translated proximally, where slot 522 guides and limits translation of pin release 516. Proximal retraction of pin release 516 can retract pin 512 into pin bore such that pin 510 is no longer engaging a notch (of notches 536a and 536b), as shown in FIG. 6B. This allows a user to rotate tool 525, along with stem 526 and flange 530, counter-clockwise so that key bits 534 can be disengaged from the distal side of keyed opening 508 and can move out of the counterbore and into alignment with keyways 520a and 520b of central bore 518, allowing stem 526 to be removed from central bore 518. Because pin release 516 can be easily actuated by hand and rotation of stem 526 requires about a quarter turn of tool 525 with little resistance, tool 525 can be easily and quickly removed from end effector coupler 500.

FIG. 6A illustrates a perspective view of end effector coupler 500 in a first condition, in accordance with at least one example of this disclosure. FIG. 6B illustrates a perspective view of end effector coupler 500 in a second condition, in accordance with at least one example of this disclosure. FIGS. 6A and 6B are discussed below concurrently.

End effector coupler 500 of FIGS. 6A and 6B can be similar to end effector 500 discussed above; however, FIGS. 6A and 6B below show how button 517 can be removeable from end effector coupler 500 for cleaning (such as autoclaving) of end effector coupler 500.

As shown in FIG. 6A, button 517 can be secured to flat surface 521 of body 502 through an interface between tab 523 of button 517. A projection of tab 523 can be lockingly engaged with catch 519 and can be partially inserted into body 502 through tab channel 537 (shown in FIG. 6B). As discussed above, tab 523 can be configured to elastically deflect (like a spring). When it is desired to remove button 517 from body 502, tab 523 can be moved (or deflected) distally to release tab 523 from catch 519 so that tab 523 can be removed from tab channel 537, allowing button 517 to be removed from end effector coupler 500. Though tab channel 537 is shown as extending into body 502 from flat surface 521 near a proximal side of catch 519, tab channel 537 can be located in any position relative to catch 519 and can be omitted entirely in other examples. Similarly, catch 519 can be positioned in various locations around flat portion 521 of body 502.

Button 517 can also include switch 541 and light emitting diode (LED) 543. Switch 541 can be an operable portion of button 517 and can be pressed to cause button 517 to send a signal through cable 524 to a controller. LED 543 can also be connected to the controller and can be configured to emit a light, for example, to serve as a visual indication that switch 541 is pressed (or is not pressed). In other examples, LED 543 can indicate that the surgical arm is in a powered on state.

Figure 7:
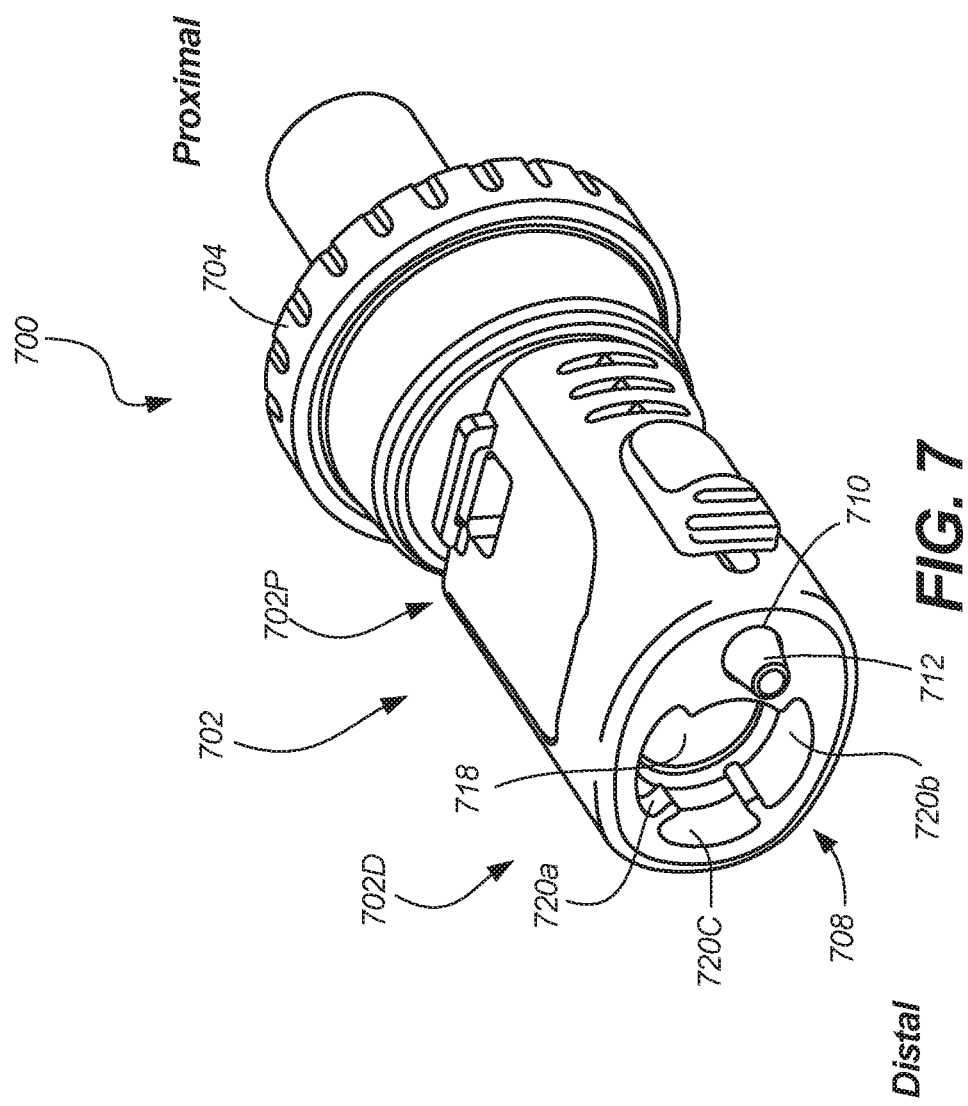
FIG. 7 illustrates a perspective view of an end effector coupler, in accordance with at least one example of this disclosure.

FIG. 7 illustrates a perspective view of end effector coupler 700, in accordance with at least one example of this disclosure. End effector coupler 700 can include body 702 (having proximal portion 702P and distal portion 702D) and coupler 704. Body 702 can include keyed opening 708, pin bore 710, and pin 712. Keyed opening 708 can include central bore 718 and keyways 720a, 720b, and 720c.

End effector 700 can be similar to end effector 500 discussed above, except that end effector 700 can include three keyways, keyways 720a-720c. In this example, keyed opening 708 can be configured to receive a tool stem that includes three key bits. The additional key bits can help to secure the tool to end effector coupler 700. Also, by including an asymmetric arrangement of keyways 720a-720c, keyways 720a-720c can ensure that a tool is coupled to end effector coupler 700 in a single orientation, which can help to prevent improper connection of tools that require a particular orientation of the tool with respect to end effector coupler 700.

In some other examples, keyways 720a-720c can be smaller in size and/or spaced away from pin bore 710 and pin 712 such that 4, 5, 6, 7, 8, 9, 10, and the like keyways can be included in keyed opening 708. In other examples, more key bits can be used by replacing pin 712 with another locking mechanism, such as a latch, to secure body 702 to the tool stem.

FIG. 8A illustrates a perspective view of cable 824, in accordance with at least one example of this disclosure. FIG. 8B illustrates a perspective view of a portion of cable 824, in accordance with at least one example of this disclosure. FIG. 8C illustrates a perspective view of a portion of cable 824, in accordance with at least one example of this disclosure. Cable 824 can include flat portion 826, round portion 828, coupler 830, and connector 832. Also shown in FIGS. 8A and 8B is button 817, which can be consistent with button 517 discussed above.

Each of flat portion 826 and round portion 828 of cable 824 can be a communication cable which may or may not include power. In some examples, each of flat portion 826 and round portion 828 can be various types of communication cable such as STP, UTP, fiber optic cable, ethernet cable, coaxial cable, or a patch cable, and the like.

Coupler 830 can be a coupler connected flat portion 826 to round portion 828. In some examples where flat portion 826 and round portion 828 are the same type of cable, such as STP, coupler 830 can be a simple coupler or connector. In other examples where flat portion 826 and round portion 828 are not the same type of cable, coupler 830 can also be an adapter. Connector 832 can be a plug, jack, or other type of connector used to transmit an analog signal. In other examples, connector 832 can be a digital connector, such as when cable 824 is an optical or ethernet cable. In some examples, connector 832 can be used to connect button 817 to a controller (such as controller 402 of FIG. 4).

FIG. 9A illustrates a perspective view of instrument holder 900, in accordance with at least one example of this disclosure. FIG. 9B illustrates a perspective view of instrument holder 900 in a first condition, in accordance with at least one example of this disclosure. FIG. 9C illustrates a perspective view of instrument holder 900 in a second condition, in accordance with at least one example of this disclosure. FIGS. 9A through 9C are discussed below concurrently.

Instrument holder 900 can include shaft 902, sleeve 904, collar 906, stem 908 (which can be a portion of shaft 902), and retaining pins 910a and 910b (only one visible in FIGS. 9A-9C). Shaft 902 can include axial bore 912, coupling bore 914, and axial slots 916a and 916b. Sleeve 904 can include notch 918 (having faces 920a and 920b), pin bores 922 (only one visible in FIGS. 9A-9C), and fingers 924. Also shown in FIGS. 9A-9C are axes A1 and A2 (only shown in FIG. 10B) and orientation indicators Proximal and Distal. Also shown in FIG. 9B is instrument 925.

Instrument holder 900 can be comprised of materials such as metals, plastics, foams, elastomers, ceramics, composites, and combinations thereof. In some examples, instrument holder 900 can be comprised of rigid metals such as stainless steel alloys and titanium for their strength properties and their ability to be cleaned (such as through an autoclave procedure), allowing instrument holder 900 to be reusable.

Shaft 902 can be a rigid or semi-rigid and elongate body. Shaft 902 can extend proximally to distally along axis A1 and can include axial bore 912 extending along axis A1. Coupling bore 914 can extend through shaft 902 along axis A2 substantially orthogonally (or transversely) to axis A1. Axial slots 916a and 916b can extend through an outer wall of shaft 902 and can intersect with axial bore 912. Axial slots 916a and 916b can extend axially along shaft 902 terminating distally before reaching a distal end of shaft 902. Each of axial slots 916a and 916b can be sized to receive retaining pins 910a and 910b (respectively therethrough).

Sleeve 904 can be an elongate body having a geometric shape substantially of a hollow cylinder. Sleeve 904 can include an internal diameter that is larger than an outer diameter of shaft 902 such that sleeve 904 can be disposed around shaft 902 (and around a portion of collar 906, as discussed below). Notch 918 can be a notch in a distal end of sleeve 904 formed by faces 920a and 920b extending angularly proximally toward each other from a distal edge of sleeve 904. Notch 918 can have a geometric shape substantially of a V in some examples.

Pin bores 922 (only one visible in FIGS. 9A-9C) can extend through sleeve 904 substantially orthogonally to axis A1 and axial bore 912 of shaft 902. In some examples, pin bores 922 can be sized to receive and retain retaining pins 910a and 910b therein. Fingers 924 can be one or more individual projections extending proximally from sleeve 904 around a circumference of sleeve 904. In some examples, fingers 924 can each include a radial projection (extending radially inward) and configured to engage a distal portion of collar 906, as discussed further below.

Collar 906 can be an elongate body having a geometric shape substantially of a hollow cylinder. Collar 906 can include an internal diameter that is larger than an outer diameter of shaft 902 such that collar 906 can be disposed around shaft 902. Also, collar 906 can have an external diameter that is smaller than a portion of sleeve 904 such that collar 906 and sleeve 904 can be releasably coupleable at a distal portion of collar 906 and a proximal portion of sleeve 904.

Stem 908 (which can be a portion of shaft 902) can be coupleable to a surgical arm through an end effector coupler (such end effector coupler 500 above). In some examples, stem 908 can be substantially coaxial with shaft 902 (along axis A1). However, in other examples, stem 908 can be adjustable or can be transverse or non-coaxial with shaft 902.

Retaining pins 910a and 910b can be rigid elongate members configured to pass through sleeve 904 (and can be securable thereto through an interference fit, for example). Retaining pins 910a and 910b can be of a length sufficient to extend from sleeve 904 and into axial slots 916a and 916b respectively, such as without passing through coupling bore 914 to avoid contact with an instrument during use of instrument holder 900.

Instrument 925 can be any instrument of a size that can pass through coupling bore 914. In some examples, instrument holder 900 can be a scope holder configured to retain scopes. In some examples, instrument 925 can be a scope, such as an endoscope. In some examples, coupling bore 914 can be sized to receive scopes having a diameter in the range of 4 millimeters (mm) to 10 mm. In other examples, coupling bore 914 can be sized to receive scopes having a diameter in the range of 1 mm to 20 mm, and the like. In yet other examples, instrument 925 can be any other elongate instrument, such as a pin, rod, or k-wire.

In operation of some examples, collar 906 and sleeve 904 can be in a proximal position relative to shaft 902 as shown in FIG. 9C. When it is desired to retain an instrument, such as instrument 925, within instrument holder 900, instrument 925 can be inserted through coupling bore 914 and retained therein while collar 906 is advanced distally. Collar 906 can be rotated to translate and in doing so can engage sleeve 904 to cause sleeve 904 to translate distally with collar 906 until notch 918 of sleeve 904 engages instrument 925.

Faces 920a and 920b of notch 918 together with distal edges of coupling bore 914 can engage instrument 925 to retain instrument 925. Each of faces 920a and 920b and edges of coupling bore 914 can have relatively small thicknesses. These small thicknesses can help convert a clamping force applied to instrument 925 into a relatively high pressure (due to a small contact area between instrument 925 and faces 920a and 920b and edges of coupling bore 914). These four-point small area contact with instrument 925 can limit movement of instrument 925 vertically, helping to minimize slippage.

When it is desired to adjust or remove instrument 925, sleeve 904 and/or collar 906 can be translated distally to disengage faces 920a and 92b of notch 918 from instrument 925 so that instrument 925 can be moved within (or out of) coupling bore 914. The movement of sleeve 904 and therefore coupler 906 can be limited by retaining pins 910 and slots 916. Because pins 910 are coupled to sleeve 904, sleeve 904 is prevented from rotating relative to shaft 902, ensuring notch 918 remains aligned with coupling bore 914. Also, because slots 916 do not extend the full length of shaft 902, retaining pins 910 can engage proximal and distal terminations of slots 916 to limit translation of pins 910 and therefore sleeve 914 and coupler 906 relative to shaft 902.

Either before or after instrument 925 has been secured to instrument holder 900, stem 908 can be secured to an end effector coupler (such as end effector coupler 500 discussed above), to releasably secure instrument 925 and instrument holder 900 to the surgical arm.

Figure 10C:
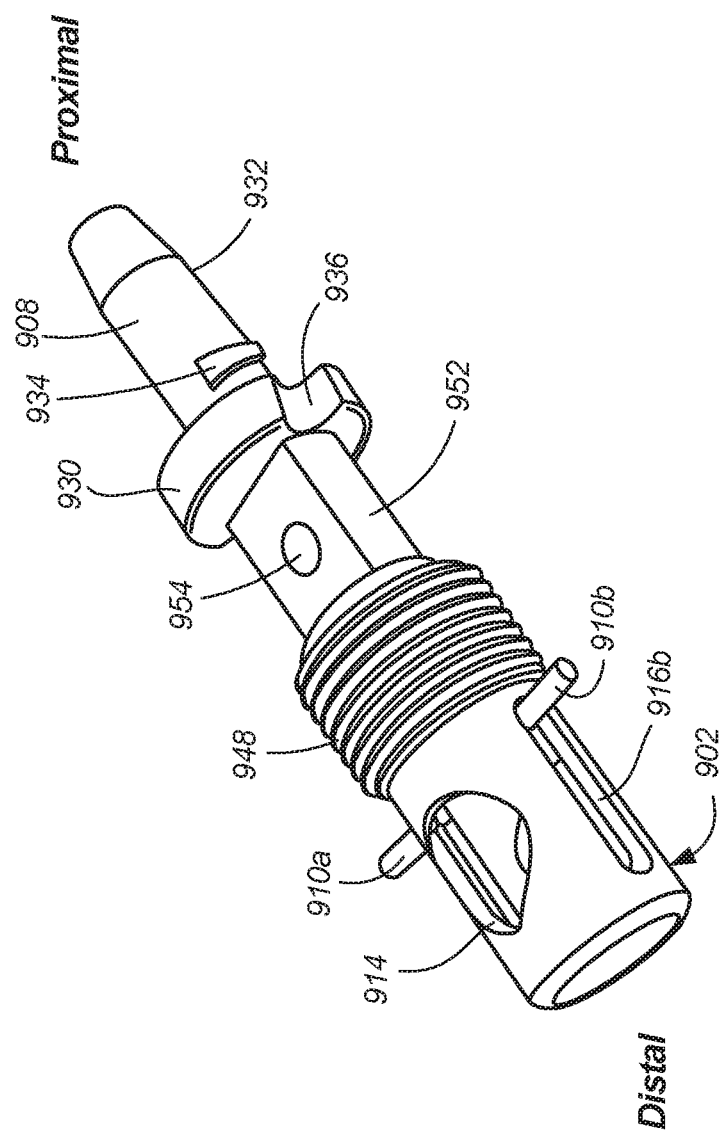
FIG. 10C illustrates a perspective view of an instrument holder, in accordance with at least one example of this disclosure.

FIG. 10A illustrates a perspective view of instrument holder 900, in accordance with at least one example of this disclosure. FIG. 10B illustrates a perspective view of an instrument holder 900, in accordance with at least one example of this disclosure. FIG. 10C illustrates a perspective view of an instrument holder 900, in accordance with at least one example of this disclosure. FIGS. 10A-10C are discussed below concurrently.

Instrument holder 900 of FIGS. 10A-10C can be similar to instrument holder 900 of FIGS. 9A-9C except that FIGS. 10A-10C show additional features of instrument holder 900. For example, FIG. 10A shows details of stem 908, including flange 930 (including notch 936), tapered portion 932, and key bit 934, all of which can be consistent with tool 525 discussed above with respect to FIGS. 5A and 5B.

FIG. 10A also shows distal projection 940 of collar 906, which can extend radially from a distal portion of collar 906. Also shown is biasing element 942 which can be a resilient element such as a spring. In some examples, biasing element 942 can be a compression coil spring. In other examples, biasing element 942 can be other springs or resilient members, such as a wave spring or other compressible and resilient members comprised of resilient materials such as rubbers, plastic, metals and the like. In some examples, biasing element 942 can be disposable around a distal portion of collar 906 and can be axially retained through engagement with distal projection 940 of collar 906. Biasing element 942 can further extend into sleeve 904 where biasing element 942 can engage sleeve 904 to axially retain biasing element 942 at a distal end of biasing element 942 and to radially retain biasing element 942.

FIGS. 10A and 10B also show radial projections 944 of fingers 924 which can each extend radially inward from a proximal portion of each of fingers 924. Each of radial projections 944 can be configured to engage a proximal portion of distal projection 940 of collar 906 to releasably couple collar 906 to sleeve 904. In some examples, fingers 924 can cantilever from a body of sleeve 904 such that fingers 924 can elastically deflect (like a spring) and can allow sleeve 904 to be releasably secured to collar 906.

Also, FIG. 10A shows internal threading 946 of collar 906 and FIGS. 10B and 10C show male threading 948 of shaft 902 located proximally of axial slots 916a and 916b. Male threading 948 of shaft 902 can be configured to receive internal threading 946 of collar 906 such that collar 906 can be threadably engaged with shaft 902 where rotation of collar 906 can cause translation of collar 906 (and sleeve 904) relative to shaft 902. In some examples, collar 906 can include lobes 950, which can radially protrude from collar 906 to provide a gripping surface for hand rotation of collar 906.

In operation of some examples, biasing element 942 can engage a distal portion of distal projection 940 of collar 906 and can engage a portion of sleeve 904 to bias sleeve 904 distally from collar 906. When it is desired to retain an instrument (such as instrument 925), the instrument can be inserted into coupling bore 914 and collar 906 can be threaded on shaft 902 to translate collar 906 and sleeve 904 distally to engage the instrument. After engagement, biasing element 942 can compress as collar 906 is threaded further distally to increase a force applied on the instrument, where the desired force can be selected by an amount collar 906 is threaded distally down shaft 902. Once biasing element 942 reaches its maximum compression, any additional torque provided through threading of collar 906 distally further locks the instrument in position.

In some examples, after sleeve 904 is translated so that notch 918 is aligned or partially aligned with retaining bore 914, sleeve 904 can be translated proximally by hand (without rotation of collar 906) by overcoming a spring force of biasing element 942. This operation may be easier to perform by hand when biasing element 942 is not at maximum compression. Translation of sleeve 904 without rotation of collar 906 can allow for a position of the instrument to be quickly adjusted before it is firmly secured by threading collar 906 distally to a maximum position, as discussed above.

FIG. 10C also shows flat portion 952 of shaft 902, which can include drainage bore 954. Because flat portion 952 does not couple to other components of instrument holder 900, flat portion 952 can be of a small profile relative to shaft 902 to reduce weight of instrument holder 900. Drainage bore 954 can be connected to axial bore 912 (and other internal bores of shaft 902) and can be used for draining fluids from instrument holder 900, for example, during cleaning processes.

FIG. 11A illustrates a perspective view of instrument holder 1100, in accordance with at least one example of this disclosure. FIG. 11B illustrates a perspective view of instrument holder 1100, in accordance with at least one example of this disclosure. FIGS. 11A and 11B are discussed concurrently below.

Instrument holder 1100 can include body 1102, fixed platform 1104, movable platform 1106, stem 1108, actuator 1110, and stem adjuster 1111. Body 1102 can include elongate support 1112 and transverse supports 1114P and 1114D (including bore 1116). Fixed platform 1104 can include straight support 1118, medial support 1120, curved support 1122, which form straight slot 1121 and curved slot 1123, and distal face 1125. Movable platform 1106 can include straight projection 1124 (including proximal face 1127), curved projection 1126 (including proximal face 1129), and support 1128. Stem 1108 can include flange 1130 (including notch 1136), tapered portion 1132, key bit 1134, and stem collar 1135 (including teeth 1139). Actuator 1110 can include knob 1140 and shank 1142 (which can include distal connector 1144). Stem adjuster 1111 can include retainer 1146, biasing element 1148, and stem bolt 1150. Also shown in FIGS. 11A and 11B are axes A1 and A2 and orientation indicators Proximal and Distal.

Instrument holder 1100 can be comprised of materials such as metals, plastics, foams, elastomers, ceramics, composites, and combinations thereof. In some examples, instrument holder 1100 can be comprised of rigid metals such as stainless-steel alloys and titanium for their strength properties and their ability to be cleaned (such as through an autoclave procedure), allowing instrument holder 1100 to be reusable.

Body 1102 can be a rigid or semi-rigid member having a geometric shape substantially of an incomplete cylinder. Body 1102 can include elongate support 1112, which can be similar to an outer wall of body 1102 extending longitudinally along axis A1. Transverse support 1114D can extend from elongate support 1112 to define a substantially cylindrical support or platform at a distal end of body 1102. Transverse support 1114D can include bore 1116, which can extend therethrough along axis A1. Similarly, transverse support 1114P can extend from elongate support 1112 to define a substantially cylindrical support or platform at a proximal end of body 1102.

Fixed platform 1104 can be a rigid or semi-rigid body securable to body 1102 and supported by a distal face of transverse support 1114P. Each of straight support 1118, medial support 1120, and curved support 1122 can be a projection (like a boss or protuberance) extending proximally and axially (along axis A1) from distal face 1125 of platform 1104. Straight support 1118 can form a wedge having a transverse shape that is substantially straight from a distal perspective and can include an inner face that is angled or not parallel with axis A1. Medial support 1120 can form a wedge having a transverse shape that is substantially straight from a distal perspective on a straight side and that is substantially curved on a curved side. Medial support 1120 and can include inner and outer faces that are angled or not parallel with axis A1. Curved support 1122 can form a wedge having a transverse shape that is substantially curved from a distal perspective and can include an inner face that is angled or not parallel with axis A1.

Together, straight support 1118 and medial support 1120 form straight slot 1121, which can be a substantially straight channel from a distal perspective where straight slot 1121 has angled walls (inner face of straight support 1118 and straight face of medial support 1120). Medial support 1120 and curved support 1122 can together form curved slot 1123, which can be a substantially curved channel from a distal perspective where curved slot 1123 has curved and angled walls (inner face of curved support 1122 and curved face of medial support 1120).

Movable platform 1106 can be a rigid or semi-rigid body coupleable to transverse support 1114D and actuator 1110 via shank 1142 of actuator 1110. Each of straight projection 1124 and curved projection 1126 can be a projection (like a boss or protuberance) extending proximally and axially (along axis A1) from a proximal side of movable platform 1106. Straight projection 1124 can form a wedge having a transverse shape that is substantially straight from a proximal perspective and can include inner and outer faces that are angled or not parallel with axis A1, where the faces meet at proximal face 1127, which can be substantially planar and substantially parallel with distal face 1125

Curved projection 1126 can form a wedge having a transverse shape that is substantially curved from a proximal perspective and can include inner and outer faces that are angled or not parallel with axis A1, where the faces meet at proximal face 1129, which can be substantially planar and substantially parallel with distal face 1125. Curved projection 1126 can be fixedly or rigidly coupled to support 1128, where support 1128 can extend radially from curved projection 1126 and radially beyond body 1102 and platforms 1104 and 1106. Support 1128 can include a curved profile. In some examples, support 1128 can be adjustably coupled to curved projection 1126 or can be independently connected to body 1102 to allow for adjustment of support 1128 relative to body 1102, as desired.

Stem 1108 can include flange 1130 (including notch 1136), tapered portion 1132, and key bit 1134, all of which can be consistent with tool 525 discussed above with respect to FIGS. 5A and 5B. Stem 1108 can also include stem collar 1135, which can be an extension of stem 1108 having a geometric shape substantially of a hollow cylinder sized to be aligned with a proximal portion of transverse support 1114P and body 1102. In some examples, stem collar 1135 can be removably coupled to transverse support 1114P. For example, teeth 1133, which can be proximally extending teeth (such as sharp projections) can engage teeth 1139, which can be distally extending teeth (such as sharp projections). When teeth 1133 are engaged with teeth 1139, rotation of stem collar 1135 can be prevented to retain an orientation of stem relative to body 1102.

Actuator 1110 can be operably connected to a distal portion of body 1102 such that knob 1140 is secured to shank 1142 (which can include distal connector 1144). Shank 1142 can be secured to a proximal portion of knob 1140 and can extend through transverse support 1114D so that distal connector 1144 can be secured to movable support 1106. Knob 1140 can be a manually adjustable knob with lobes and/or grooves disposed around a radially outer surface of knob 1140 configured to improve grip and ergonomics.

Stem adjuster 1111 can be operably connected to a proximal portion of stem 1108 and transverse support 1114P. Retainer 1146 can be a disk or knob threadably coupleable to stem bolt 1150. Stem bolt 1150 can be fixedly secured to transverse support 1114P in some examples and can be threadably secured to a proximal portion of transverse support 1114P in other examples.

Biasing element 1148 can be a resilient element, such as a spring, disposable between retainer 1146 and stem collar 1135 and/or transverse support 1114P. In some examples, biasing element 1148 can be a wave compression spring. In other examples, biasing element 1148 can be other springs or resilient members, such as a compression spring or compressible and resilient members comprised of resilient materials such as rubbers, plastic, and the like.

In operation of some examples, knob 1140 of actuator 1110 can be turned about axis A1 to translate movable platform 1106 distally, away from platform 1104 so that straight channel 1121 and curved channel 1123 are open. An instrument can then be placed in either channel and knob 1140 can be turned (in the opposite direction) about axis A1 to translate movable platform 1106 proximally. During translation, straight projection 1124 and curved projection 1126 can translate into straight channel 1121 and curved channel 1123, respectively, to make the openings of each of straight channel 1121 and curved channel 1123 smaller and so that either of proximal faces 1127 and 1129 engages the instrument together with distal face 1125 of platform 1104. When a desired hold on the instrument is achieved, a user can cease turning knob 1140 and the instrument can be held in place relative to instrument holder 1100.

When straight projection 1124 extends into straight channel 1121, the angled faces of straight projection 1124 can be complimentary to the inner face of straight support 1118 and straight face of medial support 1120 to allow for straight channel 1121 to reduce to a relatively very small opening, helping to reduce movement of the supported instrument and straight projection 1124 relative to channel 1121. Similarly, the angled faces of curved projection 1126 can be complimentary to the inner face of curved support 1122 and/or curved face of medial support 1120 to allow for curved channel 1123 to reduce to a relatively very small opening, helping to reduce movement of the supported instrument and curved projection 1126 relative to channel 1123.

In operation of some examples, when a position of stem 1108 is desired to be adjusted, retainer 1146 can be unthreaded from bolt 1150 so that stem collar 1135 can be disengaged from retainer 1146 and from transverse support 1114P. Stem 1108 can then be rotated about axis A1 to another position, for example so that stem 1108 extends along axis A2, as shown in FIG. 11B. However, stem 1108 can be positioned along any axis substantially orthogonal to axis A1. Retainer 1146 can be rethreaded to bolt 1150 to clamp stem collar 1135 between retainer 1146 and transverse support 1114P to retain the desired position of stem 1108 relative to transverse support 1114P.

FIG. 11C illustrates a focused perspective view of a portion of instrument holder 1100 with stem 1108 removed, in accordance with at least one example of this disclosure. Instrument holder 1100 can include body 1102 (including transverse support 1114P), platform 1104, and stem adjuster 1111. Platform 1104 can include straight support 1118, medial support 1120, and curved support 1122. Stem adjuster 1111 can include retainer 1146, biasing element 1148, and stem bolt 1150. Transverse support 1114P can include can include teeth 1133. Straight support 1118 can include inner face 1160, medial support 1120 can include straight face 1162 and curved face 1164, and curved support 1122 can include curved face 1166. FIG. 11C also shows axis A1.

Instrument holder 1100 of FIG. 11C can be consistent with instrument holder 1100 of FIGS. 11A and 11B above. FIG. 11C shows additional details of instrument holder 1100, such as faces of straight support 1118, medial support 1120, and curved support 1122. Each of inner face 1160, straight face 1162, curved face 1164, and curved face 1166 can be angled relative to axis A1 such that inner face 1160 and straight face 1162 together form a substantially V-shape or U-shape of straight channel 1121 and such that curved face 1164 and curved face 1166 form a substantially V-shape or U-shape of curved channel 1123.

FIG. 11C also shows how biasing element 1148 can be disposed within a counterbore of stem collar 1135 such that biasing element 1148 can engage stem collar 1135 and retainer 1146 to bias retainer 1146 away from stem collar 1135 to separate teeth 1133 from teeth 1139 to allow for rotation of stem collar 1135 relative to body 1102.

Figure 11D:
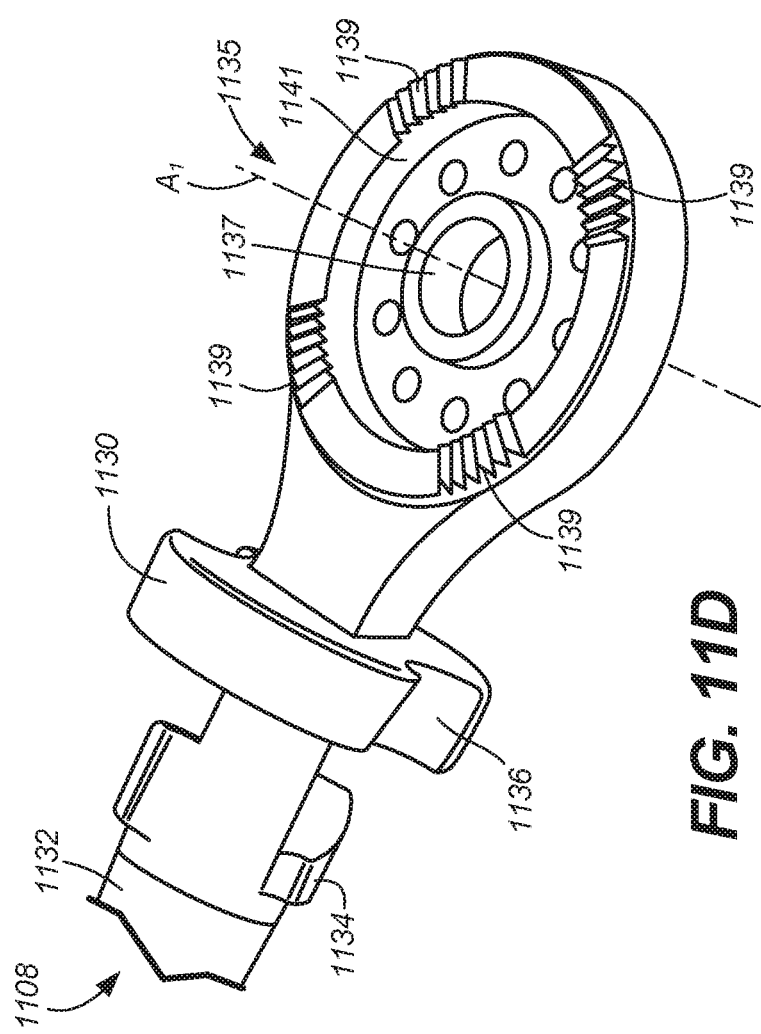
FIG. 11D illustrates a focused perspective view of a portion of an instrument holder, in accordance with at least one example of this disclosure.

FIG. 11D illustrates a focused perspective view of a portion of stem 1108, in accordance with at least one example of this disclosure. Stem 1108 can include flange 1130 (including notch 1136), tapered portion 1132, key bit 1134, and stem collar 1135. Stem collar 1135 can include bolt bore 1137, teeth sets 1139, and counterbore 1141. Also shown in FIG. 11D is axis A1.

Bolt bore 1137 can be a bore extending axially (along axis A1) through stem collar 1135 where bolt bore 1137 can be sized to receive bolt 1150 of retainer 1111 therethrough in a non-threaded interface so that collar 1135 is free to rotate relative to bold 1150 when bolt 1150 extends through bolt bore 1137.

Each of teeth sets 1139 can be sets of teeth disposed around a periphery of collar 1135 and can include teeth that extend axially therefrom. Each of the teeth of teeth sets 1139 can be configured to engage teeth 1133 disposed on a proximal side of platform transverse support 1114P. Counterbore 1141 can be a bore extending axially in to stem collar 1135 and can have an axial length configured to retain biasing element 1148 partially therein.

FIG. 12A illustrates a perspective view of instrument holder 1100, in accordance with at least one example of this disclosure. FIG. 12B illustrates a perspective view of instrument holder 1100 and instrument 1200, in accordance with at least one example of this disclosure. FIG. 12C illustrates a perspective view of instrument holder 1100 and instrument 1200, in accordance with at least one example of this disclosure. FIGS. 12A-12C are discussed below concurrently.

The components of instrument holder 1100 of FIGS. 12A-12B can be consistent with the components of instrument holder 1100 of FIGS. 11A-11D, except that stem 1108 of instrument holder 1100 of FIGS. 12A-12B may be fixed and may not include stem adjuster 1111.

Also, FIGS. 12A-12B show instrument 1200 in multiple installed conditions. Instrument 1200 can include first arm 1202 and second arm 1204. First arm 1204 can include first handle 1206 and first finger support 1208. Second arm 1204 can include second handle 1212 and second finger support 1210. Handles 1206 and 1212 can be long and substantially straight portions of instrument 1200. In some examples, handles 1206 and 1212 can be cylindrical. In other examples, handles 1206 and 1212 can have a rectangular prismatic shape. Finger supports 1208 and 1210 can have a geometric shape that is substantially ring like and that can include a round or other prismatic profile. In some examples, instrument 1200 can be forceps.

In operation of some examples, knob 1140 of actuator 1110 can be turned about axis A1 to rotate shank 1142 (through bore 1116 of transverse support 1114D) to translate movable platform 1106 distally, away from platform 1104 so that straight channel 1121 and curved channel 1123 are open, as shown in FIG. 12A. When straight channel 1121 and curved channel 1123 are open an instrument can then be placed in either channel.

For example, handle 1206 can be placed in straight channel 1121, as shown in FIG. 12B. Knob 1140 can then be turned (in the opposite direction of opening) about axis A1 to translate movable platform 1106 proximally. During translation, straight projection 1124 can translate into straight channel 1121 to make the opening of straight channel 1121 smaller and so that handle 1206 of instrument 1200 is clamped between straight projection 1124, straight support 1118 and medial support 1120. When a desired hold on instrument 1200 is achieved, a user can cease turning of knob 1140 and instrument 1200 can be held in place relative to instrument holder 1100.

Also, in some examples, when straight channel 1121 and curved channel 1123 are open, finger support 1208 can be placed in curved channel 1123. Knob 1140 can then be turned (in the opposite direction of opening) about axis A1 to translate movable platform 1106 proximally. During translation, curved projection 1126 can translate into curved channel 1123 to make the opening of curved channel 1123 smaller and so that finger support 1208 of instrument 1200 is clamped between curved projection 1126, medial support 1120, and curved support 1122. When a desired hold on instrument 1200 is achieved, a user can cease turning of knob 1140 and instrument 1200 can be held in place relative to instrument holder 1100.

While instrument 1200 is retained within straight channel 1121, a proximal portion of support 1128 can engage a distal side of finger support 1208 (or another portion of instrument 1200) to limit rotation of instrument 1200 relative to instrument support 1100. Similarly, while instrument 1200 is retained within curved channel 1123, a proximal portion of support 1128 can engage a distal side of finger support 1208 (or another portion of instrument 1200) to limit rotation of instrument 1200 relative to instrument support 1100.

While instrument 1200 is held in place by instrument holder 1100 in either straight channel 1121 or curved channel 1123, as discussed above, a user can still operate instrument 1200. For example, when instrument 1200 is retained within straight channel 1121, as shown in FIG. 12B, a user can operate instrument 1200 using finger supports 1208 and 1210 as arm 1204 is free to move relative to from 1202 and both of finger supports 1208 and 1210 are clear of instrument holder 1100.

When instrument 1200 is retained within curved channel 1123, as shown in FIG. 12C, it may be difficult for a user to interface with finger support 1208 while it is clamped by instrument holder 1100. In such a case, a user can operate instrument 1200 using finger support 1210 and support 1128 of instrument holder 1100. In some examples, support 1128 can be repositioned to achieve a desired grip or hold on finger support 1210 and/or support 1128.

Figure 13:
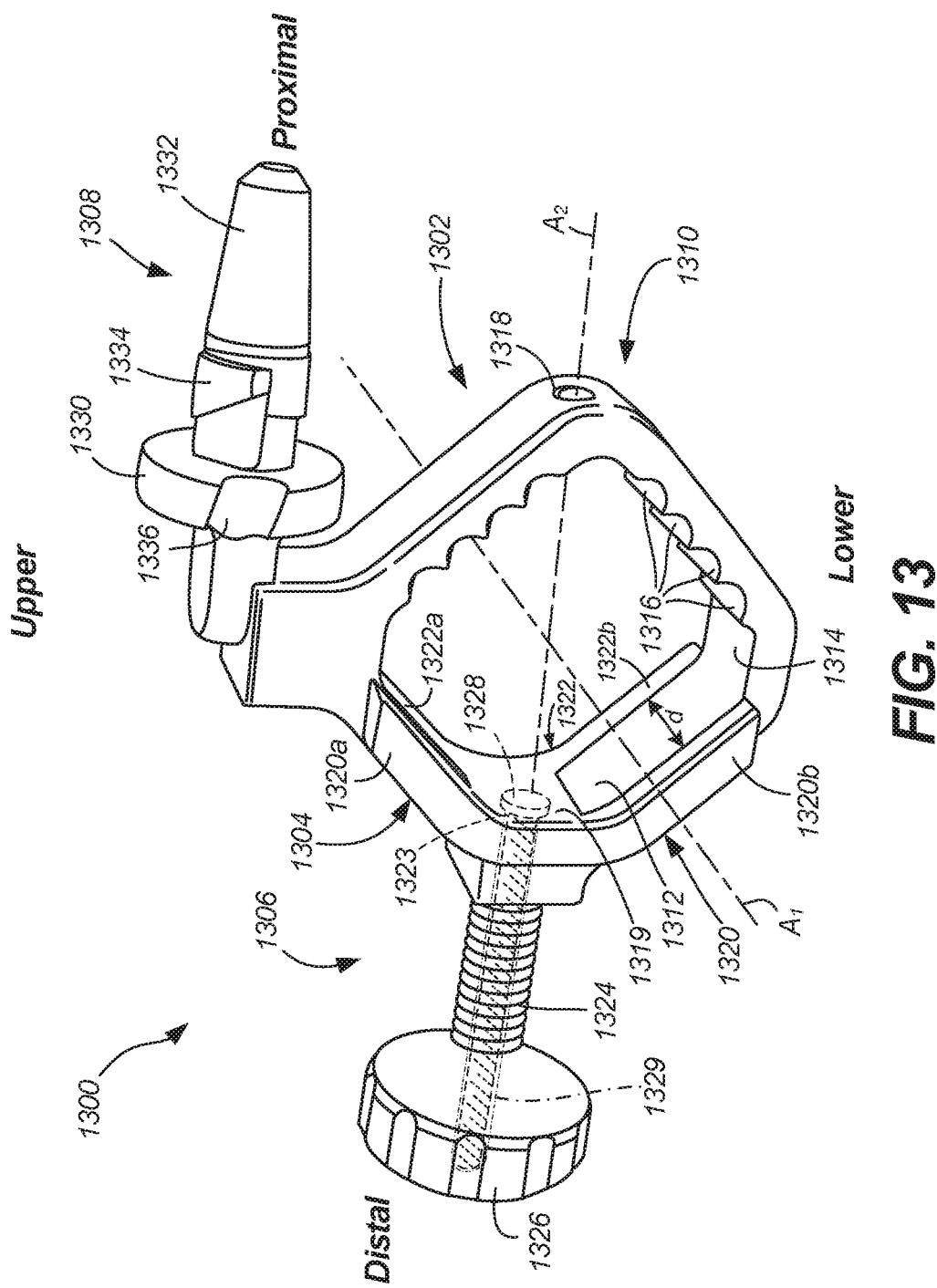
FIG. 13 illustrates a perspective view of an instrument holder, in accordance with at least one example of this disclosure.

FIG. 13 illustrates a perspective view of instrument holder 1300, in accordance with at least one example of this disclosure. Instrument holder 1300 can include body 1302, jaw 1304, actuator 1306, and stem 1308. Body 1302 can include proximal portion 1310 and distal portion 1312. Body 1302 and jaw 1304 can together define retaining bore 1314. Proximal portion 1310 can include serrations 1316 and assembly bore 1318. Jaw 1304 can include jaw body 1319, first arm 1320 (including upper finger 1320a and lower finger 1320b), and second arm 1322 (including upper finger 1322a and lower finger 1322b). Actuator 1306 can include shank 1324, handle 1326, fastener 1328, and fastener bore 1329. FIG. 13 also shows distance d, axes A1 and A2 and orientation indicators Proximal, Distal, Upper, and Lower.

Instrument holder 1300 can be comprised of materials such as metals, plastics, foams, elastomers, ceramics, composites, and combinations thereof. In some examples, instrument holder 1300 can be comprised of rigid metals such as stainless-steel alloys and titanium for their strength properties and their ability to be cleaned (such as through an autoclave procedure), allowing instrument holder 1300 to be reusable.

Body 1302 can be a rigid or semi-rigid body having a geometric shape substantially of a hollow rectangular prism (or diamond prism) with a small height relative to length and width. Proximal portion 1310 can comprise about one half of body 1302 on a proximal side (including two sides or walls) and distal portion 1312 can comprise about one half of body 1302 on a distal side (including two other sides or walls). Proximal portion 1310 can include serrations 1316, which can be steps or projections, on a radially inner side of proximal portion 1310, where serrations 1316 can face jaw 1304. Assembly bore 1318 can extend through proximal portion 1310 and can be coaxial with axis A2. Body 1302 and jaw 1304 can define retaining bore 1314 in a diamond shape, in some examples.

Jaw 1304 can be a translatable and rigid (or semi-rigid) member partially disposable within body 1302. Jaw body 1319 can comprise a substantially central portion of jaw 1304 from which first arm 1320 and second arm 1322 can extend parallel to each other and can be separated by distance d. Distance d between arms can be slightly larger than an axial length of body 1302 in some examples.

Jaw 1304 can have a geometric shape substantially of an H in a plane that is substantially parallel to axis A1 and substantially perpendicular to axis A2 and can have a geometric shape substantially of a V in a plane that is transverse to axis A1 and substantially parallel to axis A2. That is, first arm 1320 can extend transversely to the axes A1 and A2 and can be shaped complementary to distal portion 1320 of body 1302 and can extend partially axially outward from body 1302. Upper finger 1320a of second arm 1322 can extend toward an upper portion of body 1302 and lower finger 1320b can extend toward a lower portion of body 1302.

Second arm 1322 can extend transversely to the axes A1 and A2 and can be shaped complementary to distal portion 1312 of body 1302 and can extend partially axially outward from body 1302 on axially opposite side of first arm 1320. Upper finger 1322a of second arm 1322 can extend toward an upper portion of body 1302 and lower finger 1322b can extend toward a lower portion of body 1302. First arm 1320 and second arm 1322 can extend from the jaw body transversely to the axes A1 and A2 in two separate directions.

Actuator 1306 can be a rotatable and translatable rigid member coupleable to jaw 1304 and body 1302. Shank 1324 can be an elongate member extending along axis A2 and can be threadably engaged with distal portion 1312 of body 1302. Handle 1326 can be a handle, knob, and the like coupled to a distal portion of shank 1324. Handle 1326 can be rotatable to rotate shank 1324. Fastener bore 1329 can threadably receive shank 1324 and handle 1326 at a substantially central portion of each along axis A2. Fastener 1328 can be an elongate member extending along axis A2 and can be secured to body 1319 of jaw 1304 through bore 1323 of body 1319 and can be secured to shank 1324 and handle 1326 through fastener bore 1329.

Stem 1308 can be a portion of body 1302 coupleable to a surgical arm through an end effector coupler (such end effector coupler 500 above). In some examples, stem 1308 can extend along an axis substantially parallel with axis A2. Stem 1308 can include flange 1330 (including notch 1336), tapered portion 1332, and key bit 1334, all of which can be consistent with tool 525 discussed above with respect to FIGS. 5A and 5B.

In assembly of some examples, jaw 1304 can be inserted into body 1302 and can be positioned to engage distal portion 1312 of body 1302. Shank 1324 of actuator 1306 can then be threaded into body 1302 (and can optionally engage a distal portion of body 1319 of jaw 1304) using handle 1326. Fastener 1328 can be passed through assembly bore 1318 of proximal portion and through bore 1323 of body 1319 to be threaded into fastener bore 1329 of shank 1324 and handle 1326. Fastener 1328 can be threaded into jaw body 1329 in some examples and can be retained against a proximal side of jaw body 1329 in some examples by a head of fastener 1328 such that fastener 1328 is free to spin relative to jaw 1304. In other examples, fastener 1328 can be a pin securable to handle 1326 through an interference engagement. In other examples, other types of fasteners can be used.

Once assembled, actuator 1306 can be rotated by rotating handle 1326 to rotate shank 1324. Because shank 1324 is threadably engaged with distal portion 1312 of body 1302, rotation of actuator 1306 causes translation of shank 1324 relative to body 1302 along axis A2. And, because shank 1324 is coupled to jaw 1304 through fastener 1328, translation of shank 1324 causes translation of jaw 1304 where distal-to-proximal translation of jaw 1304 causes retainer bore 1314 to become smaller as jaw 1304 approaches proximal portion 1310 of body 1302. The size of retainer bore 1314 can be adjusted, using actuator 1306, to retain a tool or instrument in retainer bore 1314 between serrations 1316 and arms 1320 and 1322. In some examples, because arms 1320 and 1322 are spaced by distance d wider than an axial length (along axis A1) of body 1302, retainer bore 1314 can be the size of the entire opening of body 1302 and can be made relatively small because arms 1320 and 1322 do not contact proximal portion 1310 of body 1302. Because the size of retainer bore 1314 is relatively largely variable, instrument holder 1300 can be used to retain instruments of a variety of shapes and sizes.

In some examples, translation of jaw 1304 can be proximally limited through contact of body 1319 with proximal portion 1310 or through contact of handle 1326 with distal portion 1320 of body 1302.

FIG. 14A illustrates a perspective view of instrument holder 1300A in a first condition, in accordance with at least one example of this disclosure. FIG. 14B illustrates a perspective view of instrument holder 1300A in a second condition, in accordance with at least one example of this disclosure. FIGS. 14A and 14B are discussed below concurrently.

Instrument holder 1300A can be consistent with instrument holder 1300 discussed above with respect to FIG. 13, except that stem 1308 of instrument holder 1308 can extend along axis A3 (as shown in FIG. 14A) which can be substantially parallel with axis A1. Also, FIG. 14A shows jaw 1304 in a fully open position and FIG. 14B shows jaw 1304 in a closed or partially-closed position where jaw 1304 is translated proximally. Also, FIG. 14B shows actuator bore 1327 which shank 1324 can threadably engage.

Figure 15B:
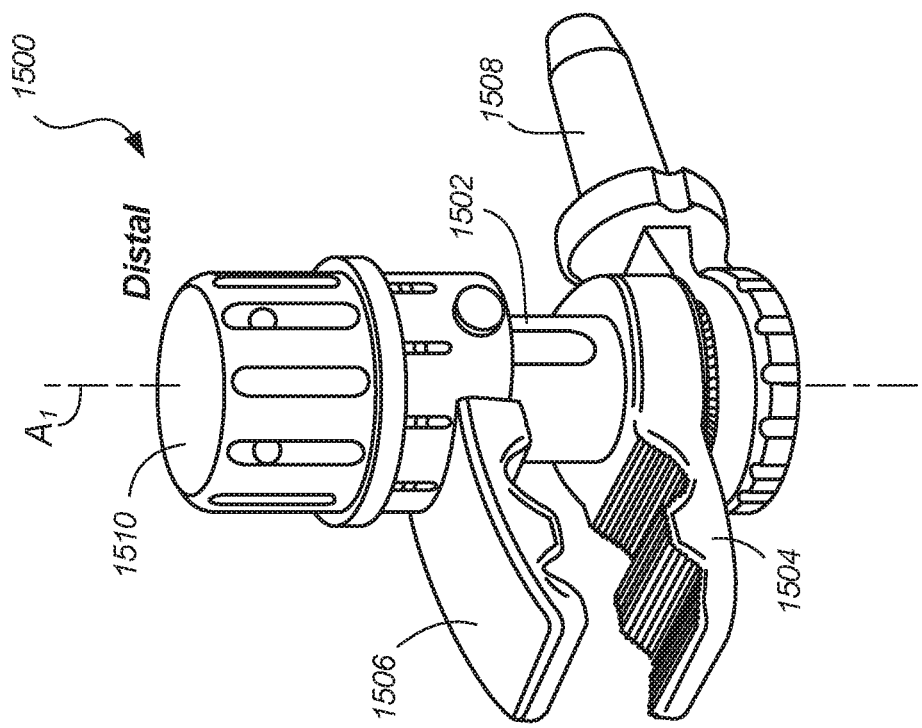
FIG. 15B illustrates a perspective view of an instrument holder in a second condition, in accordance with at least one example of this disclosure.
Figure 15A:
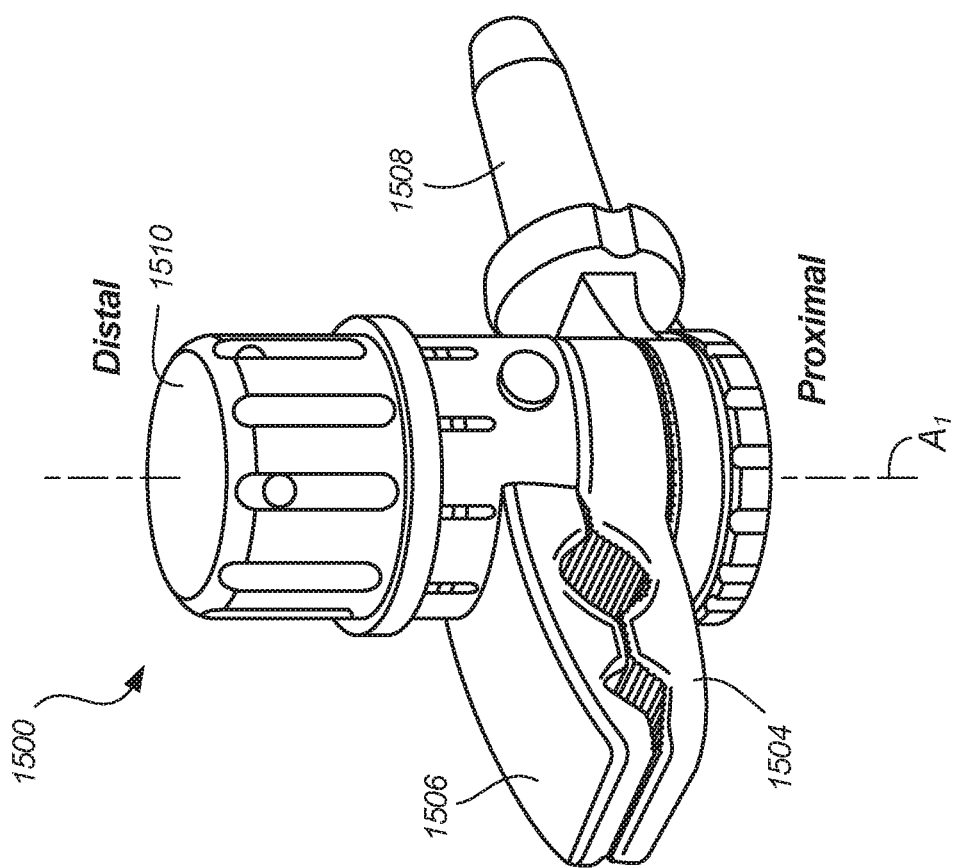
FIG. 15A illustrates a perspective view of an instrument holder in a first condition, in accordance with at least one example of this disclosure.

FIG. 15A illustrates a perspective view of instrument holder 1500 in a first condition, in accordance with at least one example of this disclosure. FIG. 15B illustrates a perspective view of instrument holder 1500 in a second condition, in accordance with at least one example of this disclosure. FIGS. 15A and 15B are discussed below concurrently.

Instrument holder 1500 can include body 1502 (only visible in FIG. 15B), first platform 1504, second platform 1506, stem 1508, and actuator 1510. Also shown in FIGS. 15A and 15B are axis A and orientation indicators Proximal and Distal.

Instrument holder 1500 can be comprised of materials such as metals, plastics, foams, elastomers, ceramics, composites, and combinations thereof. In some examples, instrument holder 1500 can be comprised of rigid metals such as stainless-steel alloys and titanium for their strength properties and their ability to be cleaned (such as through an autoclave procedure), allowing instrument holder 1500 to be reusable.

Body 1502 can be a rigid or semi-rigid body having a geometric shape substantially of a cylinder extending along axis A1. First platform 1504 can be a rigid or semi-rigid member fixedly (or removably) coupleable to a proximal portion of body 1502, where first platform 1504 can extend radially therefrom. As discussed further below, first platform 1504 can include grooves. Second platform 1506 can be a rigid or semi-rigid member fixedly (or removably) coupleable to body 1502 in an orientation opposing first platform 1506, where first platform 1504 and second platform 1506 together include structure to retain instruments, such as standard surgical instruments.

Stem 1508 can be a portion of body 1502 or can be an independent component coupleable to body 1502. Stem 1508 can also be coupleable to a surgical arm through an end effector coupler (such end effector coupler 500 above). In some examples, stem 1508 can extend along an axis substantially transverse with axis A1.

Actuator 1510 can be a rigid member coupleable to body 1502 at a distal portion of body 1502. Actuator 1510 can be engaged with second platform 1506 such that actuator 1510 and platform 1506 can move together with respect to body 1502.

In operation of some examples, stem 1508 can be connected to an end effector coupler to secure instrument holder 1500 to a surgical arm. Actuator 1510 can then be operated (rotated) to translate actuator 1510 and second platform 1506 distally (away from first platform 1504). Once the retaining features of the platforms reach a desired size, an instrument can be inserted between first platform 1504 and second platform 1506 and actuator 1510 can again be operated, but this time to translate second platform 1506 proximally, towards first platform 1504, to secure the instrument between first platform 1504 and second platform 1506. In this way, instrument holder 1500 can be used to secure standard instruments to an end effector coupler and a surgical arm. Further features and operations of instrument holder 1500 are discussed below with respect to FIGS. 16A-16C.

Figure 16A:
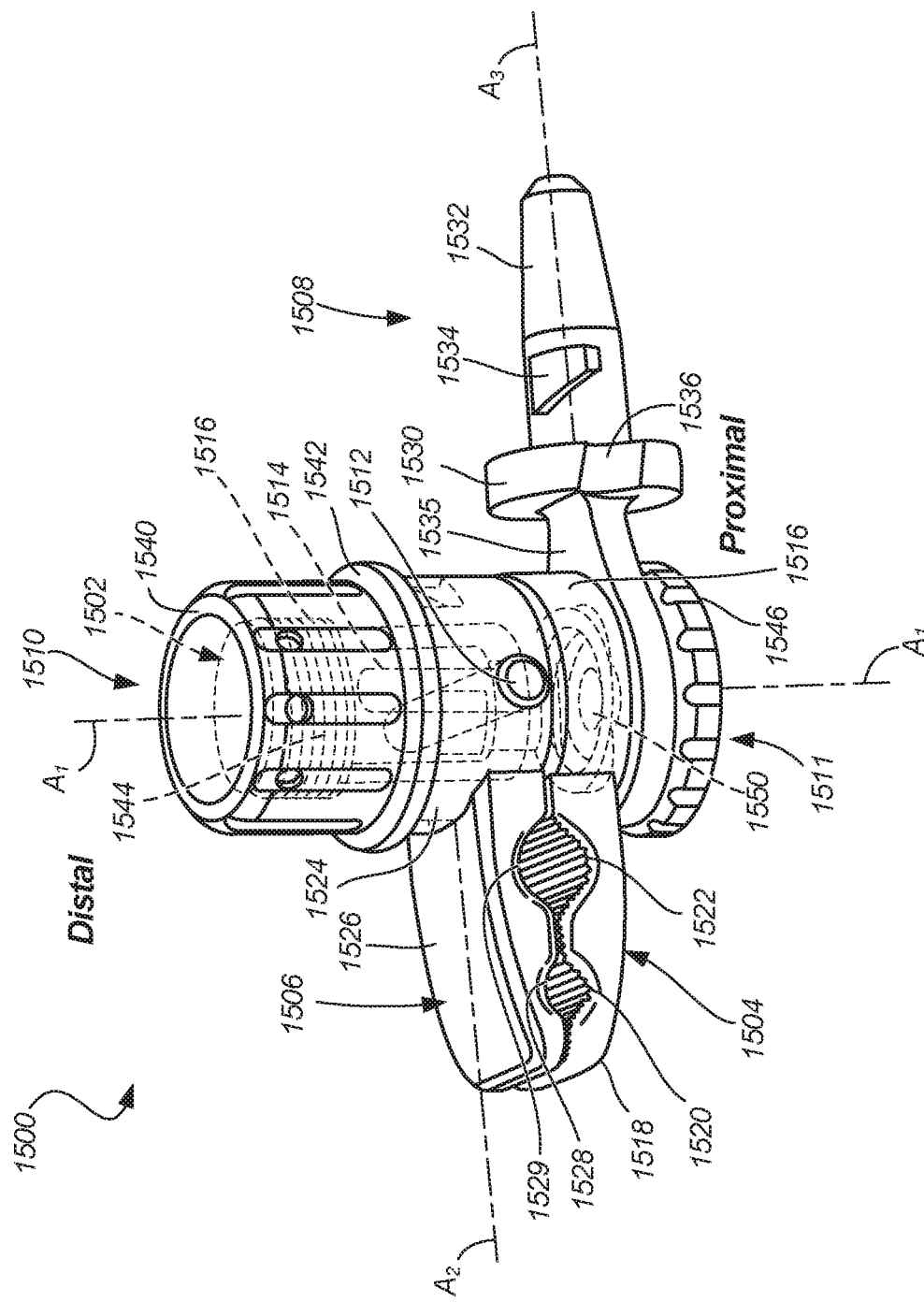
FIG. 16A illustrates a perspective view of an instrument holder, in accordance with at least one example of this disclosure.

FIG. 16A illustrates a perspective view of instrument holder 1500, in accordance with at least one example of this disclosure. FIG. 16B illustrates a perspective view of instrument holder 1500, in accordance with at least one example of this disclosure. FIG. 16C illustrates a perspective view of instrument holder 1500, in accordance with at least one example of this disclosure. FIGS. 16A-16C are discussed below concurrently.

Instrument holder 1500 can include body 1502, first platform 1504, second platform 1506, stem 1508, actuator 1510, stem adjuster 1511, and pin 1512. Body 1502 can include slot 1514 and male threaded portion 1516. First platform 1504 can include first collar 1516, first radial extension 1518, first small groove 1520 (or notch), and first large groove 1522 (or notch). Second platform 1506 can include second collar 1524, second radial extension 1526, second small groove 1528 (or notch), and second large groove 1529 (or notch). Stem 1508 can include flange 1530 (including notch 1536), tapered portion 1532, key bit 1534, and stem collar 1535. Actuator 1510 can include knob 1540, which can include flange 1542 and female threaded portion 1544. Stem adjuster 1511 can include retainer 1546, biasing element 1548, and stem bolt 1550. Also shown in FIGS. 16A and 16B are axes A1, A2, and A3 and orientation indicators Proximal and Distal and also shown in FIG. 16C are axes A1, A2, and A4 and orientation indicators Proximal and Distal.

Instrument holder 1500 of FIGS. 16A-16C can be consistent with instrument holder 1500 of FIGS. 15A and 15B; however, FIGS. 16A-16C show additional components and details of instrument holder 1500.

For example, slot 1514 can be a slot extending through an outer wall of body 1502 and extending axially parallel to axis A1. In some examples, body 1502 can include two of slots 1514 on opposing sides of body 1502. In other examples, fewer or more slots may be used. Male threaded portion 1516 can be located on a distal portion of body 1502 and can extend to a distal end of body 1502. Male threaded portion 1516 can be sized to receive female threaded portion 1544 of cap 1540.

First collar 1516 can be an extension of first platform 1504 having a geometric shape substantially of a hollow cylinder sized to be disposed on body 1502 and fixedly secured thereto. First radial extension 1518 can be an extension of first platform 1504 extending radially outward from first collar 1516 and can include first small groove 1520 and first large groove 1522. Each of first small groove 1520 and first large groove 1522 can have a substantially V-shape and can extend transversely to a radius of body 1502. In some examples, first small groove 1520 can be smaller than first large groove 1522. In other examples, first small groove 1520 and first large groove 1522 can be of substantially the same size or first small groove 1520 can be larger than first large groove 1522. In each example, first small groove 1520 and first large groove 1522 can include teeth, serrations, or ridges to increases friction between first platform 1504 and an instrument.

Second collar 1524 (which can include pin bores 1525) can be an extension of second platform 1506 having a geometric shape substantially of a hollow cylinder sized to be disposed on body 1502 and translatable thereon. Second radial extension 1526 can be an extension of second platform 1506 extending radially outward from second collar 1524 and can include second small groove 1528 opposing first small groove 1520 and second large groove 1529 opposing first large groove 1522. Each of second small groove 1528 and second large groove 1528 can have a substantially V-shape and can extend transversely to a radius of body 1502. In some examples, second small groove 1528 can be smaller than second large groove 1529. In other examples, second small groove 1528 and second large groove 1529 can be of other sizes. In each example, second small groove 1528 and second large groove 1529 can include teeth, serrations, or ridges to increases friction between second platform 1506 and an instrument.

Pin 1512 can be a rigid member passing through bores 1525 of second collar 1524 of second platform 1506. Pin 1512 can also pass through slots 1514 of body 1502 to retain pin 1512 within body 1502 and to secure second platform 1506 to body 1502. The size and shape of slots 1514 can restrict translation of pin 1512 axially (along axis A1) and therefore can restrict translation of second platform 1504 relative to body 1502.

Flange 1530 (including notch 1536), tapered portion 1532, and key bit 1534 of stem 1508 all can be consistent with tool 525 discussed above with respect to FIGS. 5A and 5B. Further, Stem 1508 can include stem collar 1538 which can be an extension of stem 1508 having a geometric shape substantially of a hollow cylinder sized to be disposed on body 1502 and can be translatable and rotatable thereon.

Knob 1540 can be a rigid member having geometric shape substantially of a cap or of a hollow cylinder closed on a distal end. Knob 1540 can include axial slots for cleaning and for purchase or grip. Knob 1540 can also include flange 1542 extending radially from a proximal portion of knob 1540, which can engage tabs 1541 (shown in FIG. 16C) of a distal portion of second collar 1524 of second platform 1506. Tabs 1541 can also include protrusions extending radially inward to secure collar 1524 to flange 1542 of knob 1540. The engagement between tabs 1541 and knob 1540 can secure collar 1524 to knob 1540 while still allowing knob 1540 to rotate about axis A without causing rotation of second platform 1506 relative to body 1502 and first platform 1504. Knob 1540 further includes female threaded portion 1544, which can be configured to engage male threaded portion 1516 of body 1502.

Stem adjuster 1511 can be a series of components configured to adjust a position of stem 1508 relative to body 1502 (and therefore to platforms 1504 and 1506). Retainer 1546 can be a rigid member including a knurled or channeled exterior surface. Retainer 1546 can include stem bolt 1550 that can be securable to body 1502. Biasing element 1548 can be a spring or other resilient element disposable between retainer 1546 and stem collar 1535. In some examples, a distal portion of first collar 1516 can include teeth 1552, which can be engageable with teeth of stem collar 1535 to prevent rotation of stem 1508 relative to body 1502 and first platform 1504 when retainer 1546 has been tightened to stem bolt 1550. Operation of stem adjuster 1511 can be consistent with stem adjuster 1211 of instrument holder 1200, discussed above with respect to FIGS. 11A-11C.

In operation of some examples, instrument holder 1500 can be coupled to an end effector coupler and surgical arm as discussed above with respect to FIGS. 5A and 5B. In other examples, instrument holder 1500 can be secured to the surgical arm after an instrument is secured to instrument holder 1500. To secure an instrument to instrument holder 1500, knob 1540 of actuator 1510 can be rotated about axis A1 to translate knob 1540 and second platform 1506 distally (away from first platform 1504). Once the openings formed between first small groove 1520 and second small groove 1528 and/or between first large groove 1522 and second large groove 1529 are large enough to receive the tool or instrument, the instrument can be inserted into one or more of the openings.

Knob 1540 can then be rotated about axis A1 (in a direction opposite the opening direction, for example, clockwise from a distal perspective) to thread female threaded portion 1544 further on to male threaded portion 1516 to translate second platform 1506 proximally toward first platform 1504. Proximal translation of second platform 1506 can be guided by pin 1512 riding within slots 1514 of body 1502 and proximal translation can be limited by contact between pin 1512 and slots 1514 and/or contact between the instrument and platforms 1504 and 1506. Because pin 1512 passes through two of slots 1514 of body 1502 rotation of second platform 1506 relative to first platform 1504 and body 1502 is limited.

When second platform 1506 has been translated proximally to a desired position, for example when the openings formed between first small groove 1520 and second small groove 1528 and/or between first large groove 1522 and second large groove 1529 are small enough to retain the instrument, rotation of knob 1540 can be stopped and the instrument can be retained between platforms 1504 and 1506. Because sizes of the openings formed between first small groove 1520 and second small groove 1528 and/or between first large groove 1522 and second large groove 1529 are selectable through actuation of knob 1540, a variety of instruments can be retained by instrument holder 1500.

When adjustment of a position of the instrument is desired or when removal of the instrument is desired, platforms 1504 and 1506 can be separated again, as discussed above. In this way, instrument holder 1500 can be reusable.

As discussed above, retainer 1546 of stem adjuster 1511 can be used to adjust a position of stem 1508 relative to body 1502. For example, retainer 1546 can be used to move stem 1508 to align with axis A3 (which can be substantially parallel with axis A2), as shown in FIGS. 16A and 16B. Retainer 1546 can be loosened and stem 1508 can me moved to align with axis A4 (which can be substantially orthogonal with axis A2), as shown in FIG. 16C. Stem 1508 can positioned to be in other positions as well.

Figures 17A, 17B:
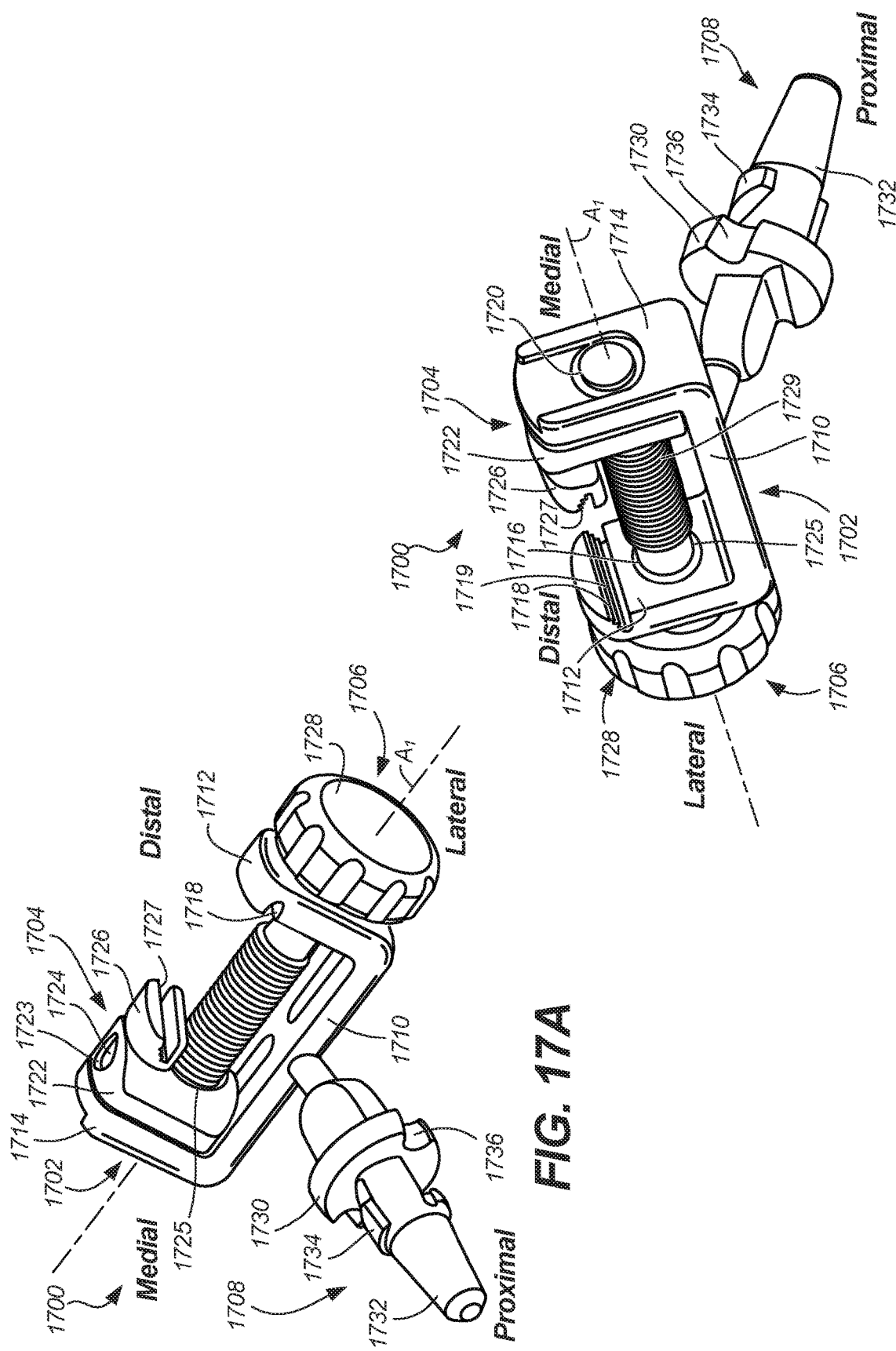
FIG. 17A illustrates a perspective view of an instrument holder, in accordance with at least one example of this disclosure.
FIG. 17B illustrates a perspective view of an instrument holder, in accordance with at least one example of this disclosure.

FIG. 17A illustrates a perspective view of instrument holder 1700, in accordance with at least one example of this disclosure. FIG. 17B illustrates a perspective view of instrument holder 1700, in accordance with at least one example of this disclosure. FIG. 17C illustrates a perspective view of instrument holder 1700, in accordance with at least one example of this disclosure.

Instrument holder 1700 can include body 1702, movable support 1704, actuator 1706, and stem 1708. Body 1702 can include base 1710, lateral upright 1712, and medial upright 1714. Lateral upright 1712 can include lateral bore 1716 (only visible in FIG. 17B) and fixed jaw slot 1718 (including teeth 1719). Medial upright 1714 can include medial bore 1720 (only visible in FIG. 17B). Movable support 1704 can include movable body 1722 (including pivot bore 1723 and shaft bore 1725), pin 1724, and pivotable jaw 1726 (including pivotable jaw slot 1727). Actuator 1706 can include handle 1728 and threaded shaft 1729. Stem 1708 can include flange 1730 (including notch 1736), tapered portion 1732, and key bit 1734. Also shown in FIGS. 17A-17C are axis A1 and orientation indicators Proximal, Distal, Medial, and Lateral Instrument holder 1700 can be comprised of materials such as metals, plastics, foams, elastomers, ceramics, composites, and combinations thereof. In some examples, instrument holder 1700 can be comprised of rigid metals such as stainless-steel alloys and titanium for their strength properties and their ability to be cleaned (such as through an autoclave procedure), allowing instrument holder 1700 to be reusable.

Body 1702 can be a rigid or semi-rigid body having a geometric shape substantially of a U. Each of base 1710, lateral upright 1712, and medial upright 1714 can have substantially rectangular prismatic geometric shapes. However, each of base 1710, lateral upright 1712, and medial upright 1714 can have other shapes in other examples. Base 1710 can extend substantially longitudinally parallel to axis A1 and can connect to lateral upright 1712 at a lateral end of base 1710 and can connect to medial upright 1714 at a medial end of base 1710. Lateral upright 1712 and medial upright 1714 can each extend from base 1710 substantially in parallel to each other and substantially transversely to axis A1.

Lateral bore 1716 can be a bore extending through lateral upright 1712 substantially parallel to axis A1. Medial bore 1720 can be a bore extending through medial upright 1714 substantially parallel to axis A1 where medial bore 1720 can be substantially coaxial with lateral bore 1716.

Fixed jaw slot 1718 can be proximate a distal end (or a cantilevered end) of lateral upright 1712. Fixed jaw slot 1718 can be a slot in a medial face of lateral upright 1712 extending substantially transverse to axis A1 and substantially transverse to a cantilever direction of lateral upright 1712. Fixed jaw slot 1718 can comprise a geometric shape substantially of an asymmetric V, but can have a U-shape, V-shape, or other shape in other examples. In some examples, fixed jaw slot 1718 can include teeth or steps.

Movable body 1722 can be a rigid member having a profile similar to that of medial upright 1714 and/or lateral upright 1716, but movable body 1722 can be a separate component from body 1702. Shaft bore 1725 can be a threaded bore extending through movable body 1722 substantially parallel to axis A1 where shaft bore 1725 can be substantially coaxial with lateral bore 1716 and medial bore 1720. Pivot bore 1723 can be a bore extending substantially transversely to shaft bore 1725 and can extend partially through movable body 1722. Pivot bore 1723 can be sized to receive pin 1724 therein. Pin 1724 can be a rigid fastener, such as a pin, rivet, screw, and the like, configured to secure pivotable jaw 1726 to movable body 1722. In some example, pivotable jaw 1726 can be pivotably coupled to movable body 1722 using pin 1724. In some examples, pivotable jaw 1726 can include pivotable jaw slot 1727, which can extend into pivotable jaw 1726 from a lateral side of pivotable jaw 1726. Pivotable jaw slot 1727 can comprise a geometric shape substantially of an asymmetric V, but can have a U-shape, V-shape, or other shape in other examples. In some examples, pivotable jaw slot 1727 can include teeth or slots therein.

Actuator 1706 can include handle 1728 and threaded shaft 1729, where threaded shaft 1729 can be a threaded elongate shaft configured to threadably interface with shaft bore 1725. Handle 1728 can be secured to a lateral end of threaded shaft 1729 and can be operable to rotate threaded shaft 1729.

Stem 1708 can include flange 1730 (including notch 1736), tapered portion 132, and key bit 1734, all of which can be consistent with tool 525 discussed above with respect to FIGS. 5A and 5B. Stem 1708 can be a portion of body 1702 or can be an independent component coupleable to body 1702 in other examples. Stem 1708 can also be coupleable to a surgical arm through an end effector coupler (such end effector coupler 500 above).

In assembly of some examples, movable body 1722 can be placed between medial upright 1714 and lateral upright 1712 so that shaft bore 1725 is substantially coaxial with lateral bore 1716 and medial bore 1720. Then, threaded shaft 1729 can be extended through lateral bore 1716, shaft bore 1725, and medial bore 1720 to couple movable body 1722 to medial upright 1714 and lateral upright 1712 so that handle 1728 extends laterally beyond lateral upright 1712. In some examples only shaft bore 1725 can be threaded so that threaded shaft 1729 is free to spin relative to medial upright 1714 and lateral upright 1712 and so that rotation of threaded shaft 1729 causes translation of movable support 1704. Further details of the operation of instrument holder 1700 are discussed below with respect to FIGS. 18A and 18B.

FIG. 18A illustrates a perspective view of instrument holder 1700 and flat instrument 1800, in accordance with at least one example of this disclosure. In some examples, instrument holder 1700 can be a flat instrument holder. The components of instrument holder 1700 can be consistent with those shown in FIGS. 17A-17C except that FIG. 18A shows unthreaded portion 1740 of threaded shaft 1729 that can be disposed in lateral bore 1725 of lateral upright 1712. FIG. 18A also shows grooves 1742 in handle 1728, which can provide grip or purchase of handle 1728 during rotation thereof.

FIG. 18A also shows flat instrument 1800, which can be a substantially flat and/or malleable retractor, such as a ribbon retractor, in some examples. Flat instrument 1800 can include medial side 1802 and lateral side 1804.

In operation of some examples, stem 1708 can be inserted into an end effector coupler, such as end effector coupler 500 discussed above, either before or after instrument holder 1700 is secured to an instrument. When it is desired to insert flat instrument 1800 into instrument holder 1700 handle 1728 can be rotated about axis A1 until a medial side of movable body 1704 contacts a lateral side of medial support 1714. During rotation of handle 1728 and therefore threaded shaft 1729, rotation of movable member 1704 is prevented by contact between movable body 1722 and base 1710 to force movable body 1722 to translate in response to rotation of handle 1728.

When movable body 1722 is at a desired position, either medial side 1802 or lateral side 1804 of flat instrument 1800 can be inserted into fixed jaw slot 1718 or pivotable jaw slot 1727, respectively. Then, handle 1728 can be rotated about axis A1 to translate movable body 1704 (and therefore pivotable jaw 1726) laterally toward lateral upright 1712. Translation can continue until the other of fixed jaw slot 1718 or pivotable jaw slot 1727 contacts medial side 1802 or lateral side 1804, respectively, to clamp flat instrument 1800 between lateral upright 1712 and pivotable jaw 1726.

In some examples, where flat instrument 1800 has a taper along a length of instrument 1800, handle 1728 can be rotated until pivotable jaw 1726 is in a desired location relative to fixed jaw slot 1718. Then, medial side 1802 and lateral side 1804 of instrument 1800 can be simultaneously slid into fixed jaw slot 1718 and pivotable jaw slot 1728, respectively. Instrument 1800 can be inserted, for example, proximally to distally, until instrument 1800 contacts both of fixed jaw slot 1718 and pivotable jaw slot 1728 such that flat instrument 1800 cannot be moved further distally. Handle 1728 can then be rotated to further clamp jaw slot 1718 and pivotable jaw slot 1728 on lateral side 1804 and medial side 1802, respectively, of flat instrument 1800 to retain a position of flat instrument 1800 relative to instrument holder 1700.

When it is desired to remove flat instrument 1800 from between lateral upright 1712 and pivotable jaw 1726, handle 1728 can be operated to translate movable body 1722 medially to separate pivotable jaw 1726 from upright 1712 so that flat instrument 1800 can be released, repositioned, and/or removed.

During operation or clamping of instrument 1800 between upright 1712 and pivotable jaw 1726 the V-shapes of fixed jaw slot 1718 and pivotable jaw slot 1727 can offer the benefit of accommodating flat instruments of various thickness. Further, teeth 1719 can improve retention of various sizes of flat instruments within fixed jaw slot 1718 and pivotable jaw slot 1727.

Also, because pivotable jaw 1726 can be pivotably coupled to movable body 1722 such that pivotable jaw 1726 can pivot about pin 1724, pivotable jaw 1726 can self-align on a flat instrument that is tapered (such as medial side 1802 of flat instrument 1800) to increase contact area between medial side 1802 and pivotable jaw 1726. Because pivotable jaw 1726 can pivot about pin 1724 to accommodate a tapered instrument, fixed jaw slot 1718 can also maintain contact with a large area of lateral side 1804.

FIG. 18B illustrates a perspective view of instrument holder 1700 and torque tool (or torque-assist tool) 1810, in accordance with at least one example of this disclosure. Instrument holder 1700 can be consistent with those shown in FIGS. 17A-17C and 18A discussed above. Torque tool 1810 can include radial extensions 1812 and 1814, which can be handles extending radially from a body of torque tool 1810 and can be configured to increase leverage or torque applied to torque tool 1810 and can accommodate various hand sizes. Torque tool 1810 can further include radial projections 1816 that can be sized and configured to engage grooves 1742 of handle 1728 to transfer torque between handle 1728 and torque tool 1810.

Figure 19:
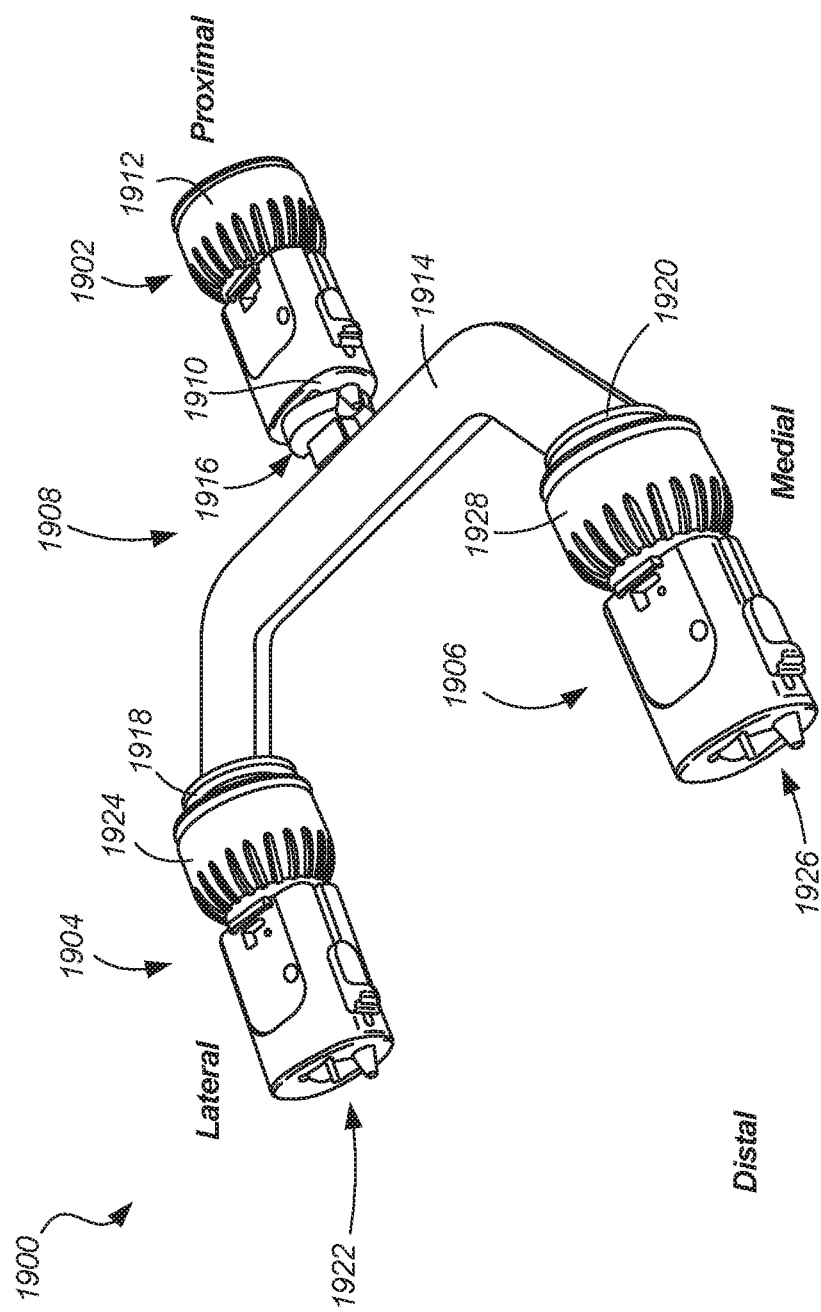
FIG. 19 illustrates a perspective view of an end effector coupler assembly, in accordance with at least one example of this disclosure.
Figure 20:
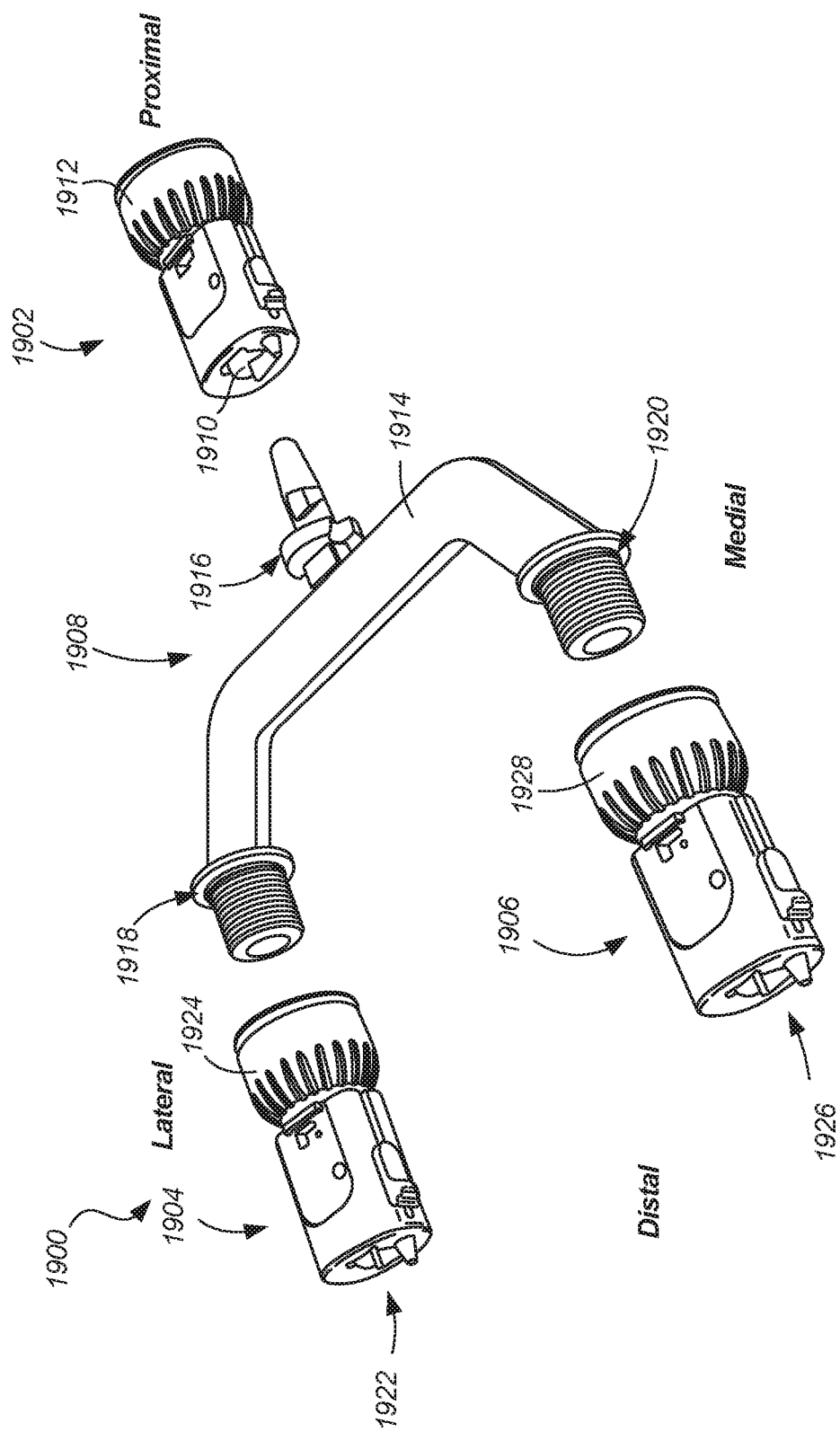
FIG. 20 illustrates a perspective view of an end effector coupler assembly, in accordance with at least one example of this disclosure.

FIG. 19 illustrates a perspective view of end effector coupler assembly 1900 in a connected condition, in accordance with at least one example of this disclosure. FIG. 20 illustrates a perspective view of end effector coupler assembly 1900 in a disconnected condition, in accordance with at least one example of this disclosure. FIGS. 19A and 19B are discussed below concurrently.

End effector coupler assembly 1900 can include proximal end effector coupler 1902, lateral end effector coupler 1904, medial end effector coupler 1906, and arm 1908. Proximal end effector coupler 1902 can include keyed opening 1910 and proximal coupler 1912. Arm 1908 can include proximal stem 1916 lateral threaded insert 1918 and medial threaded insert 1920. Medial end effector coupler 1904 can include keyed opening 1922 and proximal coupler 1924. Lateral end effector coupler 1906 can include keyed opening 1926 and proximal coupler 1928. Also shown in FIGS. 19A and 19B are orientation indicators Proximal, Distal, Medial, and Lateral.

Each of end effector couplers 1902, 1904, and 1906 can be similar to the end effector couplers discussed above, such as end effector coupler 500 of FIGS. 5A-6B. In this example, multiple end effector couplers can be used to expand the number of instruments that can be secured to a surgical arm using arm 1908, which can include a rigid body 1914 coupled to stem 1916 (which can be similar to the stems discussed above, such as stem 525 of FIG. 5B). Body 1914 can also be coupled to threaded insert 1918 which can be laterally spaced away from medial threaded insert 1920, which can also be coupled to body 1914. Body 914 can therefore be a bracket configured to secure and support multiple end effectors.

Threaded insert 1918 can be threadably coupled to lateral end effector coupler 1904 and medial threaded insert 1920 can be threadably coupled to medial end effector coupler 1906. In this way proximal end effector coupler 1902 can connect to a surgical arm to provide the ability to secure multiple tools to the surgical arm. For example, lateral end effector coupler 1904 can receive a tool stem of a tool in keyed opening 1922 and medial end effector coupler 1906 can receive a tool stem of another tool in keyed opening 1926.

Figure 21:
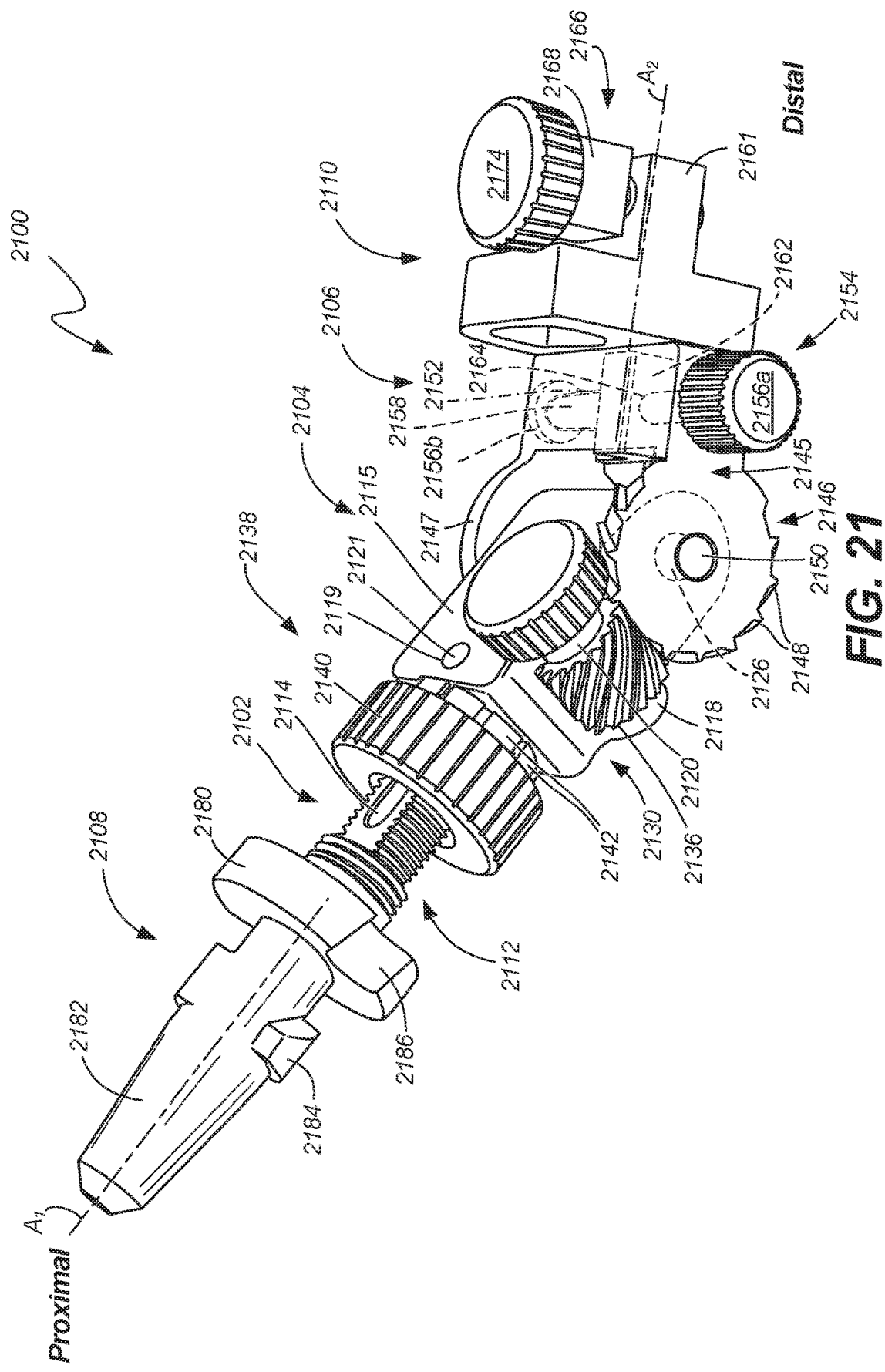
FIG. 21 illustrates a perspective view of an instrument holder, in accordance with at least one example of this disclosure.

FIG. 21 illustrates a perspective view of instrument holder 2100, in accordance with at least one example of this disclosure. Instrument holder 2100 can include body 2102, axial body 2104, rotating body 2106, stem 2108, and transverse body 2110. Also shown in FIG. 21 are orientation indicators Proximal and Distal and Axes A1 and A2.

Stem 2108 can be coupled to body 2102 and can extend proximally therefrom. Axial body 2104 can be threadably engaged with body 2102 in an adjustable manner, such that axial body 2104 can translate relative to body 2102. Rotating body 2106 can be coupled to a distal portion of axial body 2104 so that rotating body 2106 can be rotated relative to axial body 2104. Transverse body 2110 can be coupled to a distal portion of rotating body 2106 so that transverse body 2110 can be translated (transverse to body 2102) relative to rotating body 2104. Transverse body 2110 can also include a clamp sized and configured to releasably retain an instrument.

In operation of some examples, stem 2108 can be coupled to an end effector coupler (such as end effector coupler 500 discussed above with respect to FIGS. 5A and 5B) to secure instrument holder 2100 to a surgical arm. Either before or after stem 2108 is secured to the end effector coupler, an instrument can be secured to the clamp of transverse body 2110. A user can then adjust a position of the tool relative to stem 2108 by adjusting: a position of transverse body 2110 relative to rotating body 2106 in a translating manner transverse to body 2102; a position of rotating body 2106 relative to axial body 2104 via rotation of rotating body 2106; and/or, an axial position of axial body 2104 relative to body 2102.

In this way, instrument holder 2100 can provide relatively fine adjustments of a position of the instrument relative to stem 2108 and therefore the end effector coupler and surgical arm. Further details of instrument holder 2100 are discussed below with respect to both FIGS. 21 and 22.

Figure 22:
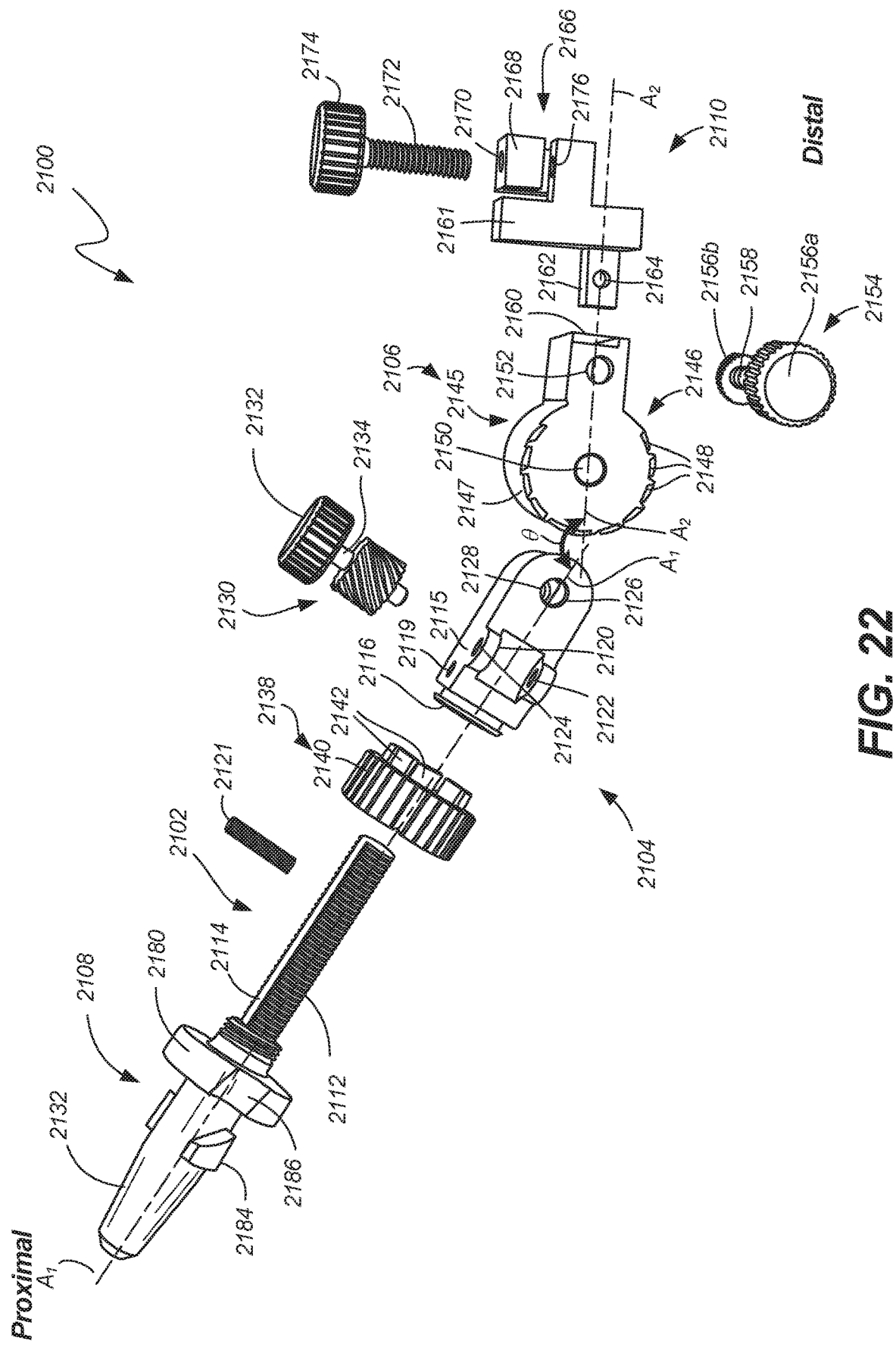
FIG. 22 illustrates an exploded perspective view of an instrument holder, in accordance with at least one example of this disclosure.

FIG. 22 illustrates an exploded perspective view of instrument holder 2100, in accordance with at least one example of this disclosure. Instrument holder 2100 can include body 2102, axial body 2104, rotating body 2106, stem 2108, and transverse body 2110. Body 2102 can include threaded portion 2112 and axial slot 2114. Axial body 2104 can include body 2115, proximal flange 2116, actuator flanges 2118 (including actuator bore 2122) and 2120 (including actuator bore 2124), pivot bores 2126 and 2128, axial driver 2130 (including knob 2132, shaft 2134, and worm drive 2136), and collar 2138, which can include knob 2140 and tabs 2142. Rotating body 2106 can include body 2145, driven gear 2146 (including teeth 2148), projections 2150 (only one visible in FIGS. 21 and 22), transverse bore 2152, transverse actuator 2154 (including knobs 2156a and 2156b and shaft 2158), and transverse slot 2160. Transverse body 2110 can include body 2161, projection 2162 (including projection bore 2164), clamp 2166 (including arm 2168, arm bore 2170, shaft 2172, and knob 2174), and body bore 2176. Stem 2108 can include flange 2180, taper 2182, projection 2184 (or key bit 2184), and notch 2186. Also shown in FIG. 21 are orientation indicators Proximal and Distal and Axes A1 and A2, and angle θ.

Instrument holder 2100 can be comprised of materials such as metals, plastics, foams, elastomers, ceramics, composites, and combinations thereof. In some examples, instrument holder 2100 can be comprised of rigid metals such as stainless-steel alloys and titanium for their strength properties and their ability to be cleaned (such as through an autoclave procedure), allowing instrument holder 2100 to be reusable.

Body 2102 can be a rigid body extending along axis A1. Body 2102 can include threaded portion 2112 extending along an outer portion of body 2102 and substantially an entire axial length of body 2102. Body 2102 can be of a substantially truncated cylindrical shape with two elongate flat portions, where axial slot 2114 extends along a length of body 2102 between the elongate flat portions. Axial slot can be sized to receive pin 2121 therein, where pin 2121 can be an elongate fastener, such as a pin, screw, rivet, and the like.

Axial body 2104 can include body 2115, which can be a rigid member and can include proximal flange 2116 extending from a proximal portion of body 2115. Proximal flange 2116 can have a geometric shape that is a substantially hollow cylinder including a lip at a proximal termination of proximal flange 2116. Actuator flanges 2118 and 2120 can extend from a medial or lateral side of body 2116 and can respectively include actuator bores 2122 and 2124, which can be sized to receive driver shaft 2134 therein. Pivot bores 2126 and 2128 can extend through a distal portion of body 2115 and can be coaxial, in some examples. Pivot bores 2126 and 2128 can be sized to receive projections 2150 therein to pivotably couple rotating body 2106 to axial body 2104.

Axial driver 2130 can be a driver coupleable to body 2115 and can be engageable with driven gear 2146 of rotating body 2106. Knob 2132 can be a handle or knob coupleable to shaft 2134. Knob 2132 can be ergonomically shaped for hand rotation and can be configured to deliver a torque to, or to rotate, shaft 2134 about an axis of shaft 2134. Worm drive 2136 can be a worm gear coaxial with and coupled to shaft 2134 in such a manner to that worm drive 2136 can rotate with shaft 2134 about a gear axis (AG) that is substantially transverse to, and offset from, axis A1. Worm drive 2136 can be other types of gears in other examples, such as a spur gear rotated about an axis transverse to driven gear 2146.

Collar 2138 can be a hand-operated collar threadably engageable with threaded portion 2118 of shaft 2102. Knob 2140 can be ergonomically shaped for hand rotation and can be configured to rotate about body 2102. Knob 2140 can be coupled to one or more tabs 2142 extending distally from knob 2140. As discussed further below, each of tabs 2142 can include radial projections configured to engage a distal lip of proximal flange 2116 of axial body 2104 to couple collar 2138 to axial body 2104 while still allowing relative rotation of collar 2138 to proximal flange 2116.

Rotating body 2106 can include body 2145 which can be a rigid member. Driven gear 2146 can be a disk or gear shaped protrusion extending proximally from a proximal portion of body 2145. Driven gear 2146 can include one or more teeth 2148 disposed around an outer edge or periphery of driven gear 2146 where teeth 2148 can be configured to interact with worm drive 2136 of driver 2130. Projections 2150 (only one visible in FIGS. 21 and 22) can extend inward (transverse to axis A1) from worm drive 2136 and support 2147 (which can oppose driven gear 2146). Each of projections 2150 can be sized and configured to be disposed in pivot bores 2126 of axial body 2104 to pivotably couple rotating body 2146 to axial body 2104.

Transverse bore 2152 can be a bore extending transverse to axis A1 proximate a distal portion of body 2145. Transverse bore 2152 can intersect with transverse slot 2160, which can extend proximally into body 2145 from a distal end of body 2145. Transverse actuator 2154 can be a hand-operated actuator where shaft 2158 is threadably engageable with projection 2162 of transverse body 2110. Knobs 2156a and 2156b can be coupled to opposite ends of shaft 2158 and can be ergonomically shaped for hand rotation and can be configured to drive shaft 2158 to rotate about an axis of shaft 2158.

Transverse body 2110 can include body 2161, which can be a rigid member including projection 2162 extending substantially proximally therefrom. In some examples, projection 2162 can have a geometric shape of a substantially square prism configured to be disposed in transverse slot 2160. In other examples, projection 2162 can be other shapes, such as other cuboids or prisms. Projection bore 2164 can extend transversely through projection 2162 and can include threading therein configured to threadably engage shaft 2158 of transverse actuator 2154. Clamp 2166 can be configured to receive and retain an instrument therein. Arm 2168 can be a cantilevered member extending from body 2161 such that arm 2168 can elastically deflect to close clamp 2166. Arm bore 2170 can extend through a portion of arm 2168 near a termination of arm 2168 and can be coaxial with body bore 2176 and sized to receive shaft 2172 therethrough.

Shaft 2172 and knob 2174 can together comprise a clamp actuator. Shaft 2172 can be a threaded shaft with knob 2174 secured to one end of shaft 2172. Knob 2174 can be ergonomically shaped for hand rotation and can be configured to drive shaft 2172 to rotate about an axis of shaft 2172 to draw arm 2168 closer to or further away from body 2161 to, respectively, close or open clamp 2166.

The components of stem 2108, including flange 2180, taper 2182, projection 2184 (or key bit 2184), and notch 2186, can be similar to those discussed above. For examples, stem 2108 can be similar to stem 525 of FIG. 5 such that stem 2180 can be coupleable to end effector coupler 500 to secure instrument holder 2100 thereto.

In operation of some examples, stem 2108 can be coupled to an end effector coupler (such as end effector coupler 500 discussed above with respect to FIGS. 5A and 5B) to secure instrument holder 2100 to a surgical arm. Either before or after stem 2108 is secured to the end effector coupler, an instrument can be secured to the clamp of transverse body 2110 and the position of the instrument can be adjusted as described in further detail below.

An instrument can be inserted into clamp 2166 and shaft 2172 can be rotated using knob 2174 to thread shaft 2172 through arm bore 2170 and body bore 2176 to deflect arm 2168 toward body 2161, making clamp 2166 smaller until clamp 2166 engages the instrument and retains the instrument therein. When clamp 2166 sufficiently holds the position of the instrument, a user can cease rotation of knob 2174 and can then adjust a position of clamp 2166 (and the instrument) relative to stem 2108 (and therefore a surgical arm). However, in some examples, a position of clamp 2166 can be adjusted prior to retaining the instrument within clamp 2166.

To adjust an axial position of clamp 2166 relative to stem 2108, knob 2140 of collar 2138 can be rotated about axis A1. The threaded engagement of collar 2138 with body 2102 can cause translation of collar 2138 along body 2102. Because tabs 2142 couple collar 2138 to proximal projection 2116, axial body 2104 translates with collar 2138. Also, because pin 2121 is secured to pin bore 2119 of body 2115 and because pin 2121 passes through axial slot 2114, body 2115 cannot rotate relative to body 2102 during translation. Also, contact between pin 2121 and proximal and distal ends of axial slot 2114 can limit translation of axial body 2106 relative to body 2102. When a desired translation of axial body 2104 is achieved relative to body 2102 and stem 2108, rotation of knob 2140 can be ceased.

Translation of axial body 2104 in the opposite direction can be achieved by rotating knob 2140 in the opposite direction. For example, clockwise rotation of knob 2140 from a proximal perspective can cause distal translation of axial body 2104 and counter-clockwise rotation of knob 2140 from a proximal perspective can cause proximal translation of axial body 2104.

When it is desired to adjust a rotational position (defined by angle θ between axes A1 and A2) of clamp 2166 relative to axial body 2104 (and body 2102, stem 2108, and a surgical arm), driver 2130 can be operated. During this process, a user can rotate knob 2132 about an axis of shaft 2134 to cause rotation of worm drive 2136. Because worm drive 2136 is engaged with teeth 2148 of driven gear 2146, rotation of worm drive 2136 causes rotation of driven gear 2146 about its axis (an axis of projection 2150, in some examples). This rotation of driven gear 2146 rotates body 2145 and all of rotating body 2106, transverse body 2110, and clamp 2166 relative to axial body 2104 (and body 2102, stem 2108, and a surgical arm).

Rotation of rotating body 2106 in the opposite direction can be achieved by rotating knob 2132 in the opposite direction. For example, clockwise rotation of knob 2140 from a top perspective (relative to FIG. 21) can cause angle θ to become smaller and rotation of knob 2140 from a top perspective (relative to FIG. 21) can cause angle θ to become larger. In some examples, rotating body 2106 can rotate through a range of angle θ of greater than 270 degrees.

When it is desired to adjust the position of clamp 2166 transversely to stem 2108 (and a surgical arm, axial body 2104, and rotating body 2106), knob 2156a and/or knob 2156b can be rotated to rotate shaft 2158. Because shaft 2158 can be in a threaded engagement with projection bore 2164, rotation of shaft 2158 can cause translation of projection 2162 transversely to axis A1 within transverse slot 2160 of rotating body 2106. Translation of projection 2162 can cause translation of body 2161 (and clamp 2166) relative to rotating body 2106. Translation of projection 2162 can be limited by contact between projection 2162 and ends of transverse slot 2160. Also, because transverse slot 2160 can have a shape that is complimentary to projection 2162, transverse slot can limit rotation of projection 2162 relative to slot 2160 by contacting projection 2162.

Translation of transverse body 2110 in the opposite direction can be achieved by rotating knob 2156a and/or knob 2156b in the opposite direction. For example, clockwise rotation of knob 2156a and/or knob 2156b from a lateral perspective can cause lateral translation of transverse body 2110 and counter-clockwise rotation of knob 2156a and/or knob 2156b from a lateral perspective can cause medial translation of transverse body 2110.

If it is desired to adjust a position of clamp 2166 or the instrument therein, the position of the instrument can be adjusted using clamp knob 2174, the position can be axially translated using collar 2138, the position can be rotated using driver 2130, and/or the position can be transversely translated using knob 2174. In this away, instrument holder 2100 can help provide a user an ability to make precise and accurate position adjustments while the instrument is secured to a surgical arm. In some examples, when a surgical arm is locked in place in a precise location, it may be difficult to adjust a position of the arm to a second precise location due to the mechanics of the joints of the surgical arm. Instrument holder 2100 provides a way to adjust a position of the instrument precisely without the need to move or reposition the surgical arm, helping to provide an ability to make micro-adjustments with a surgical arm.

Figures 23A, 23B:
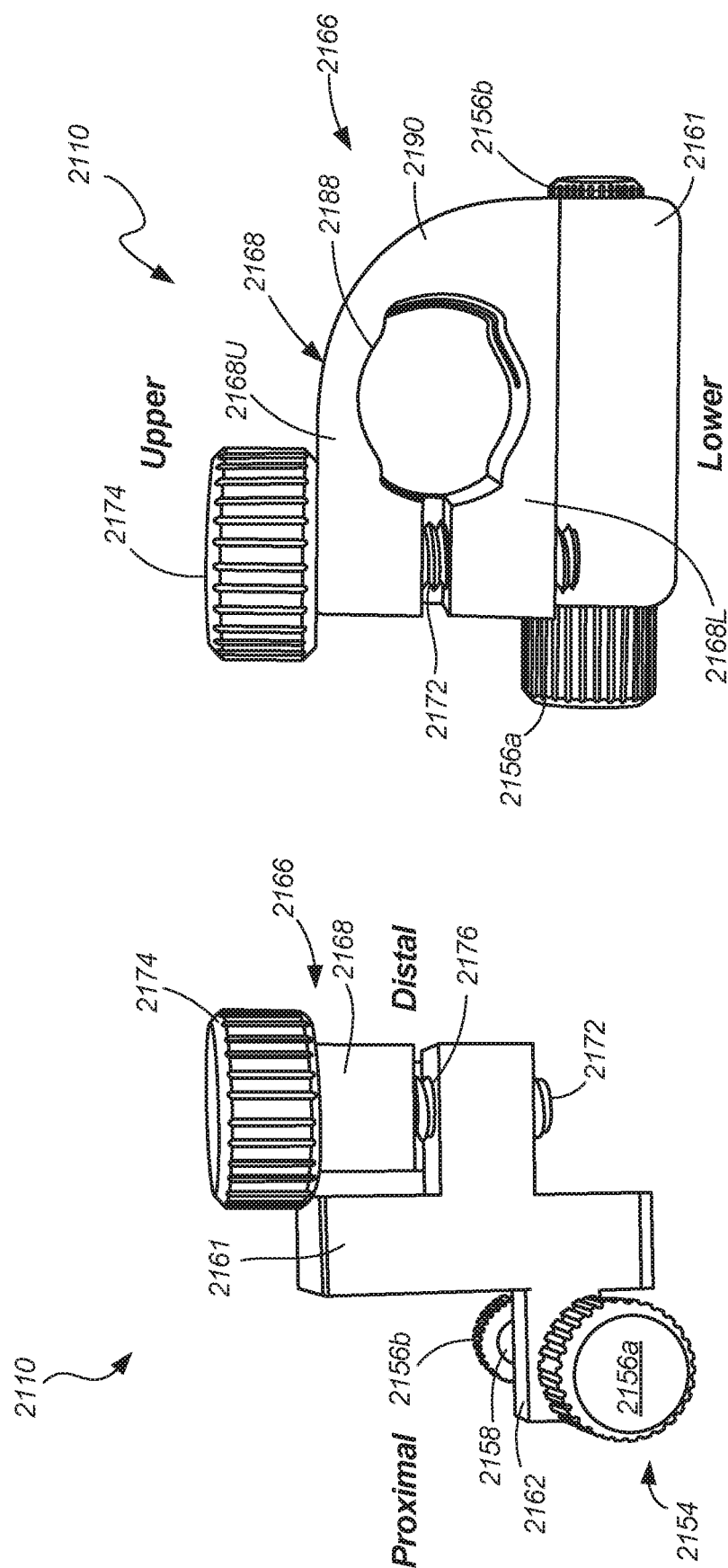
FIG. 23A illustrates a perspective view of a portion of an instrument holder, in accordance with at least one example of this disclosure.
FIG. 23B illustrates a perspective view of a portion of an instrument holder, in accordance with at least one example of this disclosure.

FIG. 23A illustrates a perspective view transverse body 2110 of instrument holder 2100, in accordance with at least one example of this disclosure. FIG. 23B illustrates a perspective view of transverse body 2110 of instrument holder 2100, in accordance with at least one example of this disclosure.

Transverse body 2110 can include body 2161, projection 2162, clamp 2166 (including arm 2168, arm bore 2170, shaft 2172, and knob 2174), and body bore 2176. Also shown in FIG. 23A are orientation indicators Proximal and distal. Also shown in FIG. 23B are orientation indicators Upper and Lower.

Transverse body 2110 of FIGS. 23A and 23B can be consistent with transverse body 2110 of FIGS. 21 and 22 described above, except that FIGS. 23A and 23B show additional details of transverse body. For example, FIG. 23B shows that arm 2168 can include upper portion 2168U and lower portion 2168L which can be connected at hinged 2190 and can together create clamp opening 2188 (or instrument opening 2188). Hinge 2190 can be an integral portion of arm 2168 (a living hinge) that allows for upper portion 2168U of arm 2168 to elastically deflect relative to lower portion 2168L of arm 2168 in response to a force applied by knob 2174 as shaft 2172 is threaded into arm bore 2170 and body bore 2176.

FIG. 23B also shows that clamp opening 2188 can have an irregular geometric shape comprised of multiple arcs. In other examples, clamp opening 2188 can have other geometric shapes.

Though transverse actuator 2154 is described with respect to FIGS. 21 and 22 as being a component of rotating body 2106, transverse actuator 2154 can be a portion of transverse body 2110 (as shown in FIGS. 23A and 23B) or can be a separate component of instrument holder 2110.

FIG. 24A illustrates a perspective view of rotating body 2106 of instrument holder 2100, in accordance with at least one example of this disclosure. FIG. 24B illustrates a perspective view of rotating body 2106 of instrument holder 2100, in accordance with at least one example of this disclosure. FIGS. 24A and 24B are discussed below concurrently.

Rotating body 2106 can include body 2145, driven gear 2146 (including teeth 2148), support 2147, projections 2150a and 250b, transverse bore 2152, and transverse slot 2160. Also shown in FIG. 24A are orientation indicators Proximal and Distal.

Rotating body 2106 of FIGS. 24A and 24B can be consistent with rotating body 2106 of FIGS. 21 and 22 discussed above, except FIGS. 24A and 24B show additional details of rotating body 2106. For example, FIGS. 24A and 24B show transverse bores 2152a and 2152b extending through body 2145 coaxially. FIGS. 24A and 24B also show transverse slot extending transversely along a distal portion of body 2145 and into body 2145 from a distal end of body 2145. Also shown are projections 2150a and 2150b extending inward from driven gear 2146 and support 2147, respectively.

FIG. 25A illustrates a perspective view of body 2102 and stem 2108 of instrument holder 2110, in accordance with at least one example of this disclosure.

Body 2102 can include threaded portion 2112 and axial slot 2114. Stem 2108 can include flange 2180, taper 2182, projection 2184 (or key bit 2184), and notch 2186. Also shown in FIG. 25A are orientation indicators Proximal and Distal.

Body 2102 and stem 2108 of FIG. 25A can be consistent with body 2102 and stem 2108 of FIGS. 21 and 22 discussed above. However, FIG. 25A shows additional details of body 2102 such as proximal and distal terminations of axial slot 2114. FIG. 25A also shows a distal termination of body 2102 and shows how pin 2121 can be disposed within axial slot 2114.

FIG. 25B illustrates a perspective view of collar 2138 of instrument holder 2110, in accordance with at least one example of this disclosure. Collar 2138 can include knob 2140 and tabs 2142.

Collar 2138 of FIG. 25B can be consistent with collar 2138 of FIGS. 21 and 22 discussed above. However, FIG. 25B shows additional details of collar 2138 such as tab projections 2143, which can be projections or protuberances extending radially inward from each of tabs 2142. In some examples, each of tab projections 2143 can include a hook or lip configured to interface with proximal flange 2116 of axial body 2104 to secure collar 2138 thereto. FIG. 25B also shows how each of tabs 2142 cantilever from knob 2140. This can allow tabs 2142 to individually deflect relative to knob 2140. This allows tabs 2142 to couple to proximal flange 2116 of axial body by applying a force to collar 2138 so that tabs 2142 deflect outward during engagement and then back inward to engage and retain proximal flange 2116.

FIG. 25B also shows female threaded portion 2141, which can be sized and configured to received body 2142 therethrough and can be sized and configured to thread ably interact with threaded portion 2112 of body 2102.

Figure 26B:
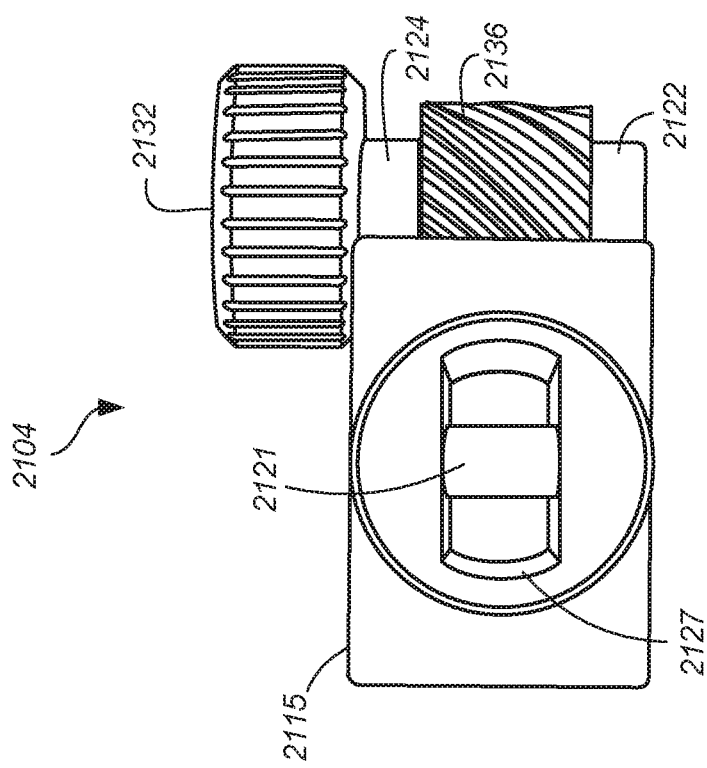
FIG. 26B illustrates a perspective view of a portion of an instrument holder, in accordance with at least one example of this disclosure.
Figure 26A:
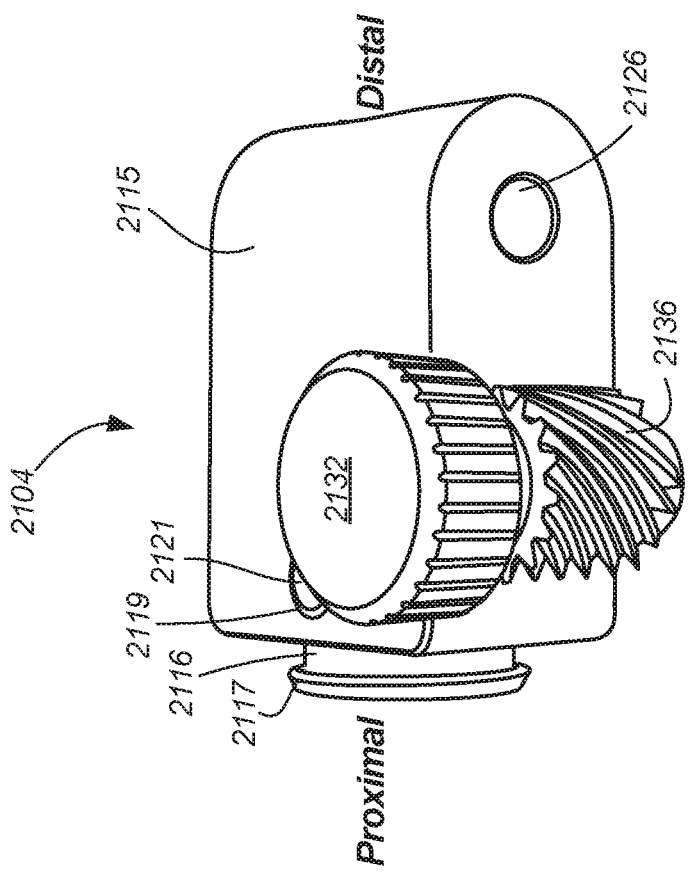
FIG. 26A illustrates a perspective view of a portion of an instrument holder, in accordance with at least one example of this disclosure.

FIG. 26A illustrates a perspective view of a portion of axial body 2104 of instrument holder 2110, in accordance with at least one example of this disclosure. FIG. 26B illustrates a perspective view of axial body 2104 of instrument holder 2110, in accordance with at least one example of this disclosure.

Axial body 2104 can include body 2115, proximal flange 2116, actuator flanges 2118 and 2120, pivot bore 2126, body bore 2127, axial driver 2130 (including knob 2132 and worm drive 2136). Also shown in FIG. 26A are orientation indicators Proximal and Distal.

Axial body 2104 of FIGS. 26A and 26B can be consistent with axial body 2104 of FIGS. 21 and 22 discussed above. However, FIGS. 26A and 26B show additional details of axial body 2104. For example, FIG. 26A shows lip 2117 of proximal flange 2116, which can be sized and configured to receive and retain projections 2143 of tabs 2142 to couple collar 2138 (and therefore body 2102) to axial body 2104.

FIG. 26B also show body bore 2127, which can be sized and shaped complimentary to body 2102 to receive body 2102 therein. FIG. 26B also shows how pin 2121 can extend into pin bore 2119 and can intersect body bore 2127 where pin 2120 can engage axial slot 2114 of body 2102 within body 2115 of axial body 2104.

FIG. 27A illustrates a perspective view of a portion of instrument holder 2700, in accordance with at least one example of this disclosure. FIG. 27B illustrates a perspective view of a portion of instrument holder 2700, in accordance with at least one example of this disclosure. FIG. 27C illustrates a perspective view of a portion of instrument holder 2700, in accordance with at least one example of this disclosure. FIGS. 27A-27C are discussed below concurrently.

Instrument holder 2700 can be consistent with instrument holder 2100 discussed above with respect to FIGS. 21-26B, except that instrument holder can include lock 2790A (FIG. 27A), lock 2790B (FIG. 27B), and lock 2790C (FIG. 27C).

Lock 2790A can include knob 2792A, shaft 2794A, and bore 2796A. Bore 2796A can be a threaded bore extending into body 2715 of axial body 2704 and can intersect with body bore 2727. Shaft 2794A can be a threaded shaft threadably engageable with bore 2796A and configured to engage body 2702 within axial body 2704. Knob 2792A can be a handle or knob coupled to an end of shaft 2794A and can be rotatable to cause rotation of shaft 2794A about an axis of shaft 2794A.

When it is desired to lock a position of body 2702 relative to axial body 2704, knob 2792A can be rotated to drive shaft 2764A into bore 2796A so that shaft 2794A engages body 2702 such that body 2702 is no longer free to translate relative to axial body 2704. This can provide a user an ability to fix an axial position of an instrument relative to a stem (such as stem 2108 of FIG. 21) and a surgical arm.

Lock 2790B can include knob 2792B, shaft 2794B, and bore 2796B. Bore 2796B can be a threaded bore extending into driven gear 2146 (or body 2145 in other examples) of rotating body 2706. Bore 2796B can align with body 2715 of axial body 2704. Shaft 2794B can be a threaded shaft threadably engageable with bore 2796B and configured to engage body 2715 of axial body 2704. Knob 2792B can be a handle or knob coupled to an end of shaft 2794B and can be rotatable to cause rotation of shaft 2794B about an axis of shaft 2794B.

When it is desired to lock a position of axial body 2704 relative to rotating body 2706, knob 2792B can be rotated to drive shaft 2764B into bore 2796B so that shaft 2794B engages body 2715 such that rotating body 2706 is no longer free to rotate relative to axial body 2704. This can provide a user an ability to fix a rotational position of an instrument relative to a stem (such as stem 2108 of FIG. 21) and a surgical arm.

Lock 2790C can include knob 2792C, shaft 2794C, and bore 2796C. Bore 2796C can be a threaded bore extending into body 2761 of transverse body 2710 and can align with a distal portion of rotating body 2106. Shaft 2794C can be a threaded shaft threadably engageable with bore 2796C and configured to engage body 2745 of rotating body 2706. Knob 2792C can be a handle or knob coupled to an end of shaft 2794C and can be rotatable to cause rotation of shaft 2794C about an axis of shaft 2794C.

When it is desired to lock a position of transverse body 2710 relative to rotating body 2706, knob 2792C can be rotated to drive shaft 2764C into bore 2796C so that shaft 2794C engages body 2745 such that translating body 2710 is no longer free to translate relative to rotating body 2706 This can provide a user an ability to fix a transverse position of an instrument relative to a stem (such as stem 2108 of FIG. 21) and a surgical arm.

EXAMPLES

The following, non-limiting examples, detail certain aspects of the present subject matter to solve the challenges and provide the benefits discussed herein, among others.

Example 1 is an end effector coupler system for an electromechanical surgical arm, the end effector coupler system comprising: an end effector body comprising a proximal portion and an opposite distal portion, the distal portion including a distal end; a control device coupleable to an external surface of the end effector body and operable to transmit a signal to allow movement of the surgical arm; a coupler connected to the proximal portion and releasably coupleable to the surgical arm, the coupler including a circumferential groove on an outer face of the coupler; a tool lock for releasably retaining a tool stem to the end effector coupler, the tool lock comprising: a keyed opening extending through the distal end into the distal portion, the keyed opening configured to receive the tool stem therein; a pin bore extending through the distal end proximate to the keyed opening; a pin disposed in the pin bore and extendable from the pin bore to engage and retain the tool stem when the tool stem is inserted into the keyed opening; and a biasing element located in the pin bore and engaging the pin to bias the pin to extend from the distal end; and a pin release comprising an actuator extending beyond an external surface of the end effector body and engaging the pin, the pin release operable to retract the pin into to the end effector body to disengage the pin from the tool stem allowing release of the tool stem from the keyed opening.

In Example 2, the subject matter of Example 1 optionally includes wherein the pin limits rotation of the stem relative to the keyed opening to prevent release of the stem from the keyed opening when the pin engages the stem.

In Example 3, the subject matter of any one or more of Examples 1-2 optionally include wherein the end effector body includes a flat outer surface configured to receive the control device thereon and a tab channel extending through the flat outer surface.

In Example 4, the subject matter of Example 3 optionally includes wherein the control device includes a tab extending from the control device, a portion of the tab insertable into the tab channel to releasably secure the control device to the end effector body.

In Example 5, the subject matter of Example 4 optionally includes wherein the end effector body includes a catch extending from the flat outer surface, the catch configured to receive a portion of the tab thereon to releasably secure the control device to the end effector body.

In Example 6, the subject matter of any one or more of Examples 1-5 optionally include wherein the control device includes a light indicator configured to indicate a condition of the end effector coupler.

In Example 7, the subject matter of any one or more of Examples 1-6 optionally include wherein the keyed opening further comprises a keyway extending radially from a central bore of the keyed opening and sized to receive a key bit of the stem therethrough, the key bit including an angled face engageable with a proximal portion of the keyway to limit axial movement of the stem relative to the keyed opening, and wherein the tapered bore is configured to receive a complimentary tapered section of the tool stem to form a taper-to-taper interface to limit relative motion between the end effector coupler and the tool stem, wherein a distal portion of the pin is configured to engage a notch of the tool stem to limit rotation of the tool stem relative to the end effector coupler, and wherein the angled face is configured to engage the proximal portion of the keyway substantially simultaneously with the tapered bore in receipt of the complimentary tapered section of the tool stem and substantially simultaneously with the distal portion of the pin in engagement with a notch of the tool stem.

In Example 8, the subject matter of any one or more of Examples 1-7 optionally include a tool including the tool stem, the tool configured to retain an instrument therein, and the tool releasably coupleable to the end effector coupler.

In Example 9, the subject matter of Example 8 optionally includes wherein the tool further comprises: a shaft including a coupling bore proximate a distal end of the shaft, the coupling bore transverse to a longitudinal axis of the shaft and configured to receive an instrument, and the stem extending proximally from the shaft; a clamping sleeve disposed on the shaft and axially translatable along the longitudinal axis of; and a collar disposed on the shaft and threadably engaged with the shaft to control axial translation of the collar on the shaft, the collar engageable with the clamping sleeve to translate the clamping sleeve with the collar, wherein axial translation of the clamping sleeve controls engagement of a distal edge of the clamping sleeve with the instrument to lock the instrument in position within the coupling bore.

In Example 10, the subject matter of Example 9 optionally includes a biasing element engaging the collar and the sleeve to bias the sleeve away from the collar.

In Example 11, the subject matter of any one or more of Examples 8-10 optionally include wherein the tool further comprises: a body including a proximal end and a distal end and a longitudinal axis extending therethrough, the stem coupled to the body and extending therefrom; a first platform fixedly coupled to the body; a second platform coupled to the body, the second platform opposing the first platform, and the second platform translatable relative to the body and the first platform, wherein the first platform and the second platform include opposing structure to retain the standard surgical instrument upon translation of the second platform toward the first platform; and an actuator engaging the second platform and the body, the actuator operable to translate the second platform relative to the body along the longitudinal axis.

In Example 12, the subject matter of any one or more of Examples 10-11 optionally include wherein first platform includes a v-groove extending transversely to the longitudinal axis, the v-groove at least partially shaped to conform to a straight portion of the surgical instrument, and wherein the second platform includes a first protrusion extending from the second platform toward the v-groove, the first protrusion insertable into the v-groove to retain the straight portion of the surgical instrument between the first platform and the straight portion.

In Example 13, the subject matter of any one or more of Examples 8-12 optionally include wherein the tool further comprises: a body, the stem coupled thereto, the body comprising: proximal portion; a distal portion opposite the proximal portion; and a retaining bore extending along a longitudinal axis of the body; a jaw forming a portion of two sides of the retaining bore opposite the proximal portion of the body in a first retracted state, the jaw translatable relative to the body into a second extended state where the jaw reduces the size of the retaining bore; and an actuator engageable with the distal portion and operable to translate the jaw relative to the proximal portion to adjust a size of the retaining bore.

In Example 14, the subject matter of Example 13 optionally includes wherein the jaw includes a geometric shape substantially of a H in a parallel plane that is parallel to the longitudinal axis of the body, and wherein the jaw includes a geometric shape substantially of a V in a transverse plane that is transverse to the longitudinal axis of the body.

In Example 15, the subject matter of any one or more of Examples 8-14 optionally include wherein the tool further comprises: a body including a proximal portion and a distal portion and comprising a substantially cylindrical geometric shape, the body extending along a longitudinal axis; a first platform fixedly coupled to the proximal portion of the body and extending radially from the body, the stem coupleable to the body proximal of the first platform and extending radially from the proximal portion of the body; a second platform coupled to the body proximate the first platform, the second platform extending radially from the body, the second platform opposing the first platform, and the second platform translatable relative to the body and the first platform; and an actuator securable to the distal portion of the body and engageable with the second platform, the actuator operable to translate the second platform relative to the body along the longitudinal axis.

In Example 16, the subject matter of Example 15 optionally includes wherein the body further includes an axial slot extending between the proximal portion of the body and the distal portion of the body, the retainer further comprising a retaining pin disposable in the axial slot and engageable with a bore of the second platform to limit translation of the platform relative to the body and to limit translation of the second platform relative to the body.

In Example 17, the subject matter of any one or more of Examples 8-16 optionally include wherein the tool further comprises: a body substantially forming a u-shape, the stem coupled to the body and extending therefrom, the body comprising: a base extending substantially longitudinally and including a medial portion and a lateral portion; a lateral upright extending substantially transversely from the lateral medial portion of the base, the lateral upright including a lateral bore and a fixed jaw slot extending substantially transversely to the lateral bore; and a medial upright extending substantially transversely from the lateral portion of the base opposite the lateral upright, the medial upright including a medial bore; an actuator comprising: a shaft coupleable to the lateral bore and the medial bore and extending there between; and a handle coupled to the shaft and extending laterally away from the lateral upright; a movable support opposing the lateral support, the movable support coupleable to the shaft and translatable along the shaft; wherein the actuator is operable to translate the movable support relative to the lateral support along the longitudinal axis to retain a surginical instrument between the movable support and the lateral support.

In Example 18, the subject matter of Example 17 optionally includes wherein the movable support further comprises: a movable body including a shaft bore extending through the body and a pivot bore substantially transverse to the shaft bore; and a pivotable jaw opposing the lateral upright and including a pivot projection disposable in the pivot bore and a pivotable jaw slot extending substantially transversely to the shaft bore, the pivotable jaw configured to pivot about the pivot bore.

In Example 19, the subject matter of any one or more of Examples 8-18 optionally include wherein the tool further comprises: a body extending along a longitudinal axis, the body comprising: a threaded member extending along the longitudinal axis, the stem coupled to the threaded member and extending therefrom; an axial body extending substantially along the longitudinal axis, the axial body comprising: a collar coupled to a proximal portion of the axial body, the collar threadably engageable with the threaded member of the body, and the collar operable to translate the axial body along the threaded member to adjust an axial position of the axial body relative to the body and the stem; and a driver secureable to the axial body and rotatable about a gear axis substantially transverse to, and offset from, the longitudinal axis, a rotating body rotatable relative to the axial body, the rotating body comprising: a transverse bore extending through a distal portion of the rotating body; a transverse slot intersecting the transverse bore; and a driven gear coupleable to the axial body and rotatable relative thereto, the driven gear engageable with the driver such that the driver is operable to rotate driven gear to rotate the rotating body a relative to the axial body and the stem; and a transverse body translatable transverse to the rotating body; the transverse body comprising: a clamp secured to the transverse body and extending therefrom, the clamp including an instrument opening and a clamp actuator, the clamp actuator operable to open and close the instrument opening; a projection extending from the transverse body and insertable into the transverse slot; and a transverse actuator disposable in the transverse bore of the rotating body and engageable with the projection, the transverse actuator operable to translate the projection within the transverse slot to translate the transverse body and the clamp relative to the rotating body, the axial body, and the stem.

In Example 20, the subject matter of Example 19 optionally includes wherein the driver includes a worm drive engageable with the driven gear and a handle coupled to the worm drive and operable to rotate the worm drive, and wherein the driven gear includes a worm gear driven by the worm drive.

Example 21 is an instrument holder receivable in an end effector coupler of a surgical arm, the instrument holder comprising: a shaft including a coupling bore proximate a distal end of the shaft, the coupling bore transverse to a longitudinal axis of the shaft and configured to receive an instrument; a stem extending proximally from the shaft; a clamping sleeve disposed on the shaft and axially translatable along the longitudinal axis of; and a collar disposed on the shaft and threadably engaged with the shaft to control axial translation of the collar on the shaft, the collar engageable with the clamping sleeve to translate the clamping sleeve with the collar, wherein axial translation of the clamping sleeve controls engagement of a distal edge of the clamping sleeve with the instrument to lock the instrument in position within the coupling bore.

In Example 22, the subject matter of Example 21 optionally includes the shaft further comprising: an axial slot extending along a portion of the shaft and terminating proximally of a distal end of the shaft; and a retaining pin disposable in the axial slot and engageable with a bore of the sleeve to limit translation of the sleeve and the collar relative to the shaft.

In Example 23, the subject matter of Example 22 optionally includes the shaft further comprising: a second axial slot terminating proximally of the distal end of the shaft; and a second retaining pin disposable in the second axial slot and engageable with a second bore of the sleeve to limit translation of the sleeve and the collar relative to the shaft; wherein the retaining pin and the second retaining pin do not intersect the coupling bore through throughout a full range of translation of the retaining pin in the axial slot and the second retaining pin in the second axial slot.

In Example 24, the subject matter of any one or more of Examples 22-23 optionally include wherein the sleeve includes: a notch extending axially inward from a distal termination of the shaft, the notch substantially having a geometric shape of a V, wherein the notch is alignable with the coupling bore when the retaining pin extends through the slot of the shaft and the bore of the sleeve.

In Example 25, the subject matter of any one or more of Examples 21-24 optionally include a biasing element engaging the collar and the sleeve to bias the sleeve away from the collar.

In Example 26, the subject matter of any one or more of Examples 21-25 optionally include wherein the shaft includes a male threaded portion and the collar includes a female threaded portion threadably engageable with the male threaded portion to translate the collar and the sleeve relative to the shaft in response to rotation of the collar about the longitudinal axis of the shaft.

In Example 27, the subject matter of any one or more of Examples 21-26 optionally include wherein: the collar further comprises: a collar sleeve surrounding the shaft; and a radial projection coupled to a distal portion of the collar sleeve, the radial projection extending at least partly circumferentially around the collar; and the sleeve is disposable around the collar sleeve and engageable with the radial projection.

In Example 28, the subject matter of any one or more of Examples 21-27 optionally include the stem further comprising: a key bit extending radially from the stem including an angled face on a distal side of the key bit; and a flange extending radially outward from the stem and axially positioned to limit translation of the stem into the surgical arm.

Example 29 is an instrument coupler to couple a standard surgical instrument to an end effector of a positionable surgical arm, the instrument coupler comprising: a body including a proximal end and a distal end and a longitudinal axis extending therethrough; a stem coupled to the body and extending therefrom; a first platform fixedly coupled to the body; a second platform coupled to the body, the second platform opposing the first platform, and the second platform translatable relative to the body and the first platform, wherein the first platform and the second platform include opposing structure to retain the standard surgical instrument upon translation of the second platform toward the first platform; and an actuator engaging the second platform and the body, the actuator operable to translate the second platform relative to the body along the longitudinal axis.

In Example 30, the subject matter of Example 29 optionally includes a stabilizer coupled to one of the first platform and the second platform and extending radially outward therefrom.

In Example 31, the subject matter of Example 30 optionally includes wherein a position of the stabilizer is adjustable relative to the one of the first platform and the second platform that is connected to the handle.

In Example 32, the subject matter of any one or more of Examples 29-31 optionally include wherein first platform includes a v-groove extending transversely to the longitudinal axis, the v-groove at least partially shaped to conform to a straight portion of the surgical instrument, and wherein the second platform includes a first protrusion extending from the second platform toward the v-groove, the first protrusion insertable into the v-groove to retain the straight portion of the surgical instrument between the first platform and the straight portion.

In Example 33, the subject matter of Example 32 optionally includes wherein first platform includes a second v-groove extending transversely to the longitudinal axis, the v-groove at least partially shaped to conform to a curved portion of the surgical instrument, and wherein the second platform includes a second protrusion extending from the second platform toward the second v-groove, the second protrusion insertable into the second v-groove to retain the curved portion of the surgical instrument between the first platform and the curved portion.

In Example 34, the subject matter of Example 33 optionally includes wherein the groove is substantially straight relative to a chord of the body and wherein the second groove is substantially curved relative to the chord of the body.

In Example 35, the subject matter of Example 34 optionally includes wherein the first projection includes a substantially v-shaped profile complimentary to the groove and wherein the second projection has a substantially v-shaped and curved profile complimentary to the second groove.

In Example 36, the subject matter of any one or more of Examples 29-35 optionally include wherein the stem includes a stem platform releasably securable to the body.

In Example 37, the subject matter of Example 36 optionally includes a biasing element disposable between the stem platform and the body and engageable with the stem platform and the body to bias the stem platform away from the body.

In Example 38, the subject matter of any one or more of Examples 36-37 optionally include wherein the body includes a stem bolt extending from the body, the stem platform disposable around the stem bolt to position the stem platform relative to the body.

In Example 39, the subject matter of any one or more of Examples 37-38 optionally include a retainer threadably securable to the stem bolt to engage the stem platform and secure the stem platform relative to the body.

In Example 40, the subject matter of any one or more of Examples 36-39 optionally include wherein: the body further comprises a plurality of body teeth; and the stem platform further comprises a plurality of stem teeth engageable with the body teeth to limit rotation of the stem relative to the body.

In Example 41, the subject matter of any one or more of Examples 29-40 optionally include the stem further comprising: a key bit extending radially from the stem including an angled face on a distal side of the key bit; and a flange extending radially outward from the stem proximate the key bit.

Example 42 is a retainer for a surgical instrument, the retainer comprising: a body comprising: proximal portion; a distal portion opposite the proximal portion; and a retaining bore extending along a longitudinal axis of the body; stem coupled to the body; a jaw forming a portion of two sides of the retaining bore opposite the proximal portion of the body in a first retracted state, the jaw translatable relative to the body into a second extended state where the jaw reduces the size of the retaining bore; and an actuator engageable with the distal portion and operable to translate the jaw relative to the proximal portion to adjust a size of the retaining bore.

In Example 43, the subject matter of Example 42 optionally includes wherein: the body further comprises an actuator bore substantially transverse to the retaining bore; and the actuator further comprises a shank engageable with the actuator bore to enable translation of the jaw relative to the body in response to operation of the actuator.

In Example 44, the subject matter of any one or more of Examples 42-43 optionally include wherein the jaw includes a geometric shape substantially of a H in a parallel plane that is parallel to the longitudinal axis of the body.

In Example 45, the subject matter of Example 44 optionally includes wherein the jaw includes a geometric shape substantially of a V in a transverse plane that is transverse to the longitudinal axis of the body.

In Example 46, the subject matter of Example 45 optionally includes the jaw further comprising: a jaw body coupleable to the actuator and engageable with the distal portion to limit translation of the jaw relative to the body; a first arm extending from the jaw body transversely to the longitudinal axis and shaped complementary to the distal portion of the body, the first arm located axially outward from the body; and a second arm extending from the jaw body transversely to the longitudinal with the first arm and shaped complementary to the distal portion of the body, the second arm located axially outward from the body opposite the first arm.

In Example 47, the subject matter of any one or more of Examples 42-46 optionally include wherein the first arm and second arm are substantially parallel and each extend from the jaw body transversely to the longitudinal axis in two separate directions.

In Example 48, the subject matter of any one or more of Examples 42-47 optionally include wherein the proximal portion further comprises: a radially inner face that includes serrations facing the jaw.

In Example 49, the subject matter of any one or more of Examples 42-48 optionally include the stem further comprising: a key bit extending radially from the stem and including an angled face on a distal side of the key bit; and a flange extending radially outward from the stem proximate the key bit.

In Example 50, the subject matter of any one or more of Examples 42-49 optionally include wherein the actuator further comprises a fastener bore coaxial with the actuator bore, and wherein the actuator further comprises a fastener securable to the jaw and to the fastener bore to limit translation of the jaw relative to the actuator.

In Example 51, the subject matter of Example 50 optionally includes wherein the body further comprises an assembly bore extending through the proximal portion of the body coaxial with the fastener bore, the assembly bore sized to received the fastener therethrough.

Example 52 is a retainer for a surgical instrument, the retainer comprising: a body including a proximal portion and a distal portion and comprising a substantially cylindrical geometric shape, the body extending along a longitudinal axis; a first platform fixedly coupled to the proximal portion of the body and extending radially from the body; a stem coupleable to the body proximal of the first platform and extending radially from the proximal portion of the body; a second platform coupled to the body proximate the first platform, the second platform extending radially from the body, the second platform opposing the first platform, and the second platform translatable relative to the body and the first platform; and an actuator securable to the distal portion of the body and engageable with the second platform, the actuator operable to translate the second platform relative to the body along the longitudinal axis.

In Example 53, the subject matter of Example 52 optionally includes wherein the body further includes an axial slot extending between the proximal portion of the body and the distal portion of the body, the retainer further comprising a retaining pin disposable in the axial slot and engageable with a bore of the second platform to limit translation of the platform relative to the body and to limit translation of the second platform relative to the body.

In Example 54, the subject matter of Example 53 optionally includes wherein each of the first platform and the second platform comprises a first notch, the first notches together forming a first retaining bore including a first size adjustable based on a position of the second platform relative to the first platform, and wherein each of the first platform and the second platform comprises a second notch spaced from the first notch, the second notches together forming a second retaining bore including a second size adjustable based on the position of the second platform relative to the first platform.

In Example 55, the subject matter of any one or more of Examples 52-54 optionally include wherein the first retaining bore and second retaining bore are of different geometric sizes.

In Example 56, the subject matter of any one or more of Examples 52-55 optionally include wherein each of the first and second notches include teeth configured to limit rotation of an instrument disposed within respective first and second notches.

In Example 57, the subject matter of any one or more of Examples 52-56 optionally include wherein the distal portion of the body includes a threaded body portion, and wherein the actuator is threadably securable to the threaded body portion to translate the second platform relative to the body along the longitudinal axis.

In Example 58, the subject matter of any one or more of Examples 52-57 optionally include wherein the stem includes a stem platform releasably securable to the body.

In Example 59, the subject matter of Example 58 optionally includes wherein the body includes a stem bolt extending axially from the proximal portion of the body, the stem platform threadably securable to the stem bolt.

In Example 60, the subject matter of Example 59 optionally includes a biasing element disposable between the stem platform and the first platform and engageable with the stem platform and the first platform to bias the stem platform away from the first platform.

In Example 61, the subject matter of any one or more of Examples 59-60 optionally include a retainer threadably securable to the stem bolt to engage the stem platform and secure the stem platform relative to the body.

In Example 62, the subject matter of any one or more of Examples 58-61 optionally include wherein the first platform includes a plurality of body teeth, and wherein the stem platform includes a plurality of stem teeth engageable with the first platform teeth to limit rotation of the stem relative to the body.

In Example 63, the subject matter of any one or more of Examples 52-62 optionally include wherein the stem includes a key bit extending radially from the stem and including an angled face on a distal side of the key bit, and a flange extending radially outward from the stem proximate the key bit.

Example 64 is a retainer for a surgical instrument, the retainer comprising: a body substantially forming a u-shape, the body comprising: a base extending substantially longitudinally and including a medial portion and a lateral portion; a lateral upright extending substantially transversely from the lateral medial portion of the base, the lateral upright including a lateral bore and a fixed jaw slot extending substantially transversely to the lateral bore; and a medial upright extending substantially transversely from the lateral portion of the base opposite the lateral upright, the medial upright including a medial bore; a stem coupled to the body and extending therefrom; an actuator comprising: a shaft coupleable to the lateral bore and the medial bore and extending there between; and a handle coupled to the shaft and extending laterally away from the lateral upright; a movable support opposing the lateral support, the movable support coupleable to the shaft and translatable along the shaft; wherein the actuator is operable to translate the movable support relative to the lateral support along the longitudinal axis to retain a surgincal instrument between the movable support and the lateral support.

In Example 65, the subject matter of Example 64 optionally includes wherein the movable support further comprises: a movable body including a shaft bore extending through the body and a pivot bore substantially transverse to the shaft bore; and a pivotable jaw opposing the lateral upright and including a pivot projection disposable in the pivot bore and a pivotable jaw slot extending substantially transversely to the shaft bore, the pivotable jaw configured to pivot about the pivot bore.

In Example 66, the subject matter of any one or more of Examples 64-65 optionally include wherein at least one of the pivotable jaw slot and the fixed jaw slot comprise a geometric shape of an asymmetric V.

In Example 67, the subject matter of any one or more of Examples 64-66 optionally include wherein the movable support is threadably engageable with the shaft of the actuator.

In Example 68, the subject matter of any one or more of Examples 64-67 optionally include a torque tool releasably securable to the handle of the actuator, the torque tool including at least one radial extension.

In Example 69, the subject matter of Example 68 optionally includes wherein the torque tool includes a plurality of radial projections engageable with the handle to transfer torque between the handle and the torque tool.

In Example 70, the subject matter of any one or more of Examples 64-69 optionally include the stem further comprising: a key bit extending radially from the stem and including an angled face on a distal side of the key bit; and a flange extending radially outward from the stem proximate the key bit.

Example 71 is an adjustable instrument holder comprising: a body extending along a longitudinal axis, the body comprising: a threaded member extending along the longitudinal axis; and a stem coupled to the threaded member and extending therefrom; an axial body extending substantially along the longitudinal axis, the axial body comprising: a collar coupled to a proximal portion of the axial body, the collar threadably engageable with the threaded member of the body, and the collar operable to translate the axial body along the threaded member to adjust an axial position of the axial body relative to the body and the stem; and a driver secureable to the axial body and rotatable about a gear axis substantially transverse to, and offset from, the longitudinal axis, a rotating body rotatable relative to the axial body, the rotating body comprising: a transverse bore extending through a distal portion of the rotating body; a transverse slot intersecting the transverse bore; and a driven gear coupleable to the axial body and rotatable relative thereto, the driven gear engageable with the driver such that the driver is operable to rotate driven gear to rotate the rotating body a relative to the axial body and the stem; a transverse body translatable transverse to the rotating body; the transverse body comprising: a clamp secured to the transverse body and extending therefrom, the clamp including an instrument opening and a clamp actuator, the clamp actuator operable to open and close the instrument opening; a projection extending from the transverse body and insertable into the transverse slot; and a transverse actuator disposable in the transverse bore of the rotating body and engageable with the projection, the transverse actuator operable to translate the projection within the transverse slot to translate the transverse body and the clamp relative to the rotating body, the axial body, and the stem.

In Example 72, the subject matter of Example 71 optionally includes wherein the driver includes a worm drive engageable with the driven gear and a handle coupled to the worm drive and operable to rotate the worm drive.

In Example 73, the subject matter of any one or more of Examples 71-72 optionally include wherein the driven gear includes a worm gear driven by the worm drive.

In Example 74, the subject matter of Example 73 optionally includes wherein the rotating body includes a support coupleable to the axial body opposite the driven gear to secure the rotating body to the axial body.

In Example 75, the subject matter of any one or more of Examples 71-74 optionally include a first lock extending into the axial body and engageable with the threaded member to limit translation of the axial body relative to the threaded member.

In Example 76, the subject matter of any one or more of Examples 71-75 optionally include a second lock extending into the rotating body and engageable with the axial body to limit translation of the rotating body relative to the axial body.

In Example 77, the subject matter of any one or more of Examples 71-76 optionally include a third lock extending into the transverse body and engageable with the rotating body member to limit translation of the transverse body relative to the rotating body.

In Example 78, the subject matter of any one or more of Examples 71-77 optionally include a pin secured to the axial body and disposable in a slot extending along the longitudinal axis of the threaded member of the body to limit rotation and translation transverse to the longitudinal axis of the axial body relative to the body.

In Example 79, the subject matter of any one or more of Examples 71-78 optionally include wherein the stem includes a key bit extending radially from the stem and including an angled face on a distal side of the key bit, and a flange extending radially outward from the stem proximate the key bit.

In Example 80, the system, assembly, or method of any one of or any combination of Examples 1-79 is optionally configured such that all elements or options recited are available to use or select from.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. An end effector coupler system for an electromechanical surgical arm, the end effector coupler system comprising:
   an end effector body comprising a proximal portion and an opposite distal portion, the distal portion including a distal end;
   a control device coupleable to an external surface of the end effector body and operable to transmit a signal to allow movement of the surgical arm;
   a coupler connected to the proximal portion and releasably coupleable to the surgical arm;
   a tool lock for releasably retaining a tool stem to the end effector body, the tool lock comprising:
   a keyed opening extending through the distal end into the distal portion, the keyed opening configured to receive the tool stem therein;
   a pin bore extending through the distal end proximate to the keyed opening;

a pin disposed in the pin bore and extendable from the pin bore to engage and retain the tool stem when the tool stem is inserted into the keyed opening; and a biasing element located in the pin bore and engaging the pin to bias the pin to extend from the distal end; and a pin release comprising an actuator extending beyond an external surface of the end effector body and engaging the pin, the pin release operable to retract the pin into to the end effector body to disengage the pin from the tool stem allowing release of the tool stem from the keyed opening.

2. The system of claim 1, wherein the pin limits rotation of the tool stern relative to the keyed opening to prevent release of the tool stem from the keyed opening when the pin engages the tool stem.

3. The system of claim 1, wherein the end effector body includes a flat outer surface configured to receive the control device thereon and a tab channel extending through the flat outer surface.

4. The system of claim 3, wherein the control device includes a tab extending from the control device, a portion of the tab insertable into the tab channel to releasably secure the control device to the end effector body.

5. The system of claim 4, wherein the end effector body includes a catch extending from the flat outer surface, the catch configured to receive a portion of the tab thereon to releasably secure the control device to the end effector body.

6. The system of claim 1, wherein the control device includes a light indicator configured to indicate a condition of the end effector coupler.

7. The system of claim 1, wherein the keyed opening further comprises a keyway extending radially from a central tapered bore of the keyed opening and sized to receive a key bit of the tool stem therethrough, the key bit including an angled face engageable with a proximal portion of the keyway to limit axial movement of the tool stem relative to the keyed opening, and wherein the central tapered bore is configured to receive a complimentary tapered section of the tool stem to form a taper-to-taper interface to limit relative motion between the end effector coupler and the tool stem, wherein a distal portion of the pin is configured to engage a notch of the tool stem to limit rotation of the tool stem relative to the end effector coupler, and wherein the angled face is configured to engage the proximal portion of the keyway substantially simultaneously with the central tapered bore in receipt of the complimentary tapered section of the tool stem and substantially simultaneously with the distal portion of the pin in engagement with the notch of the tool stem.

8. The system of claim 1, further comprising:
a tool including the tool stem, the tool configured to retain an instrument therein, and the tool releasably coupleable to the end effector.

9. The system of claim 8, wherein the tool further comprises:
a shaft including a coupling bore proximate a distal end of the shaft, the coupling bore transverse to a longitudinal axis of the shaft and configured to receive an instrument, and the tool stem extending proximally from the shaft;
a clamping sleeve disposed on the shaft and axially translatable along the longitudinal axis of; and
a collar disposed on the shaft and threadably engaged with the shaft to control axial translation of the collar on the shaft, the collar engageable with the clamping sleeve to translate the clamping sleeve with the collar, wherein axial translation of the clamping sleeve controls engagement of a distal edge of the clamping sleeve with the instrument to lock the instrument in position within the coupling bore.

10. The system of claim 9, further comprising:
a collar biasing element engaging the collar and the sleeve to bias the sleeve away from the collar.

11. The system of claim 8, wherein the tool further comprises:
a body including a proximal end and a distal end and a longitudinal axis extending therethrough, the tool stem coupled to the body and extending therefrom;
a first platform fixedly coupled to the body;
a second platform coupled to the body, the second platform opposing the first platform, and the second platform translatable relative to the body and the first platform, wherein the first platform and the second platform include opposing structure to retain a standard surgical instrument upon translation of the second platform toward the first platform; and
an actuator engaging the second platform and the body, the actuator operable to translate the second platform relative to the body along the longitudinal axis.

12. The system of claim 11, wherein first platform includes a v-groove extending transversely to the longitudinal axis, the v-groove at least partially shaped to conform to a straight portion of the surgical instrument, and wherein the second platform includes a first protrusion extending from the second platform toward the v-groove, the first protrusion insertable into the v-groove to retain the straight portion of the surgical instrument between the first platform and the straight portion.

13. The system of claim 8, wherein the tool further comprises:
a body, the tool stem coupled thereto, the body comprising:
a proximal portion;
a distal portion opposite the proximal portion; and
a retaining bore extending along a longitudinal axis of the body;
a jaw forming a portion of two sides of the retaining bore opposite the proximal portion of the body in a first retracted state, the jaw translatable relative to the body into a second extended state where the jaw reduces the size of the retaining bore; and
an actuator engageable with the distal portion and operable to translate the jaw relative to the proximal portion to adjust a size of the retaining bore.

14. The system of claim 13, wherein the jaw includes a geometric shape substantially of a H in a parallel plane that is parallel to the longitudinal axis of the body, and wherein the jaw includes a geometric shape substantially of a V in a transverse plane that is transverse to the longitudinal axis of the body.

15. The system of claim 8, wherein the tool further comprises:
a body including a proximal portion and a distal portion and comprising a substantially cylindrical geometric shape, the body extending along a longitudinal axis;
a first platform fixedly coupled to the proximal portion of the body and extending radially, from the body, the tool stem coupleable to the body proximal of the first platform and extending radially from the proximal portion of the body;
a second platform coupled to the body proximate the first platform, the second platform extending radially from the body, the second platform opposing the first platform, and the second platform translatable relative to the body and the first platform; and an actuator securable to the distal portion of the body and engageable with the second platform, the actuator operable to translate the second platform relative to the body along the longitudinal axis.

16. The system of claim 15, wherein the body further includes an axial slot extending between the proximal portion of the body and the distal portion of the body, the tool further comprising a retaining pin disposable in the axial slot and engageable with a bore of the second platform to limit translation of the platform relative to the body and to limit translation of the second platform relative to the body.

17. The system of claim 8, wherein the tool further comprises:
   a body substantially forming a u-shape, the tool stem coupled to the body and extending therefrom, the body comprising:
   a base extending substantially longitudinally and including a medial portion and a lateral portion;
   a lateral upright extending substantially transversely from the lateral portion of the base, the lateral upright including a lateral bore and a fixed jaw slot extending substantially transversely to the lateral bore; and
   a medial upright extending substantially transversely from the medial portion of the base opposite the lateral upright, the medial upright including a medial bore;
   an actuator comprising:
   a shaft coupleable to the lateral bore and the medial bore and extending there between; and
   a handle coupled to the shaft and extending laterally away from the lateral upright;
   a movable support opposing the lateral support, the movable support coupleable to the shaft and translatable along the shaft;
   wherein the actuator is operable to translate the movable support relative to the lateral support along the longitudinal axis to retain a surgical instrument between the movable support and the lateral support.

18. The system of claim 17, wherein the movable support further comprises:
   a movable body including a shaft bore extending through the movable body and a pivot bore substantially transverse to the shaft bore; and
   a pivotable jaw opposing the lateral upright and including a pivot projection disposable in the pivot bore and a pivotable jaw slot extending substantially transversely to the shaft bore, the pivotable jaw configured to pivot about the pivot bore.

19. The system of claim 8; wherein the tool further comprises:
   a body extending along a longitudinal axis, the body comprising:
   a threaded member extending along the longitudinal axis, the tool stem coupled to the threaded member and extending therefrom;
   an axial body extending substantially along the longitudinal axis, the axial body comprising:
   a collar coupled to a proximal portion of the axial body, the collar threadably engageable with the threaded member of the body, and the collar operable to translate the axial body along the threaded member to adjust an axial position of the axial body relative to the body and the tool stem; and
   a driver securable to the axial body and rotatable about a gear axis substantially transverse to, and offset from, the longitudinal axis, a rotating body rotatable relative to the axial body, the rotating body comprising:
   a transverse bore extending through a distal portion of the rotating body;
   a transverse slot intersecting the transverse bore; and
   a driven gear coupleable to the axial body and rotatable relative thereto, the driven gear engageable with the driver such that the driver is operable to rotate driven gear to rotate the rotating body a relative to the axial body and the tool stem; and
   a transverse body translatable transverse to the rotating body; the transverse body comprising:
   a clamp secured to the transverse body and extending therefrom, the clamp including an instrument opening and a clamp actuator, the clamp actuator operable to open and close the instrument opening;
   a projection extending from the transverse body and insertable into the transverse slot; and
   a transverse actuator disposable in the transverse bore of the rotating body and engageable with the projection, the transverse actuator operable to translate the projection within the transverse slot to translate the transverse body and the damp relative to the rotating body, the axial body, and the tool stem.

20. The system of claim 19, wherein the driver includes a worm drive engageable with the driven gear and a handle coupled to the worm drive and operable to rotate the worm drive, and wherein the driven gear includes a worm gear driven by the worm drive.

* * * * *

UNITED STATES PATENT AND TRADEMARK OFFICE
CERTIFICATE OF CORRECTION

PATENT NO. : 10,772,704 B2
APPLICATION NO. : 15/919150
DATED : September 15, 2020
INVENTOR(S) : Garcia et al.

It is certified that error appears in the above-identified patent and that said Letters Patent is hereby corrected as shown below:

In the Claims

In Column 49, Line 13, in Claim 2, delete "stern" and insert --stem-- therefor

In Column 49, Line 53, in Claim 8, delete "effector." and insert --effector body.-- therefor In Column 50, Line 61, in Claim 15, delete "radially," and insert --radially-- therefor In Column 52, Line 1, in Claim 19, delete "8;" and insert --8,-- therefor In Column 52, Line 16, in Claim 19, delete "securable" and insert --secureable-- therefor In Column 52, Line 42, in Claim 19, delete "damp" and insert --clamp-- therefor Signed and Sealed this
Fifteenth Day of December, 2020

Andrei Iancu
*Director of the United States Patent and Trademark Office*